United States Patent
Van Ginderachter et al.

(10) Patent No.: US 11,083,751 B2
(45) Date of Patent: Aug. 10, 2021

(54) TUMOR-ASSOCIATED DENDRITIC CELL PREPARATIONS AND USES THEREOF

(71) Applicants: VIB VZW, Ghent (BE); VRIJE UNIVERSITEIT BRUSSEL; UNIVERSITEIT GENT, Ghent (BE)

(72) Inventors: Jo Van Ginderachter, Ninove (BE); Damya Laoui, Limal (BE); Jiri Keirsse, Bornem (BE); Martin Guilliams, Blaasveld (BE)

(73) Assignees: VIB VZW, Ghent (BE); Vrije Universiteit Brussel, Brussels (BE); Universiteit Gent, Ghent (BE)

( * ) Notice: Subject to any disclaimer, the term of this patent is extended or adjusted under 35 U.S.C. 154(b) by 247 days.

(21) Appl. No.: 16/079,674

(22) PCT Filed: Feb. 22, 2017

(86) PCT No.: PCT/EP2017/054042
§ 371 (c)(1),
(2) Date: Aug. 24, 2018

(87) PCT Pub. No.: WO2017/144522
PCT Pub. Date: Aug. 31, 2017

(65) Prior Publication Data
US 2019/0054116 A1   Feb. 21, 2019

(30) Foreign Application Priority Data
Feb. 26, 2016   (EP) .................................... 16157684

(51) Int. Cl.
| | |
|---|---|
| A61K 35/15 | (2015.01) |
| A61K 39/00 | (2006.01) |
| C12N 5/0784 | (2010.01) |
| C12N 5/078 | (2010.01) |
| A61P 35/04 | (2006.01) |

(52) U.S. Cl.
CPC .......... *A61K 35/15* (2013.01); *A61K 39/0011* (2013.01); *A61P 35/04* (2018.01); *C12N 5/0639* (2013.01); *C12N 5/0651* (2013.01); *A61K 2039/5154* (2013.01); *A61K 2039/572* (2013.01); *A61K 2039/575* (2013.01)

(58) Field of Classification Search
None
See application file for complete search history.

(56) References Cited

U.S. PATENT DOCUMENTS

2003/0022249 A1*  1/2003  Schmitz ............. G01N 33/6863
                                                                435/7.21

FOREIGN PATENT DOCUMENTS

| WO | WO-2015112749 A2 * | 7/2015 | ......... A61K 31/7105 |
|---|---|---|---|
| WO | 2016038168 | 3/2016 | |

OTHER PUBLICATIONS

Piccioli et al., 2007, Immunobiology, vol. 109: 5371-5379.*
Collin et al., 2013, Immunology vol. 140: 22-30.*
Merad et al., 2013, Ann. Rev. Immunol. vol. 31: 1-48.*
Segura et al., 2013, Trends Immunol. vol. 34: 440-445.*
Breton G et al. "Human blood contains two subsets of dendritic cells, one immunologically mature and the other immature", The Journal of Experimental Medicine, vol. 82, No. 3, Feb. 16, 2015 (Feb. 16, 2015), pp. 401-413.
Bronte, V, and P Zanovello. "Regulation of Immune Responses by L-Arginine Metabolism." Nature Reviews Immunology, vol. 5, No. 8, 2005, pp. 641-654.
Broz, Miranda L. et al., "Dissecting the Tumor Myeloid Compartment Reveals Rare Activating Antigen-Presenting Cells Critical for T Cell Immunity." Cancer Cell. 26.6 (2014): 938-938.
Gautier, Emmanuel L, et al. "Gene-Expression Profiles and Transcriptional Regulatory Pathways That Underlie the Identity and Diversity of Mouse Tissue Macrophages." Nature Immunology, vol. 13, No. 11, 2012, pp. 1118-1128.
Greter, et al. "GM-CSF Controls Nonlymphoid Tissue Dendritic Cell Homeostasis but Is Dispensable for the Differentiation of Inflammatory Dendritic Cells." Immunity, vol. 36, No. 6, 2012, pp. 1031-1046.
Guilliams M., et al. "Dendritic Cells, Monocytes and Macrophages: a Unified Nomenclature Based on Ontogeny." Nature Reviews. Immunology. 14.8 (2014): 571-8.
Keirsse, Jiri, et al. "Exploiting Tumor-Associated Dendritic Cell Heterogeneity for Novel Cancer Therapies." Journal of Leukocyte Biology, vol. 102, No. 2, 2017, pp. 317-324.
Laoui, Damya, et al. "Purification of Tumor-Associated Macrophages (TAM) and Tumor-Associated Dendritic Cells (TADC)." BIO-PROTOCOL, vol. 4, No. 22, 2014, pp. BIO-PROTOCOL, 2014, vol. 4(22).
Laoui, Damya, et al. "The Tumour Microenvironment Harbours Ontogenically Distinct Dendritic Cell Populations with Opposing Effects on Tumour Immunity." Nature Communications, vol. 7, 2016, p. 13720.
Merad, Miriam, et al. "The Dendritic Cell Lineage: Ontogeny and Function of Dendritic Cells and Their Subsets in the Steady State and the Inflamed Setting." Annual Review of Immunology, vol. 31, vol. 31, No. 1, 2013, pp. 563-604.
O'Doherty U., et al. "Human blood Containing Two Subsets of Dendritic Cells, One Immunonologically Mature and the Other Immature." Immunology, vol. 82, 1994, pp. 487-493.

(Continued)

*Primary Examiner* — Amy E Juedes
(74) *Attorney, Agent, or Firm* — Patent Law Works, LLP

(57) ABSTRACT

The present application relates to tumor-associated dendritic cell (TADC) preparations and their use in treatment of tumor metastasis.

7 Claims, 37 Drawing Sheets
Specification includes a Sequence Listing.

(56) References Cited

OTHER PUBLICATIONS

Ohl, et al. "CCR7 Governs Skin Dendritic Cell Migration under Inflammatory and Steady-State Conditions." Immunity, vol. 21, No. 2, 2004, pp. 279-288.

PCT International Search Report and Written Opinion for PCT/EP2017/054042, dated May 17, 2017.

Plantinga, et al., "Conventional and Monocyte-Derived Cd11b+ Dendritic Cells Initiate and Maintain T Helper 2 Cell-Mediated Immunity to House Dust Mite Allergen." Immunity. 38.2 (2013): 322-335.

Steinman, Ralph M., and Jacques Banchereau. "Taking Dendritic Cells into Medicine." Nature, vol. 449, No. 7161, 2007, pp. 419-426.

Gilboa, Eli. "DC-Based Cancer Vaccines." The Journal of Clinical Investigation, vol. 117, No. 5, 2007, pp. 1195-1203.

Haen, Sebastian P, et al. "Towards New Horizons: Characterization, Classification and Implications of the Tumour Antigenic Repertoire." Nature Reviews Clinical Oncology. 17.10 (2020): 595-610.

* cited by examiner

D

D

D

E

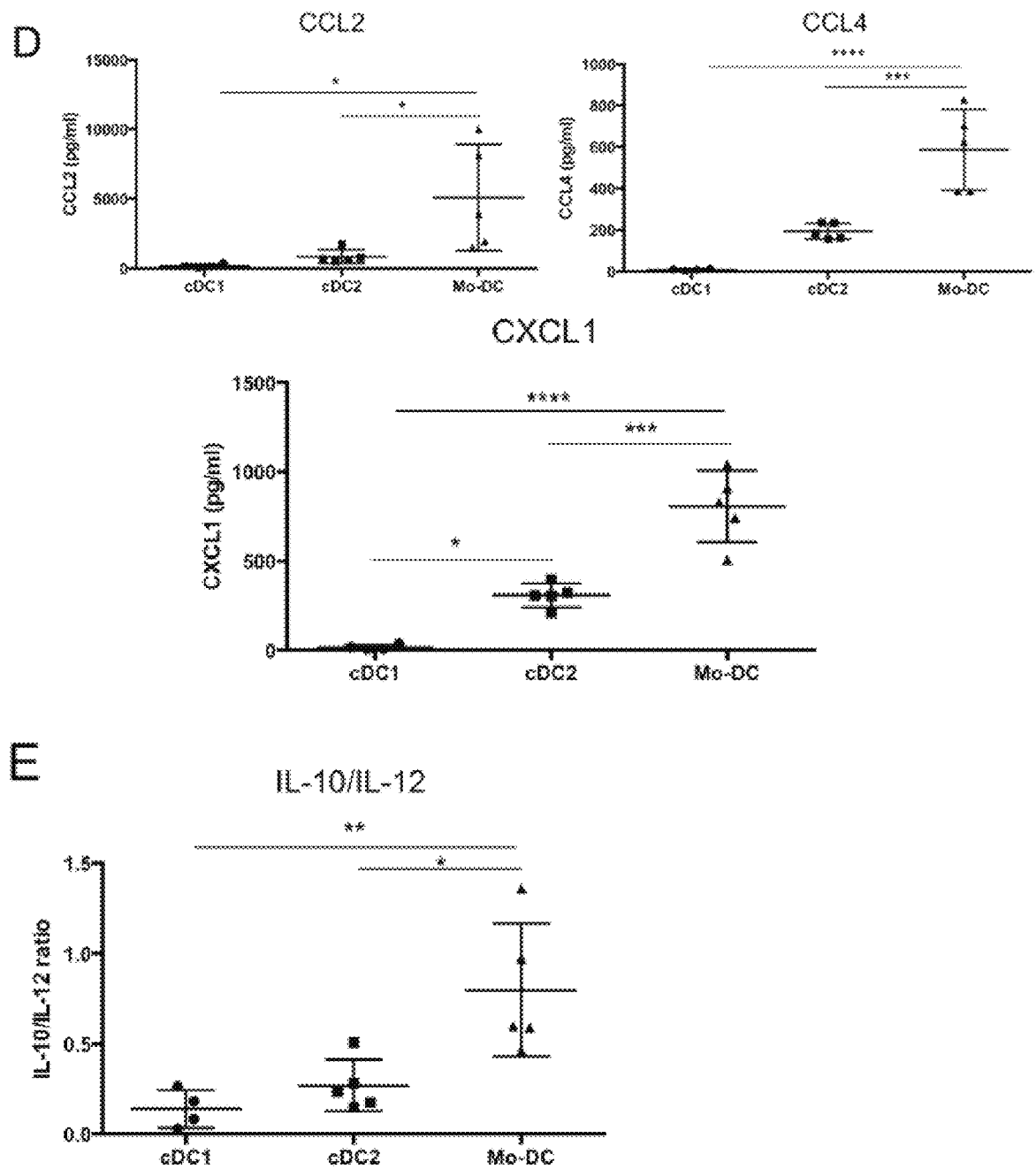

D

E

F

G

H

SEQUENCE LISTING

<160> NUMBER OF SEQ ID NOS: 23

<210> SEQ ID NO 1

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 1
tcacctgagc tttgatgtcg                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ttatggttac cctcccgttg                                               20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtgtggatcc aaagcaatac                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gtctgctcat tcatgacaag                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcagatggct catgtctgaa                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctctgggaag ctgggtgtag                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
```
tcagggacat catcaaacca                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctacgaggaa cgcacctttc                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgaatcagct ggcttttgtg                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gtggatagct cggtggtgtt                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcaaatggag ccgtctgtgc                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ctcgtggatc tccgtgacac                                              20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gcttctggtc gatgtcatga g                                            21

<210> SEQ ID NO 14
<211> LENGTH: 20
<212> TYPE: DNA

```
<213> ORGANISM: Artificial Sequence
<220> FEATURE:
<223> OTHER INFORMATION: Primer

<400> SEQUENCE: 14
tccaccagga gatgttgaac                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cgtggattct caaactgcaa                                                   20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caccaacatg ctcattgtcc                                                   20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
caggctgaac ttcgaaacag                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cagctacgaa aacccaatca                                                   20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
acgggaaact gcttgatgtc                                                   20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
actcagcgtc atgttgtcca                                                   20
```

```
<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ccttcacaga gcaatgactc                                                 20

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gtctactccc aggttctctt c                                               21

<210> SEQ ID NO 23
<211> LENGTH: 8
<212> TYPE: PRT
<213> ORGANISM: Artificial Sequence
<220> FEATURE:
<223> OTHER INFORMATION: immunodominant CTL epitope

<400> SEQUENCE: 23

Ser Ile Ile Asn Phe Glu Lys Leu
1               5
```

TUMOR-ASSOCIATED DENDRITIC CELL PREPARATIONS AND USES THEREOF

FIELD OF THE INVENTION

The present application relates to tumor-associated dendritic cell (TADC) preparations and their use in treatment of tumor metastasis.

BACKGROUND

Dendritic cells (DCs) are specialized antigen-presenting cells (APCs) present in all tissues that play a major role in orchestrating immune responses (Steinman and Banchereau, 2007). DCs isolated from various steady-state and inflamed tissues have been shown to represent a heterogeneous population consisting of developmentally distinct DC subsets (Guilliams et al., 2010; Helft et al., 2010; Plantinga et al., 2013), including cDC1 (CD8α+-like or CD103+ conventional DC), cDC2 (CD11b+-like cDC), plasmacytoid DC (pDCs) and so-called monocyte-derived DC (Mo-DC) (Guilliams et al., 2014; Guilliams et al., 2010; Heath and Carbone, 2009). cDCs arise from bone marrow-derived pre-cDC precursors in a Flt3L-dependent fashion (Onai et al., 2007), are maintained under homeostatic conditions by GM-CSFR signaling (Greter et al., 2012) and differentiate into cDC1 and cDC2 under the control of BATF3, ID2 and IRF8 or RELB and IRF4, respectively. Mo-DCs differentiate from Ly6Chi monocytes which exit the bone marrow in a CCR2-dependent manner and were reported not to require GM-CSFR signaling for their in vivo differentiation (Greter et al., 2012; Serbina et al., 2008). Importantly, DCs of distinct cellular origin have been shown to display a differential functional specialization. While cDC1 are specialized in the induction of cytotoxic T cell (CTL) responses, cDC2 have been shown to excel at the induction of Th17 or Th2 responses (Gao et al., 2013; Persson et al., 2013; Plantinga et al., 2013; Schlitzer et al., 2013). Although the migratory potential of Mo-DCs is debated, they have been proposed to reactivate effector T cells in inflamed tissues (Plantinga et al., 2013). Whether the various functions ascribed to tumor-associated DCs (TADCs) are in fact performed by distinct DC subsets is unknown but the recent report of cDC1 presence in tumors (Broz et al., 2014) emphasizes that the tumor tissue may, like any other tissue, be populated by DCs with distinct developmental origin and possibly a differential functional specialization. As a matter of fact, subpopulations of tumor-associated macrophages (TAM) with distinct functions have been identified (Laoui et al., 2014; Movahedi et al., 2010).

The presence of mature DCs in tumors has been correlated with a positive prognosis in several tumor types (Fridman et al., 2011; Goc et al., 2014). DC-based immunotherapy attempts to exploit the power of DCs and the specificity of the immune system to treat tumors. In this process, the crucial step is to provide mature DCs that present tumor-specific antigens. The current standard approach in DC-based immunotherapy is the use of ex vivo cultured DCs that were loaded with tumor-associated antigen (TAA) and activated by cytokines. Nevertheless, the process of antigen loading is not always efficient and requires up-front knowledge of the TAAs present in a specific tumor and ex vivo cell culturing is labor intensive. Furthermore, isolation and cell culture procedures may employ either sheep red blood cells and/or fetal calf serum, both of which contain potentially immunogenic foreign antigens, which can interfere with the utility of the purified DCs. Although phenotypic analysis of DCs following ex vivo maturation in culture medium demonstrate requisite cell surface markers, functionally the DCs may fail to drive the immune response in an effective manner following transfer into the host. Indeed, clinical responses to ex vivo generated mature DCs have been moderate. This might be partly explained by the lack of an effective inflammation at the tumor side, which can lead to tolerance induction. There is evidence that the lack of effectiveness is due to the wrong choice of DCs (mostly Mo-DCs) and the failure of these DCs to migrate to the lymph nodes. Our understanding of what defines the interaction between a DC and a T cell at the tumor site and what drives the interaction from a tolerogenic mode to a responsive mode is still very poor. In summary, the prior art teaches that complex cell culture methods in the presence of cytokines are necessary for generation of mature DCs, but clinical responses to those DCs are rather poor. There is a need for DCs or DC compositions that do not have the above mentioned limitations and that induce an effective anti-tumor immune response.

SUMMARY

We have characterized, purified and utilized TADCs from tumor tissue. Surprisingly, we found that TADCs from tumor tissue can induce anti-tumoral immune responses. This is advantageous over the currently available DC-based immunotherapy strategies, as TADCs naturally present TAAs, including yet to be defined TAAs, and they do not need to be cultured ex vivo. Furthermore, our data surprisingly demonstrate that ontogenically distinct TADC populations elicit different therapeutic effects.

It is an aspect of the present invention to provide an isolated TADC subset of pre-cDC origin, essentially devoid of Mo-DCs, wherein said TADC subset is obtained from a resected tumor or a resected tumor-draining lymph node of a mammal, for use in treatment of tumor metastasis in said mammal.

In one embodiment, the invention envisages a TADC subset that comprises no more than 1% Mo-DCs.

In one embodiment, the invention envisages a TADC subset that has the characteristic cell surface phenotype of at least CD16− CD11c+ HLA-DR+ BDCA2− CD14−. The TADC subset as described above may be further characterized as BDCA1− BDCA3+ CD11b−.

In one embodiment, the invention envisages a TADC subset that has the characteristic cell surface phenotype of at least CD16− CD11c+ HLA-DR+ BDCA2− CD14−. The TADC subset as described above may be further characterized as BDCA1+ BDCA3− CD11b+.

Also envisaged is a TADC subset as described above, prepared by a process comprising the steps of (a) isolating TADCs from a resected tumor or a resected tumor-draining lymph node of a mammal, and (b) enriching TADC subsets in a manner effective to obtain a population essentially devoid of Mo-DCs. In one particular embodiment, said enrichment includes one or more of buoyant density centrifugation, magnetic-activated cell sorting (MACS) and fluorescently activated cell sorting (FACS).

The invention also relates to anyone of the TADC subsets described above for the use in treatment of tumor metastasis.

According to another aspect, the invention also relates to a pharmaceutical composition comprising the TADC subset as described above, for use in treatment of tumor metastasis.

Also envisaged is a method of treating tumor metastasis in a mammal, the method comprising administering to said mammal a therapeutically effective amount of the TADC subset as described above or the pharmaceutical composition as described above.

Objects of the present invention will be clear from the description that follows.

DETAILED DESCRIPTION

Figure 1:
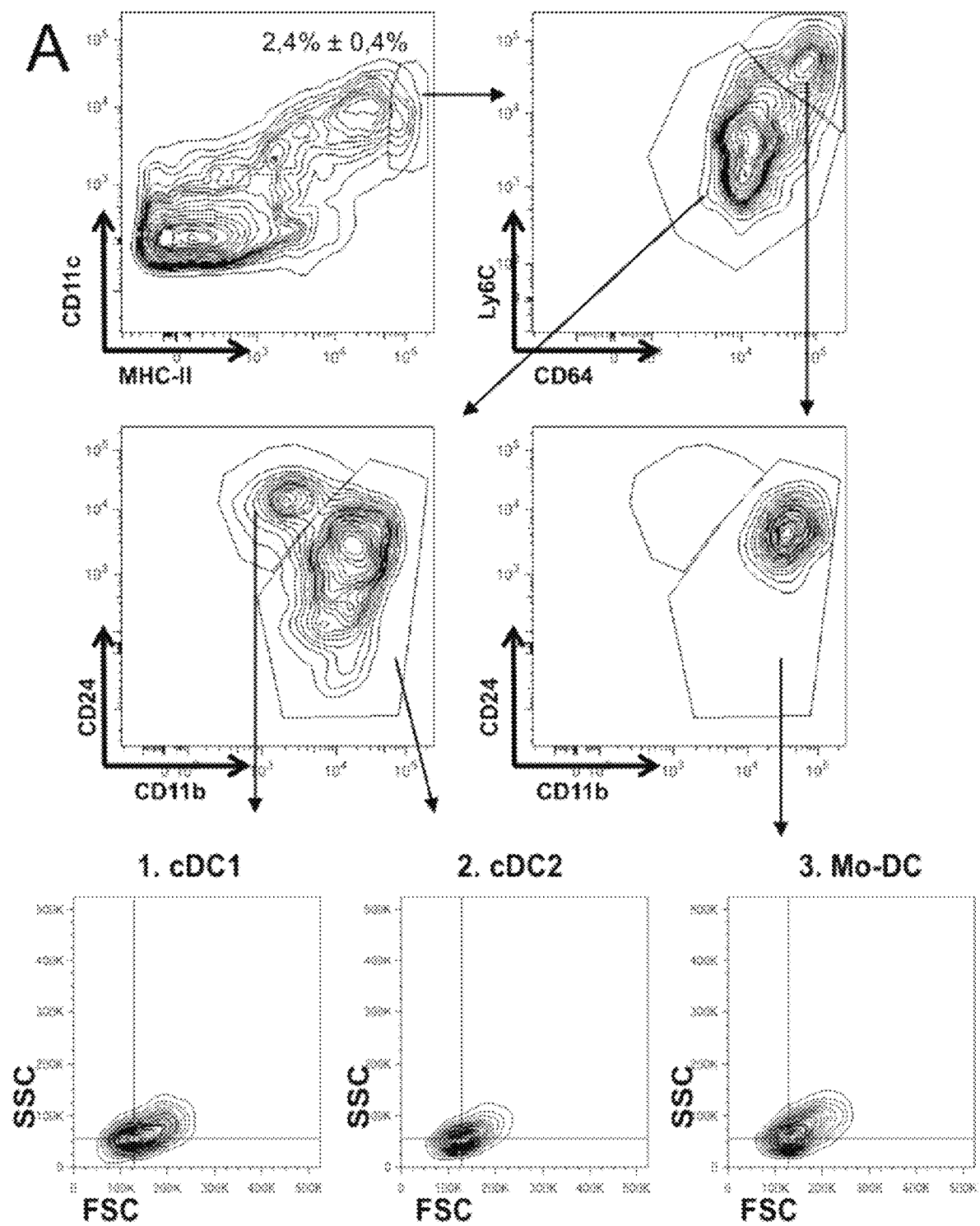
FIG. 1 shows the origin of different TADC subpopulations. (A) TADCs of 12-day old 3LL-R tumors were subdivided in (1) $CD64^{neg}$ $CD24^{pos}$ $CD11b^{lo}$ cDC1, (2) $CD64^{neg}$ $CD24^{neg}$ $CD11b^{pos}$ $Ly6C^{lo}$ cDC2 and (3) $CD64^{pos}$ $CD24^{int}$ $CD11b^{pos}$ $Ly6C^{hi}$ Mo-DC. For each subset, forward scatter vs. side scatter plots are shown. Results are representative of 4 independent experiments with $n \geq 4$. (B) Pre-cDC ($B220^-CD11c^+Sirp\alpha^{int}$) and monocyte precursors ($CD11b^+Ly6G^-Ly6C^+MHC-II^-$) were sorted from $CD45.2^+$ bone marrow and labeled with CellTrace. Either $4.10^5$ pre-cDC or $1.10^6$ monocytes were adoptively transferred intravenously (IV) to CD45.1 3LL-R tumor-bearing recipient mice. 3 days later, tumors were processed and transferred cells were gated based on their $CD45.1^-CD45.2^+CellTrace^+$ phenotype. Results are representative of 2 independent experiments with n=2 to 4. (C) 3LL-R tumors were grown for 12 days in WT, CCR2-KO, Flt3L-KO and GM-CSFR KO mice. The percentage of each TADC subpopulation within the total tumor single-cell suspension was determined. Results are representative of 2 independent experiments with n=6. Statistical analysis by two-way ANOVA. *, $p<0.05$; , $p<0.01$; *, $p<0.001$; ****, $p<0.0001$. (D) Single cell suspensions of 12-day old 3LL-R tumors were stained for the indicated markers and histogram overlays are shown for the TADC subsets. Black line=expression of the indicated marker; shaded histogram=isotype control. $\Delta MFI \pm SEM$ are indicated and represent (MFI SIINFEKL MFI control). Results are representative of 2 independent experiments with Statistical analysis by one-way ANOVA. *, $p<0.05$; , $p<0.01$; *, $p<0.001$; ****, $p<0.0001$.
Figure 1:
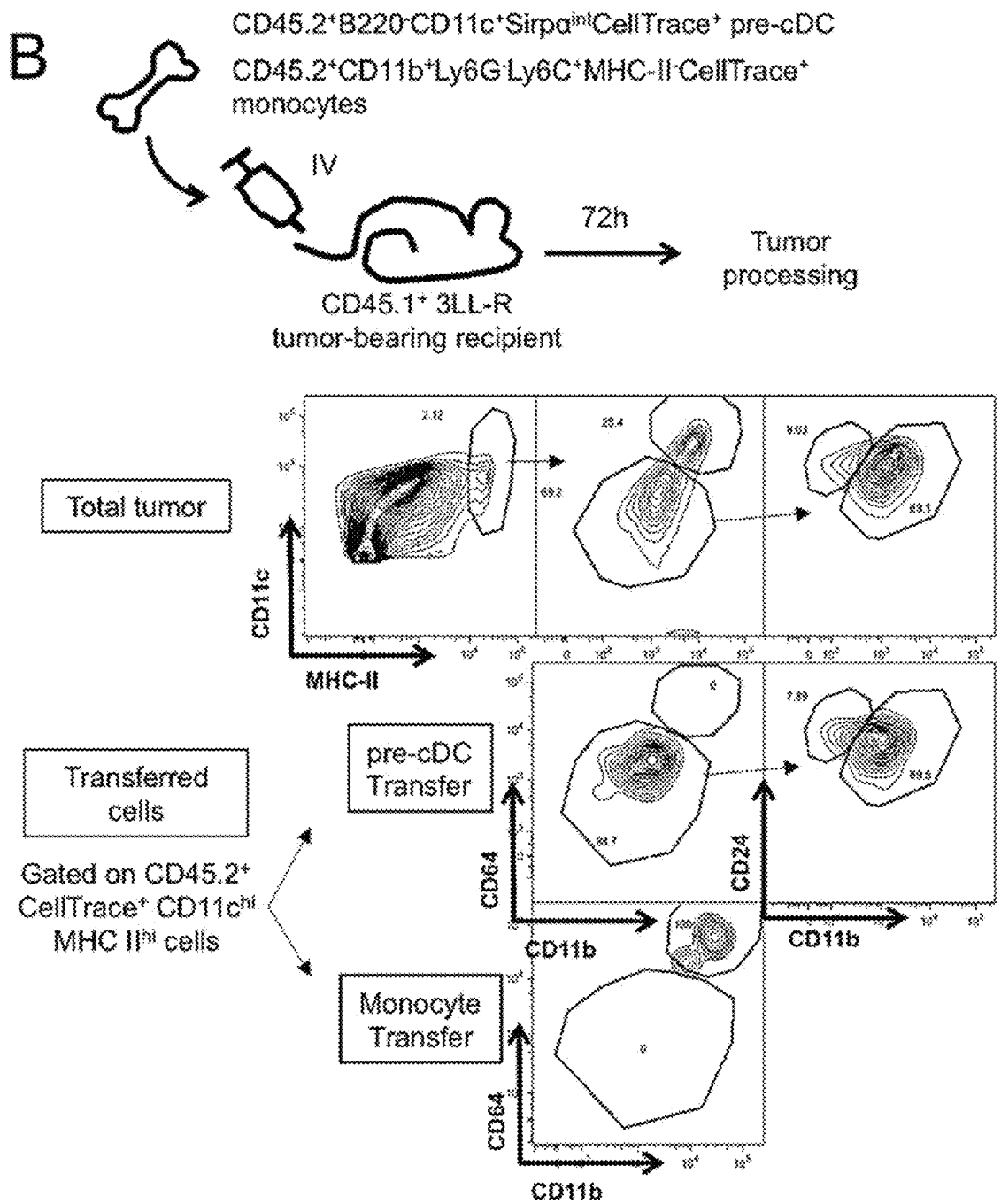
Figure 1:
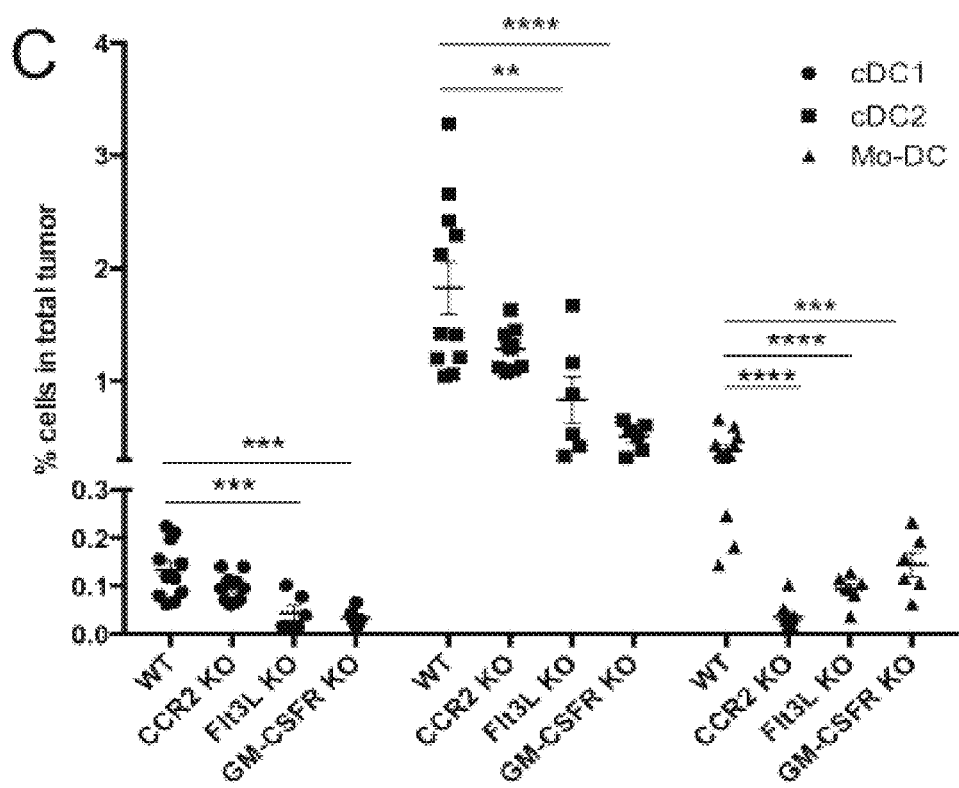
Figure 1:
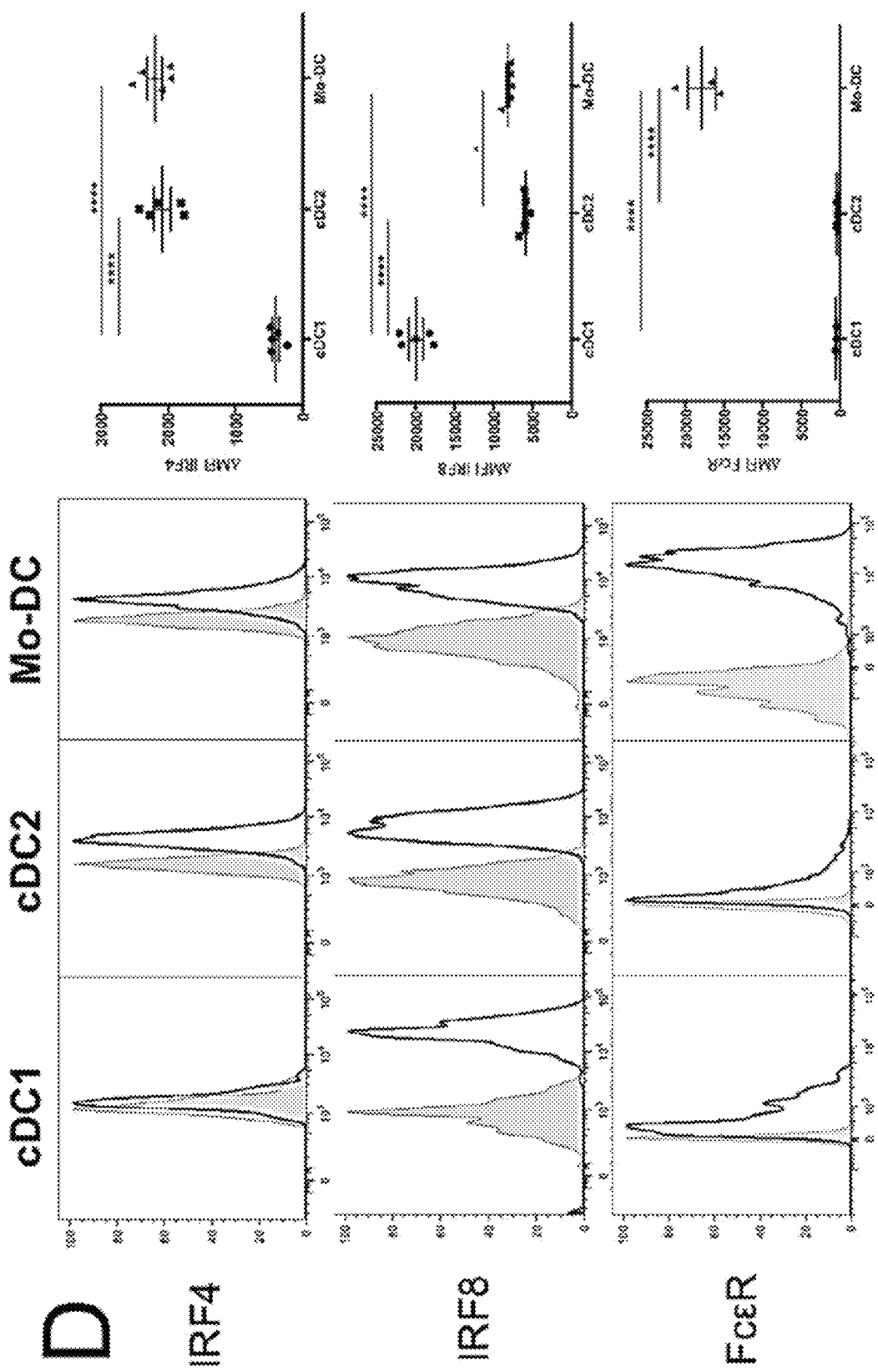
Figure 1:
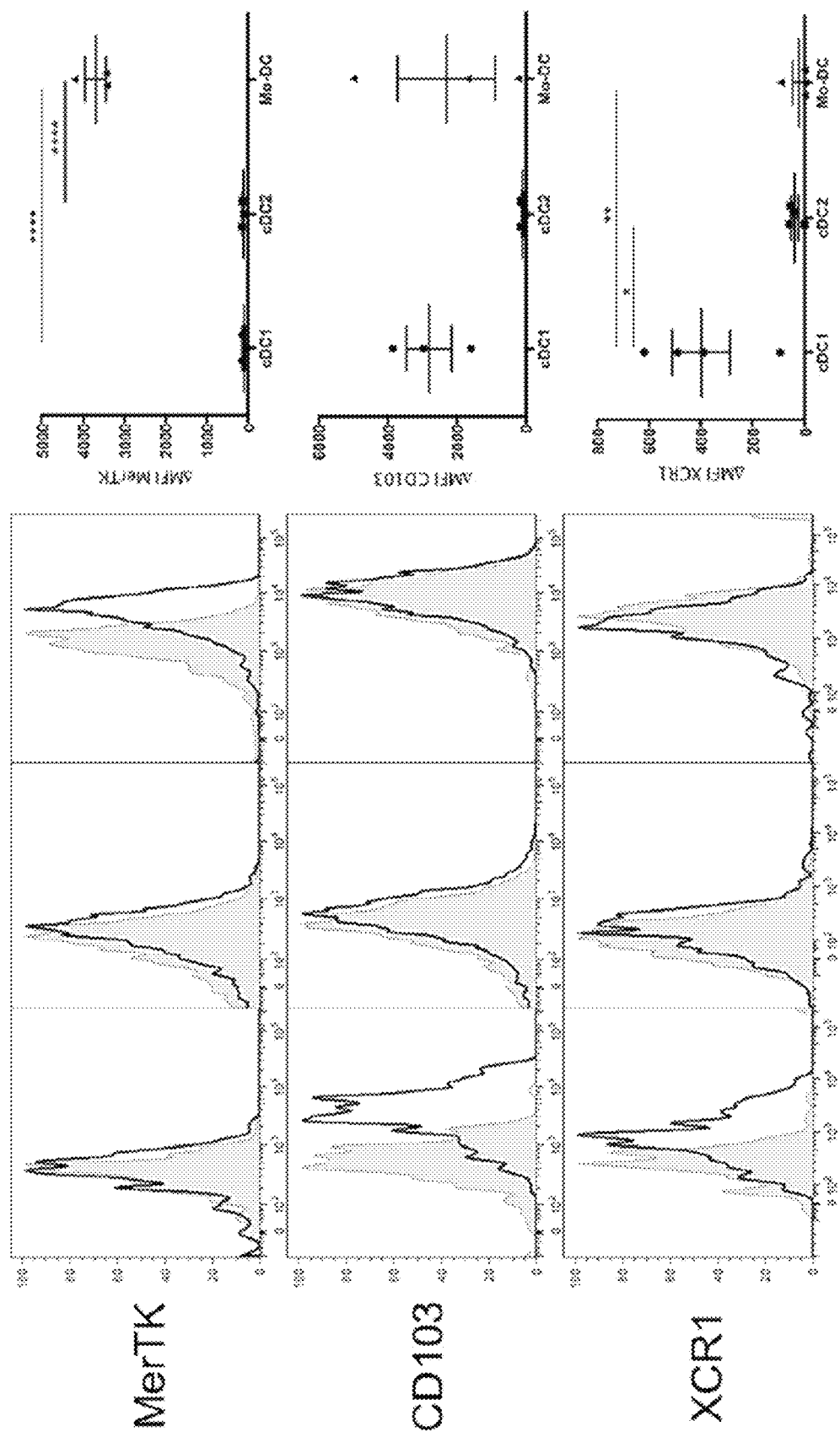
Figure 1:
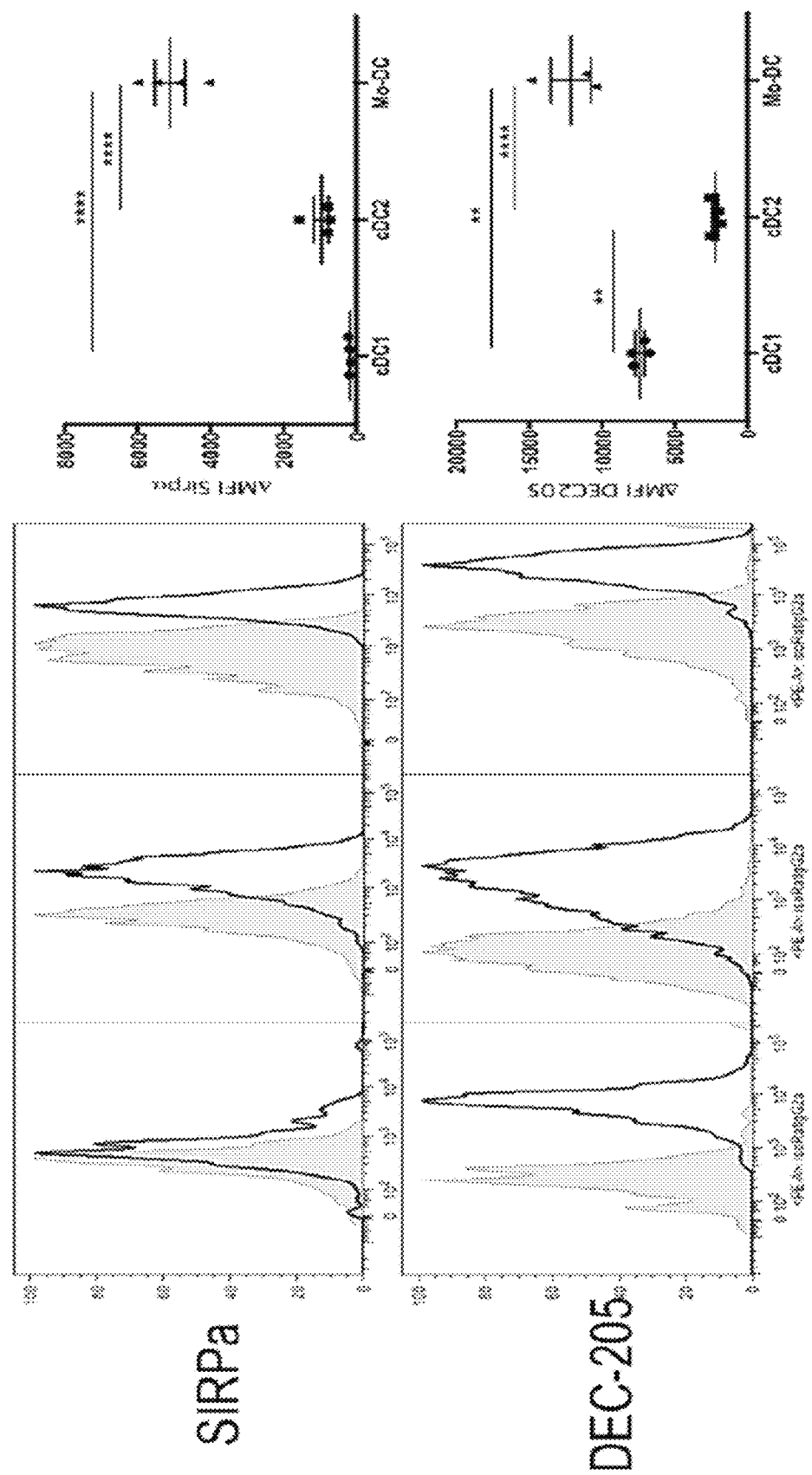

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a", "an" or "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The cell surface markers included in this invention may refer to human cell surface markers or any orthologous cell surface markers that are functionally equivalent. Therefore, cell surface markers may also refer to e.g. but not limited to mouse cell surface markers.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

A "dendritic cell" or "DC" is an APC that typically expresses the MHC class II cell surface antigen HLA-DR (human leukocyte antigen DR) and co-stimulatory molecules, and lacks expression of (or has low expression of) markers specific for granulocytes, NK cells, B lymphocytes, and T lymphocytes. DCs are able to initiate antigen specific primary T lymphocyte responses in vitro and in vivo, and direct a strong mixed leukocyte reaction (MLR) compared to peripheral blood leukocytes, splenocytes, B cells and monocytes. Generally, DCs ingest antigen by phagocytosis or pinocytosis, degrade it, present fragments of the antigen at their surface and secrete cytokines.

A "tumor-associated dendritic cell" or "TADC" is a DC derived from a tumor microenvironment.

A "pre-conventional DC" or "pre-cDC", as used herein, is a hematopoietic precursor cell derived from the bone marrow and committed to the DC lineage, whereas said pre-cDC is distinct from monocytes and monocyte-derived DCs and whereas said pre-cDC is a partially differentiated cell having the capacity of undergoing further differentiation into conventional DCs.

A "conventional DC" or "cDC" is a fully differentiated DC derived from a pre-cDC precursor cell. cDCs are characterized by the cell surface phenotype of at least CD16− CD11c+ HLA-DR+ BDCA2− and CD14−.

A "monocyte-derived dendritic cell" or "Mo-DC" is a cell derived from peripheral blood monocytes and characterized by expression of at least HLD-DR, CD11c, BDCA1, CD11b and CD14.

A TADC subset "essentially devoid of monocyte-derived dendritic cells (Mo-DCs)", as used herein, is an essentially pure TADC subset that may include unavoidable levels of impurities of Mo-DCs but no more. This means that the TADC subset is essentially pure and comprises no more than 1% Mo-DCs. For instance, "essentially devoid of Mo-DCs" can mean 1%, 0.9%, 0.8%, 0.7%, 0.6%, 0.5%, 0.4%, 0.3%, 0.2%, 0.1% or less Mo-DCs. It can also mean 0% Mo-DCs, referring to a lack of a detectable amount of Mo-DCs.

The term "isolated", as used herein, means having been removed from its natural environment. "Isolated" does not require absolute isolation; rather, it is intended as a relative term. Thus, for example, an isolated cell subset is one in which said cell subset is more pure than the cell subset in its natural environment within a tissue.

The term "enriched", as used herein, means having increased the purity of a cell type or cell subset within a cell population. "Enriched" does not require absolute enrichment; rather, it is intended as a relative term. Thus, for example, an enriched cell subset is one in which said cell subset is more pure than the purity of said cell subset before enrichment.

As used herein, the term "BDCA3+" or "BDCA3 positive" refers to a characteristic cell surface phenotype and means that cells are immunoreactive with antibodies specific to BDCA3, i.e. the results of a flow cytometry analysis of cells stained with a fluorescently labeled anti-BDCA3 antibody indicate a shift in fluorescence intensity compared to the same cells stained with an isotype control antibody, using the same procedure. Such cells are said to express BDCA3 on the cell surface. Likewise, "BDCA3−" or "BDCA3 negative" means the cells are not immunoreactive with antibodies specific to BDCA3, i.e. the results of a flow cytometry analysis of cells stained with a fluorescently labeled anti-BCDA3 antibody indicate no detectable shift in fluorescence intensity compared to the same cells stained with an isotype control antibody, using the same procedure. Such cells are said to not express BDCA3 on the cell surface. The same applies to the surface expression of BDCA1, BDCA2, CD11b, CD11c, CD14, CD16 and HLA-DR. "BDCA1+" cells are said to express BDCA1 on the cell surface, whereas "BDCA1−" cells are said to be negative for BDCA1 cell surface expression. "BDCA2−" cells are said to be negative for BDCA2 cell surface expression. "CD11b+" cells are said to express CD11b on the cell surface, whereas "CD11b−" cells are said to be negative for CD11b cell surface expression. "CD11c+" cells are said to express CD11c on the cell surface. "CD14−" cells are said to be negative for CD14 cell surface expression. "CD16−" cells are said to be negative for CD16 cell surface expression and "HLA-DR+" cells are said to express HLA-DR on the cell surface. In the present invention the cell surface phenotype is characterized by the presence or absence of surface cell markers. The mentioned surface cell markers represent human markers. Included in this invention are nevertheless also orthologous markers that are functionally equivalent to the mentioned human markers.

"Mammal", as used herein, refers to any member of the class Mammalia, including, without limitations, humans and nonhuman primates such as chimpanzees and other apes and monkey species; farm animals such as cattle, sheep, pigs, goats, lamas and horses; domestic mammals such as dogs and cats; laboratory animals including rodents such as mice, rats, and guinea pigs, and the like. The term does not denote a particular age or sex. Thus, adult and newborn subjects, as well as fetuses, whether male or female, are intended to be included within the scope of this term. The terms "patient", "individual" and "subject" are used interchangeably herein, and cover mammals including humans.

"Tumor" or "tumor tissue", as used herein, refers to all cells with neoplastic cell growth and proliferation, whether malignant or benign, and to tumor-associated cell. Tumor refers to the tumor tissue as a whole, including different cell types that are present in the tumor environment. Tumor tissue includes cancer cells but also non-transformed host cells, or tumor-associated cells, such as tumor-associated stroma cells. Examples of tumor-associated cells include TADCs and tumor-associated macrophages (TAMs). Tumor may be any type of cancer including but not limited to solid tumors. A solid tumor may be a cancerous tumor including, but not limited to, the ones occurring in the mammals prostate, stomach, liver, spleen, pancreas, colon, kidney, gall bladder, ovary, testicle, penis, rectum, lung, trachea, breast, heart, brain, thyroid, parathyroid, pituitary, thymus, muscle, head, neck, skin, retina, uvea, conjunctiva, salivary gland, adrenal gland, throat, esophagus, sweat glands and sebaceous glands.

A "resected tumor", as used herein refers to a tumor that was previously surgically removed. Resection may refer to the surgical removal of all of the cancerous tissue that is visible. A resected tumor is therefore obtained post-surgically, i.e. after the tumor is removed by surgery. Tumor resection includes resection of primary and secondary tumors. Resection may also refer to the removal of part of the tumor, by methods such as but not limited to biopsy. The partly resected tumor is therefore obtained post-surgically, i.e. after part of the tumor is removed by biopsy.

A "resected tumor-draining lymph node", as used herein refers to a tumor-draining lymph node that was previously surgically removed. Surgical removal can refer to lymphadenectomy, which means lymph node dissection of one or more groups of lymph nodes. Surgical removal can also refer to biopsy.

"Metastasis", as used herein refers to the process in which cancer cells originating in one organ or part of the body relocate to another part of the body and continue to replicate. Metastasized cells can subsequently form tumors which might further metastasize. Metastasis thus refers to the spread of cancer, from the part of the body where it originally occurred, to other parts of the body.

"Treatment" and "treating," as used herein refer to both therapeutic treatment and prophylactic or preventative measures, wherein the objective is to inhibit or slow down (lessen) the targeted disorder (e.g. cancer) or symptom of the disorder, or to improve a symptom, even if the treatment is partial or ultimately unsuccessful. Those in need of treatment include those already diagnosed with the disorder as well as those prone or predisposed to contract the disorder or those in whom the disorder is to be prevented. For example, in tumor (e.g. cancer) treatment, a therapeutic agent can directly decrease the pathology of tumor cells, or render the tumor cells more susceptible to treatment by other therapeutic agents or by the subject's own immune system.

A first aspect of the present invention relates to an isolated TADC subset of pre-cDC origin, essentially devoid of Mo-DCs, wherein said TADC subset is obtained from a resected tumor or a resected tumor-draining lymph node of a mammal, for use in treatment of tumor metastasis in said mammal. Therefore, specific embodiments of the isolated TADC subset include (a) the derivation of said TADC subset from pre-cDCs, (b) the virtual absence of Mo-DCs and (c) the collection of the TADC subset from a tumor or a tumor-draining lymph node after resection of said tumor or tumor-draining lymph node. An isolated TADC subset of pre-cDC origin, as used herein, can mean one or more TADC subsets of pre-cDC origin. Preferably, said TADC subset comprises one TADC subset. Alternatively, said TADC subset may comprise several TADC subsets/a mix of TADC subsets of pre-cDC origin. The tumor-derived DC subsets of interest may be from a resected tumor or a resected tumor-draining lymph node, whereas the isolation of the TADC subset from said tissues is done after surgical resection of the tumor or tumor-draining lymph node. In a preferred embodiment, the TADCs of interest include cells of mammalian origin, more preferably of human origin.

TADC subsets may be isolated, for example, by standard isolation techniques. In some embodiments, the TADC subsets may be isolated from the resected tumor or from the resected tumor-draining lymph node by preparation of a tumor single cell suspension. In a specific embodiment, such tumor single cell suspension may be obtained by cutting the resected tumor or the resected tumor-draining lymph node in small pieces, incubation of said pieces with digestion medium comprising collagenases and DNases, followed by density gradient centrifugation to remove cell debris and dead cells. A non-limiting example of a technique for isolation of TADCs and/or TADC subsets can be found in Laoui et al., 2014, hereby incorporated by reference.

TADC subsets, e.g. from tumor single cell suspensions, may be enriched, for example, by MACS and/or FACS. In some embodiments, a TADC subset is enriched such that the tumor-derived DC subset represents at least about 80%, at least about 85%, at least about 90%, at least about 95%, at least about 96%, at least about 97%, at least about 98% or at least about 99% of the total cell content of the cell preparation. According to the invention, the isolated TADC subset is essentially devoid of Mo-DCs. The TADC subset as described above may contain several TADC subsets, i.e. a mix of TADC subsets. In some embodiments, a mix of TADC subsets is enriched such that the mix of tumor-derived DC subsets represents at least about 80%, at least about 85%, at least about 90%, at least about 95%, at least about 96%, at least about 97%, at least about 98% or at least about 99% of the total cell content of the cell preparation. According to the invention, the isolated mix of TADC subsets is essentially devoid of Mo-DCs. In some embodiments, the different TADC subsets may be enriched separately and mixed after enrichment. In alternative embodiments, the different TADC subsets may be enriched in the same enrichment procedure.

According to particular embodiments, the TADC subset as described herein above comprises 1% or less Mo-DCs, i.e. the isolated subset does not contain more than 1% Mo-DCs. The level of contamination typically will be evaluated by flow cytometry analysis.

According to particular embodiments, the isolated TADC subset as described above is characterized by a phenotype that is positive for the MHC class II cell surface antigen HLA-DR) and surface antigen CD11c and negative for surface antigens CD16, BCDA2 and CD14. In further particular embodiments, said TADC subset is further characterized by a phenotype that is positive for surface antigen BDCA3 (blood dendritic cell antigen 3) and negative for surface antigens BDCA1 (blood dendritic cell antigen 1) and CD11b. Said TADC subset, with the cell surface phenotype CD16− CD11c+ HLA-DR+ BDCA2− CD14− BDCA1− BDCA3+ CD11b−, is herein further called "cDC1" subset.

According to particular embodiments, the isolated TADC subset as described above is characterized by a phenotype that is positive for the MHC class II cell surface antigen HLA-DR and surface antigen CD11c and negative for surface antigens CD16, BCDA2 and CD14 and further characterized by a phenotype that is negative for surface antigen BDCA3 and positive for surface antigens BDCA1 and CD11b. Said TADC subset, with the cell surface phenotype CD16− CD11c+ HLA-DR+ BDCA2− CD14− BDCA1+ BDCA3− CD11b+, is herein further called "cDC2" subset. BDCA3 and interferon regulatory factor 8 (IRF8) are equivalently good markers to define the cDC1 subset versus the cDC2 subset and can be used interchangeably.

According to specific embodiments, said "cDC1" subset is particularly useful for treating metastasis in a mammal having cancer. In further particular embodiments, the cDC1 subset may be used for treating metastasis in mammals having tumors that are sensitive to cytotoxic T lymphocytes (CTLs). Non-limiting examples of such CTL-sensitive tumors include melanoma, non-small cell lung carcinoma (NSCLC), colon carcinoma and microsatellite instable tumors such as uro-digestive tumors.

According to specific embodiments, said "cDC2" subset is particularly useful for treating metastasis in a mammal having cancer. In further particular embodiments, the cDC2 subset may be used for treating metastasis in mammals having tumors with a strong immunosuppressive myeloid compartment. A non-limiting example of a tumor with a strong immunosuppressive myeloid compartment is breast carcinoma.

According to a specific embodiment, the TADC subsets as described above may be obtained by a procedure which includes (a) the preparation of TADCs from a previously resected tumor or tumor-draining lymph node of a mammal and (b) the purification of TADC subsets from said TADC preparation, in order to achieve a TADC sub-population that is almost devoid of Mo-DCs. According to particular embodiments, said procedure may employ buoyant density centrifugation, immunomagnetic selection and/or depletion and fluorescently activated cell sorting (FACS). Those methods are non-limiting and can be combined. It should be noted that any of a variety of isolation methods known to those of skill in the art may be used to achieve enrichment of the TADC subset, examples of which are provided above.

The present invention pertains to pharmaceutical compositions comprising the TADC subset described herein, also referred to as "active ingredient", and a pharmaceutically acceptable carrier or excipient for use in treatment of tumor metastasis. These compositions can be utilized to achieve the desired pharmacological effect by administration to a subject in need thereof. A pharmaceutically acceptable carrier is preferably a carrier that is relatively non-toxic and innocuous to a subject at concentrations consistent with the effective amount of the active ingredient so that any side effects ascribable to the carrier do not vitiate the beneficial effects of the active ingredient. A pharmaceutically effective amount of the active ingredient is preferably that amount which produces a result or exerts an influence on the particular condition being treated. Typically said pharmaceutical compositions may comprise one TADC subset. Said pharmaceutical compositions may comprise several/a mix of TADC subsets.

The present invention also provides a method of treating tumor metastasis in a mammal, wherein the method comprises the administration of an isolated TADC subset, which was obtained from the same mammal, and which is further characterized as (a) originating from pre-cDCs, (b) lacking Mo-DCs, and (c) being isolated from a previously resected tumor or tumor-draining lymph node.

The isolated TADC subset or the pharmaceutical composition comprising the TADC subset of the present invention can be used to treat metastasis of cancer such as but not limited to melanoma. In particular embodiments, the isolated TADC subset "cDC1" or the pharmaceutical composition comprising the TADC subset "cDC1" can be used to treat CTL-sensitive tumors, such as but not limited to melanoma, NSCLC, colon carcinoma and microsatellite instable tumors.

In other embodiments the isolated TADC subset "cDC2" or the pharmaceutical composition comprising the TADC subset "cDC2" can be used to treat tumors that are characterized by the presence of a high amount of immunosuppressive myeloid cells, such as but not limited to breast carcinoma.

In various embodiments, the isolated TADC subset or the pharmaceutical composition comprising the TADC subset are administered in an amount sufficient to induce an immune response against the antigens (e.g. a T cell response). Other embodiments of the present invention provide for methods of treating cancers (e.g. melanoma, breast cancer) using the isolated TADC subset as described above or the pharmaceutical composition comprising the TADC subset as described above. In one embodiment, the method of treating cancer comprises administering an isolated TADC subset or the pharmaceutical composition comprising the TADC subset as described herein to a mammal. In one embodiment, the method of treating cancer comprises administering an isolated TADC subset or the pharmaceutical composition comprising the TADC subset as described herein to a human patient. Other embodiments provide for methods of treating metastasis of cancers such as melanoma, NSCLC, colon carcinoma, microsatellite instable tumors or breast cancer. In one embodiment, the isolated TADC subset or the pharmaceutical composition comprising the TADC subset can comprise autologous DCs. DCs suitable for use in the vaccination methods disclosed herein can be isolated or obtained from the tumor tissue in which such cells are found.

The isolated TADC subset or the pharmaceutical composition comprising the TADC subset can be administered in conjunction with other therapeutic treatments; for example, including but not limited to, chemotherapy, immunotherapy and/or radiation. The isolated TADC subset or the pharmaceutical composition comprising the TADC subset can be administered by injection via the intradermal, intra-arterial, subcutaneous, intramuscular, intravenous, intralymphatic or intranodal routes. In other embodiments, the inventive isolated TADC subset or the pharmaceutical composition comprising the TADC subset are administered directly into or in close proximity of the tumor or directly into or in close proximity of the site of the resected tumor. The isolated TADC subset or the pharmaceutical composition comprising the TADC subset can be administered one or more times to a mammal to impart beneficial results. The isolated TADC subset or the pharmaceutical composition comprising the TADC subset can be administered post-surgically, i.e. after resection of the tumor. One skilled in the art will be able to determine the appropriate timing for administering the isolated TADC subset or the pharmaceutical composition comprising the TADC subset. The timing of the first and/or subsequent dose(s) of the isolated TADC subset or the pharmaceutical composition comprising the TADC subset can depend on a variety of factors, including, but not limited to a mammals health, stability, age, and weight. The isolated TADC subset or the pharmaceutical composition comprising the TADC subset can be administered at any appropriate time interval; for example, but not limited to, once per week, once every two weeks, once every three weeks, once per month. In one embodiment, the isolated TADC subset or the pharmaceutical composition comprising the TADC subset can be administered indefinitely. In one embodiment, the isolated TADC subset or the pharmaceutical composition comprising the TADC subset can be administered three times in two week intervals. The isolated TADC subset or the pharmaceutical composition comprising the TADC subset can be prepared and frozen for later use or the isolated TADC subset or the pharmaceutical composition comprising the TADC subset can be prepared for immediate use. Appropriate dosages of the isolated TADC subset or the pharmaceutical composition comprising the TADC subset depends on a variety of factors, including, but not limited to, a mammals health, stability, age, and weight. In one embodiment, the isolated TADC subset or the pharmaceutical composition comprising the TADC subset includes from about $10^4$ to about $10^6$ TADCs. In another embodiment, the isolated TADC subset or the pharmaceutical composition comprising the TADC subset includes about $10^6$ to about $10^7$ TADCs. In another embodiment, the isolated TADC subset or the pharmaceutical composition comprising the TADC subset includes about $10^7$ TADCs.

According to a further aspect, a pharmaceutical composition is provided comprising the TADC subset of pre-cDC origin and essentially pure regarding the presence of Mo-DCs, wherein said TADC subset is obtained post-surgically from a resected tumor or tumor-draining lymph node. It is envisaged herein that the pharmaceutical composition is provided for the treatment of tumor metastasis in a mammal. Said mammal is the same mammal from which the TADC subset was isolated.

In another aspect, a method of treating tumor metastasis in a mammal is provided, the method comprising the administration of a TADC subset or a pharmaceutical composition comprising said TADC subset to said mammal, whereas (a) the TADC subset derives from pre-cDCs, (b) the TADC subset does not contain Mo-DCs, (c) the TADC subset is isolated from a resected tumor or a resected tumor-draining lymph node.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Materials and Methods to the Examples

Mice, Cell Lines and Tumor Models

Female Balb/c, CD45.2 and CD45.1 C57BL/6 mice were from Janvier. Ubiquitin-GFP mice were purchased from Jackson. Csf2rb$^{-/-}$, Flt3l$^{-/-}$, Ccr2$^{-/-}$ and MMTV-PyMT mice were provided by Melanie Greter (University of Zurich, Germany), Bart Lambrecht (UGent, Belgium), Frank Tacke (Aachen University, Germany) and Massimiliano Mazzone (KULeuven, Belgium) respectively. All procedures followed the guidelines of the Belgian Council for Laboratory Animal Science.

LLC was purchased from the ATCC cell biology collection. 3LL-R and 3LL-S cells were generated in house from C57BL/6 Lewis Lung carcinoma as previously described (Remels and De Baetselier, 1987). LLC-OVA, MC38, B16-OVA and T241 cells were kind gifts of Dmitry Gabrilovich (The Wistar Institute, Philadelphia, USA), Massimiliano Mazzone (VIB-KULeuven, Leuven, Belgium), Karine Breckpot (Vrije Universiteit Brussel, Brussels, Belgium) and Lena Claesson-Welsh (University of Uppsala, Uppsala, Sweden) respectively.

LLC-OVA, 3LL-R and 3LL-S cell lines were maintained in Roswell Park Memorial Institute-1640 medium (RPMI; Sigma) supplemented with 10% (v/v) heat-inactivated fetal calf serum (FCS; Gibco), 300 µg/ml L-glutamine (Gibco), 100 units/ml penicillin and 100 µg/ml streptomycin (Gibco) and monthly tested for the presence of *mycoplasma*. For MC38, B16-OVA and T241 cultures, RPMI was replaced by Dulbecco's Modified Eagle Medium (DMEM, Sigma). LLC, LLC-OVA, 3LL-R, 3LL-S lung carcinoma cells, MC38 colon carcinoma cells, B16-OVA melanoma cells and T241 ficrosarcoma cells were harvested and single cell suspensions of $3 \times 10^6$ in 200 µl of PBS were injected subcutaneously into the right flank of syngeneic C57Bl/6 mice. Female MMTV-PyMT mice develop mammary tumors spontaneously.

For ex-vivo TADC and T-cell cultures, this medium was supplemented with 1 mM non-essential amino acids (Invitrogen), 1 mM sodium pyruvate (Invitrogen) and 0.02 mM 2-mercapto ethanol (Invitrogen).

For intrathoracic 3LL-R injections, $5 \times 10^5$ 3 LL-R carcinoma cells were harvested and resuspended together with 25 µg Matrigel in 50 µl PBS. Cell suspensions were kept on ice until injection. Mice were anesthetized and placed in the left lateral decubitus position. One-ml tuberculin syringes with 30-gauge hypodermic needles were used to inject the cell inoculum percutaneously into the right lateral thorax, at the lateral dorsal axillary line, approximately 1.5 cm above the lower rib line just below the inferior border of the scapula. The needle was quickly advanced 6 mm into the thorax and was quickly removed after the injection. After tumor injection, the mouse was turned to the right lateral decubitus position. At day 7, mice were sacrificed and lung tissue and lung tumors were removed.

For trans-anal rectal cancer injections, mice were anesthetized with a 1/10 Nembutal dilution. The anal orifice was gently enlarged with a blunt-tipped forceps. In case of feces present, the colon was rinsed with saline using a flexible catheter. MC38 cells were injected submucosally into the distal posterior rectum at concentrations of $2.5 \times 10^5$ per 50 µl PBS with a 29-gauge syringe. After the injection, the syringe was kept in position for a few seconds, to prevent back flow. After 4 weeks, mice were sacrificed and tumors were carefully removed.

Tumor volumes were determined by caliper measurements and calculated using the formula: $V=\pi \times [d^2 \times D]/6$, where d is the minor tumor axis and D is the major tumor axis. Lung cancer and colorectal cancer patients We enrolled four non-small-cell lung carcinoma (NSCLC) patients that were not subjected to neo-adjuvant chemotherapy, including 2 males (68 and 67 years of age) with pT2aN1M0 (stage IIA) spinocellular carcinoma and cT1bN0M0 (stage IA) carcinoma and 2 females (67 and 59 years of age) with pT2aN0M0 (stage IB) adenocarcinoma and pT2aN1M0 (stage IIA) spinocellular carcinoma. The four colorectal cancer patients enrolled were not subjected to chemotherapy and included 3 males (71 and 62 years of age) with pT3N0 adenocarcinomas, one male with (79 years of age), with stage I T2MONO adenocarcinoma, and one female (49 years of age) with stage IV adenocarcinoma. All protocols were approved by the Ethics Committee of the University Hospitals Gasthuisberg (Leuven, Belgium), and all subjects gave written informed consent before study participation.

Tumor, Lymph Node, Bone Marrow and Spleen Preparation, Flow Cytometry and Cell Sorting Tumors were excised, cut in small pieces, treated with 10 U/mL collagenase I, 400 U/mL collagenase IV, and 30 U/mL DNaseI (Worthington) for 30 min at 37° C., squashed and filtered. Red blood cells were removed using erythrocyte lysis buffer and density gradients (Axis-Shield) were used to remove debris and dead cells.

Tumor-draining lymph nodes (LN) were cut, dissociated with 10 U/mL collagenase I, 400 U/mL collagenase IV, and 30 U/mL DNaseI (Worthington) for 45 min at 37° C. and filtered.

Spleens were flushed with 200 U/mL collagenase III (Worthington) and left for 30 min at 37° C. Afterwards, spleens were filtered and red blood cells were removed using erythrocyte lysis buffer.

To purify DC subpopulations from tumor, spleen or LN, CD11c+ cells were MACS-enriched (antiCD11c microbeads, Miltenyi) and sorted using a BD FACSAria II (BD Biosciences).

Bone marrow (BM) leukocytes were isolated through flushing of tibia and femur. The obtained cell suspensions were filtered, red blood cells were removed using erythrocyte lysis buffer. To purify BM monocytes, CD11b$^+$ cells were MACS-enriched (antiCD11b microbeads, Miltenyi) before sorting.

Commercial antibodies for cell surface stainings are listed in Table 1. To prevent aspecific binding, cells were pre-incubated with rat anti-mouse CD16/CD32 (clone 2.4G2, BD Biosciences).

Normalized delta-Median Fluorescence Intensity (ΔMFI) was calculated as: [(MFI staining)–(MFI isotype staining)]/(MFI staining). FACS data were acquired using a BD FACSCanto II or LSRII (both from BD Biosciences) and analyzed using FlowJo (Tree Star, Inc.). To purify TADC, cells were sorted using a BD FACSAria™ II (BD Biosciences) from 9-15 pooled tumors.

Measurement of Cytokine and Chemokine Production

Cytokine and chemokine concentrations were measured by Bio-Plex (Bio-Rad), according to the supplier's protocols.

In Vitro and In Vivo Phagocytosis, DQ-OVA Processing, Mixed Leukocyte Reaction Assays and OT-I and OT-II T-Cell Activation For in vitro latex uptake, freshly isolated tumor single-cell suspensions were cultured in 96-well plates for 40 minutes at 4° C. or 37° C., in the presence of latex microspheres (Polysciences) diluted at 1:5000. Latex uptake by TADC was assessed via flow cytometry. For measuring in vivo latex uptake by TADC, tumor-bearing mice were injected IV with 250 µl of yellow-green latex microspheres (Polysciences) diluted 1:25 in PBS. 1-2 hours later, tumor single cell suspensions were made and latex uptake by TADC subpopulations was assessed via flow cytometry.

To assess TADC antigen processing, tumor single cell suspensions were incubated for 15 minutes at 0° C. or 37° C. in the presence of 10 µg/ml DQ-OVA (Molecular Probes), allowing antigen uptake. After thorough washing, cells could further process DQ-OVA intracellularly during different time intervals, at 0° C. or 37° C. Following each time interval, cells were surface labeled and DQ-OVA fluorescence in each subset was measured via flow cytometry.

For OT-I and OT-II proliferation assays, MACS sorted CD11c$^-$CD8$^+$ OT-1 and CD11c$^-$CD4$^+$ OT-2 T cells were stained with 0.2 µM CFSE (Molecular Probes, Carlsbad, Calif., USA) following the manufacturer's instructions. Purified TADC were added to 10$^5$ OT-I or OT-II T cells and stimulated with 1 µg/ml anti-CD3 and 2 µg/ml CD28 for a positive control. To inhibit iNOS the cocultures were supplemented with 5 µM L-NMMA (NG-monomethyl-L-arginine, Alexis Biochemicals). After 72 h of co-incubation, proliferation of T cells was measured via CFSE dilution using flow cytometry.

Adoptive Pre-cDC and Monocyte Transfers

Bone marrow Ly6C$^{hi}$ monocytes and pre-cDC were labeled with CellTrace (life technologies) and sorted from CD45.2 mice. 10$^6$ Ly6C$^{hi}$ monocytes or 4×10$^5$ pre-cDC were intravenously injected in 3LL-R tumor-bearing CD45.1 mice. The fate of the CD45.2$^+$ CellTrace$^+$ progeny was determined 72 hours later.

TADC Vaccination Experiments

For vaccination experiments naive C57BI/6 mice were subcutaneously injected with 10$^4$ TADC of a specific subset, 6 and 3 weeks prior to subcutaneous LLC-OVA or B16-OVA inoculation. TADC were sorted from a pool of 10 to 12 LLC-OVA tumor bearing-mice or B16-OVA tumor bearing-mice. Mice vaccinated subcutaneously with 100 µg OVA protein in 100 µl CFA were used as positive controls.

RNA Extraction, cDNA Preparation and Quantitative Real-Time PCR

These experiments were performed as described before (Movahedi et al., 2010). RNA was extracted using TRIzol (Invitrogen) and was reverse-transcribed with oligo(dT) and SuperScript II RT (Invitrogen). Quantitative real-time PCR was performed in an iCycler, with iQ SYBR Green Supermix (Bio-Rad). Primer sequences are listed in Supplementary Table 2. PCR cycles consisted of 1' 94° C., 45" 55° C., 1' 72° C. Gene expression was normalized using ribosomal protein S12 (Mrps12) as a housekeeping gene. Primers are listed in Table 2. Statistics Significance was determined by the Student's t test or ANOVA followed by a post test using GraphPad Prism 6.0 software. A p-value<0.05 was considered statistically significant. All graphs show mean±SEM.

Example 1. Distinct Tumor-Associated Dendritic Cell Subpopulations Derive from Different Precursors To delineate the relative abundance of distinct tumor-associated DC (TADC) populations in solid tumors, we first employed the 3LL-R Lewis Lung Carcinoma model which is known to be strongly infiltrated by myeloid cells (Laoui et al., 2014). These tumors contain a sizeable population of $CD3^{neg}$ $CD19^{neg}$ $Ly6G^{neg}$ $CD11C^{hi}$ $MHC-II^{hi}$ TADC (FIG. 1A). Earlier studies characterized distinct DC populations based on their differential expression of CD24, CD11b, Ly6C and CD64 (Langlet et al., 2012). Using this approach, three discrete TADC subsets were clearly distinguishable (FIG. 1A): $Ly6C^{lo}$ $CD64^{lo}$ $CD24^+$ $CD11b^{lo}$ conventional TADC (cDC1, gate 1), $Ly6C^{lo}$ $CD64^{lo}$ $CD24^{int-lo}$ $CD11b^+$ conventional TADC (cDC2, gate 2) and $Ly6C^{hi}$ $CD64^{hi}$ $CD24^{int}$ $CD11b^+$ monocyte-derived TADC (Mo-DC, gate 3). This situation is similar to what has been reported in several non-cancerous tissues (Guilliams et al., 2010).

We further assessed the origin of TADC subsets by adoptive transfer of pre-cDCs and monocytes in 3LL-R tumor-bearing mice. When adoptively transferring sorted $CD45.2^+$ $B220^-$ $CD11c^+$ $Sirp\alpha^{int}$ $CellTrace^+$ bone marrow pre-cDC precursors (Scott et al., 2015) in 3LL-R tumor-bearing $CD45.1^+$ recipient mice, only $Ly6C^{lo}$ $CD64^{lo}$ $CD24^+$ $CD11b^{lo}$ and $Ly6C^{lo}$ $CD64^{lo}$ $CD24^{int-lo}$ $CD11b^+$ cells could be retrieved from tumors after 72 h (FIG. 1B). Importantly, none of the transferred pre-cDC precursors differentiated into $CD64^{hi}CD11b^+$ cells during this time span. In contrast, transferred $CD45.2^+$ $CD11b^+$ $Ly6G^-$ $Ly6C^+$ $MHC-II^-$ eFluor450$^+$ bone marrow monocytes were all retrieved as $CD64^{hi}$ $CD11b^+$ cells within the TADC gate. Note that relatively low amounts of $CD45.2^+$ Mo-DC were retrieved from tumors since most transferred monocytes gave rise to $MHC-II^{low}$ and $MHC-II^{high}$ TAM, which make up the bulk of monocyte-derived cells in 3LL-R tumors (data not shown). Altogether these data indicate that $Ly6C^{lo}$ $CD64^{lo}$ $CD24^+$ $CD11b^{lo}$, $Ly6C^{lo}$ $CD64^{lo}$ $CD24^{int-lo}$ $CD11b^+$ and $CD64^{hi}$ $CD11b^+$ cells represent cDC1, cDC2 and Mo-DCs, respectively.

Corroborating the adoptive transfer experiments, 3LL-R tumors grown in CCR2-deficient mice, in which the egression of monocytes from the BM is strongly reduced (Serbina et al., 2008), showed almost complete absence of the Mo-DC subset while cDC1 and cDC2 were unaffected (FIG. 1C). In line with their cDC ontogeny, the amounts of tumor-associated cDC1 and cDC2 were strongly reduced in both Flt3L-KO and GM-CSFR-KO mice, showing their dependence on both of these growth factors (FIG. 1C). The residual presence of cDC2 in tumors in both KO strains suggests that their generation and/or survival may depend on the simultaneous functioning of (other) hematopoietic growth factors in the tumor microenvironment (Kingston et al., 2009). Importantly, also Mo-DC were heavily affected by the absence of Flt3L and the inability to respond to GM-CSF. Whether this drop in Mo-DC reflects a direct effect of Flt3L and/or GM-CSF on Mo-DC differentiation/maintenance, or whether the loss of cDC subsets in these KO tumors influences the development of Mo-DC, is not clear at present.

Following the fate mapping experiments, we further characterized the TADC subsets for markers that were reported to associate with different DC populations. In this respect, the need for IRF8 and IRF4 in the development of cDC1 and cDC2, respectively, has been established (Tamura et al., 2005). Intracellular staining for these transcription factors confirmed the higher expression of IRF4 in cDC2 and of IRF8 in cDC1 (FIG. 1D). Interestingly, Mo-DC appeared to contain relatively high levels of IRF4 and low levels of IRF8. In agreement with their monocytic origin, the Mo-DC expressed high levels of FcεR (FIG. 1D), previously associated with monocyte-derived DC (Plantinga et al., 2013). Furthermore, the Mo-DC population was also the only subset expressing the macrophage-related marker MerTK (Gautier et al., 2012; Langlet et al., 2012). Both CD103 and the cross-presentation related marker XCR1 seem to be uniquely expressed on the cDC1 subset, whereas SIRPα expression was limited to the Mo-DC and cDC2 subsets (FIG. 1D). Finally, DEC205 is expressed on all TADC subsets with Mo-DC>cDC1>cDC2 (FIG. 1D).

Figure 2:
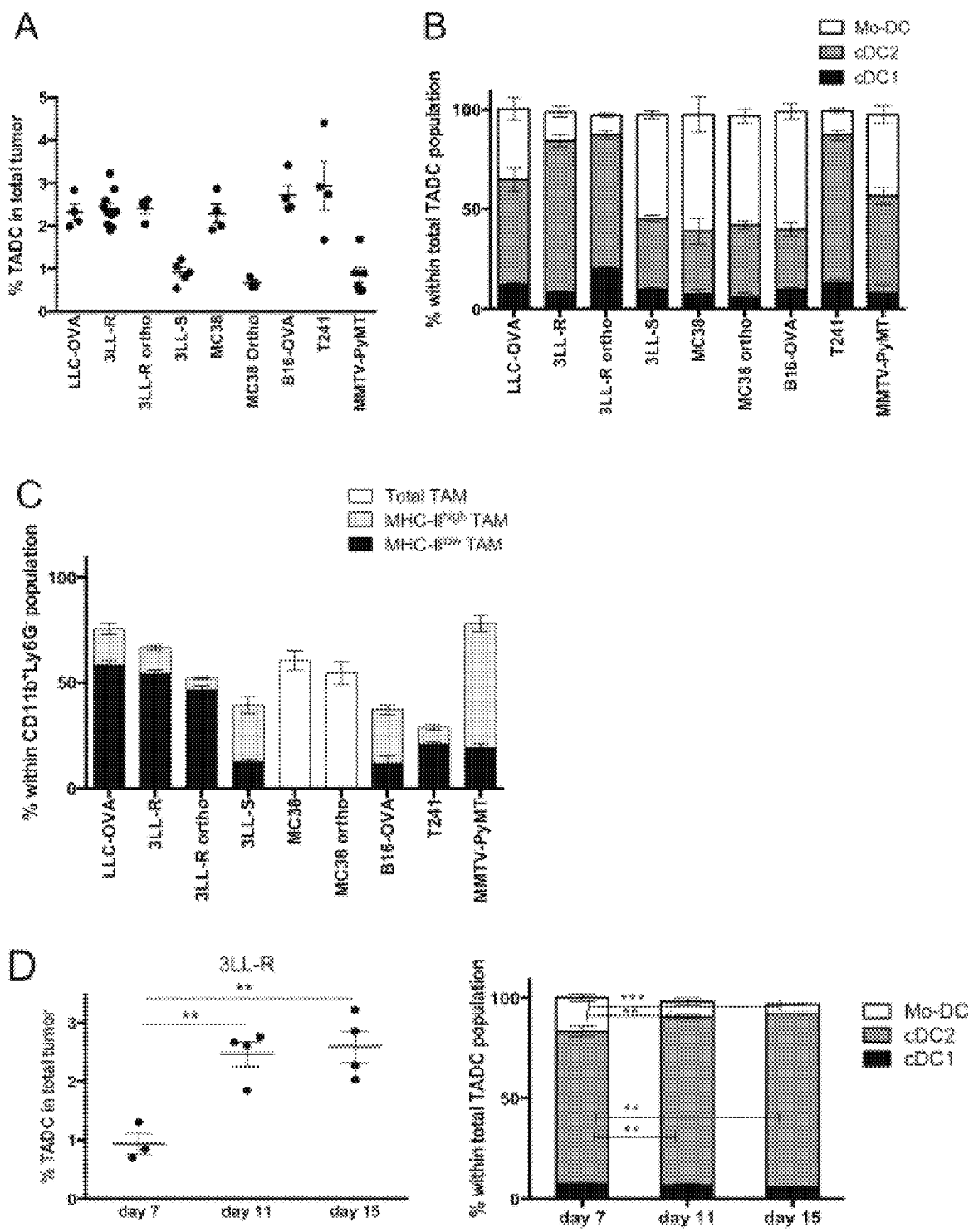
FIG. 2 shows the infiltration of several tumor types with distinct TADC subsets. (A) TADC were gated as doublets$^{neg}$ live ($AQUA^{neg}$) $Ly6G^{neg}$ $CD3^{neg}$ $CD19^{neg}$ $CD11c^{pos}$ $MHC-II^{pos}$ cells in single-cell suspensions of 20-day old subcutaneous (sc) LLC-OVA lung carcinoma, 12-day old sc 3LL-R lung carcinoma, 6-day old 3LL-R orthotopically injected lung carcinoma, 35-day old sc 3LL-S lung carcinoma, 17-day old sc MC38 colon carcinoma, 28-day old MC38 orthotopically injected colon carcinoma 20-day old B16-OVA sc melanoma, 20-day old T241 sc fibrosarcoma and 16-weeks old spontaneously grown MMTV-PyMT mammary carcinoma with tumors of similar volumes. (B) The percentage of each TADC subset within the total TADC population was determined for indicated tumors of similar volumes. (C) The percentage of each TAM subset within the total $CD11b^+$ $Ly6G^-$ population was determined for indicated tumors of similar volumes. (A-C) Graphs show mean±SEM. Results are representative of 2 independent experiments with n=3 to 10. (D-E) Amount of total TADC (D, left panel), TADC subsets (D, right panel) and TAM subsets (E) was assessed in single-cell suspensions of 7, 11 and 15 day-old 3LL-R tumors. (F-G) The percentages of total TADC (F, left panel), TADC subsets (F, middle panel) and TAM subsets (G) was assessed in single-cell suspensions of 25, 30, 37, 42 day-old 3LL-S tumors. (D-G) Graphs show mean±SEM. Results are representative of 3 independent experiments with Statistical analysis by one-way ANOVA. *, $p<0.05$; , $p<0.01$; *, $p<0.001$; ****, $p<0.0001$.
Figure 2:
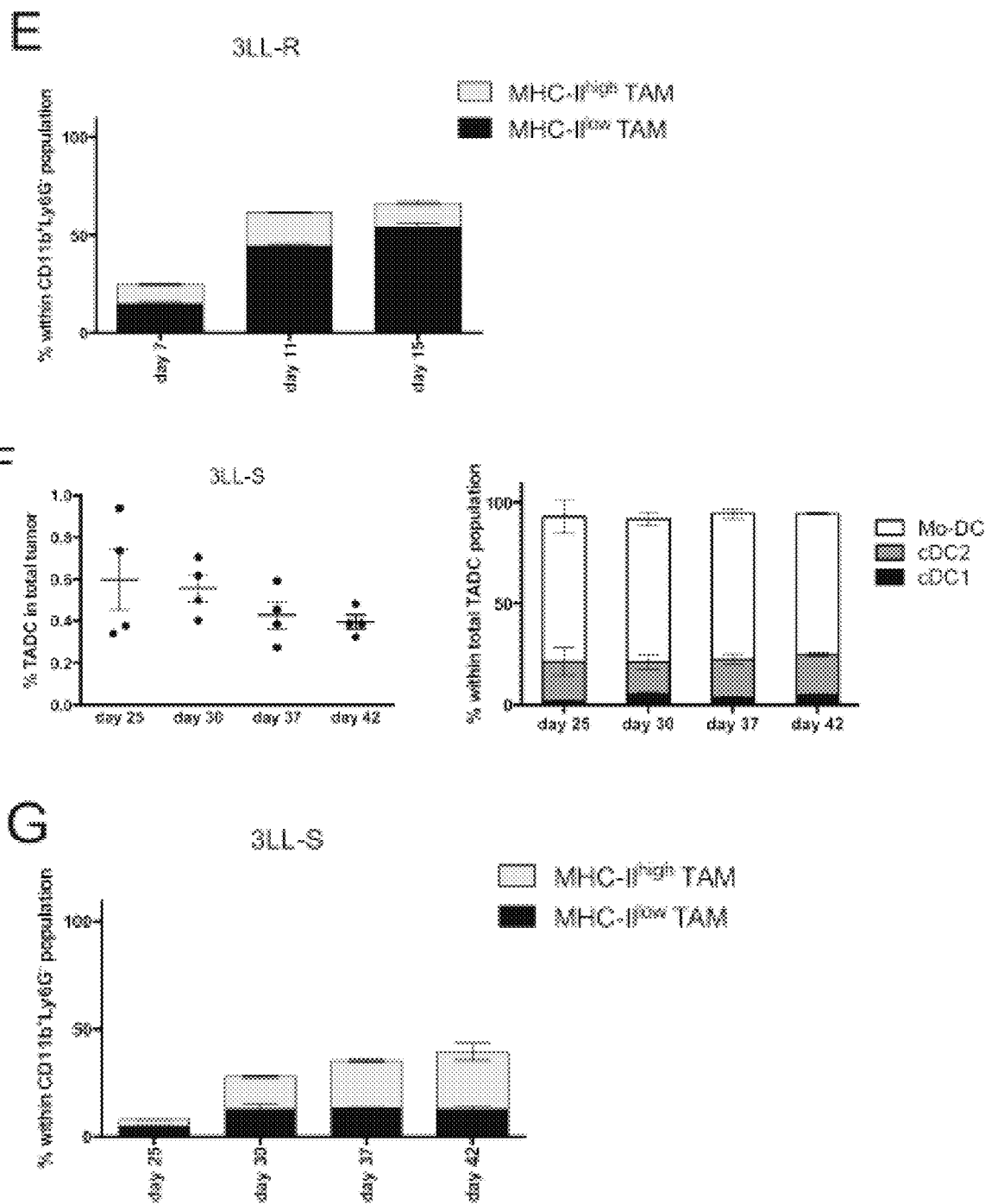

Example 2: Distinct Tumor-Associated Dendritic Cell Subpopulations are Present in Multiple Tumor Types We then assessed the presence of TADC subsets in several transplantable mouse tumor models of various histological origins and distinct genetic backgrounds and in the spontaneous MMTV-PyMT breast carcinoma model. Single cell suspensions of subcutaneously growing LLC lung carcinoma tumors, their fast progressing 3LL-R and slowly progressing 3LL-S subclones (Remels and De Baetselier, 1987), MC38 colon carcinoma, B16 melanoma and T241 fibrosarcoma, as well as 3LL-R tumors orthotopically growing in the lung parenchyma and MC38 orthotopically growing in the rectum (all in C57Bl/6 background) contained small, but clearly identifiable $CD11c^{hi}$ $MHC-II^{hi}$ TADC fractions (FIG. 2A). TADC were also retrieved from MMTV-PyMT mammary tumors in the FVB background (FIG. 2A).

When comparing the DC content of similarly sized tumors, the cDC1 were the rarest subset in all investigated models, whereas the cDC2 were always well represented (between 30.1% and 75.7% of all TADC depending on the model) (FIG. 2B). The greatest variability was seen amongst the Mo-DC, which were only poorly present in 3LL-R and T241 tumors, but form a sizeable population in LLC, MMTV-PyMT, 3LL-S, MC38 and B16 tumors, being even the dominant TADC population in the latter three models. Interestingly, the TADC content of subcutaneously versus orthotopically grown 3LL-R or MC38 tumors is very comparable, suggesting that the tumor microenvironment rather than the surrounding tissue dictates TADC heterogeneity. Notably, tumor models with a high Mo-DC content also harbor relatively more M1-like $MHC-II^{high}$ tumor-associated macrophages (TAM) as compared to their M2-like $MHC-II^{low}$ counterparts (high $MHC-II^{high}/MHC-II^{low}$ TAM ratio) (FIG. 2C), suggesting that the microenvironment in these tumors favors the differentiation of infiltrating monocytes towards these $MHC-II^{high}$ macrophages and DC. Of note, MC38 tumors, which also contain a large Mo-DC population, contain a single TAM population displaying a mixed M1-like and M2-like phenotype (FIG. 2C). The correlation between Mo-DC and $MHC-II^{high}$ TAM presence is maintained within the same tumor model, whereby an underrepresentation of $MHC-II^{high}$ TAM and a gradual accumulation of $MHC-II^{low}$ TAM in the course of tumor growth is paralleled by a reduced percentage of Mo-DC, as illustrated by the 3LL-R model (FIGS. 2D and 2E). However, the total percentage of 3LL-R-infiltrating TADC increases during tumor growth (FIG. 2D). In contrast, 3LL-S tumors are invariably dominated by $MHC-II^{high}$ TAM (within the TAM compartment) and Mo-DC (within the TADC compartment) throughout tumor growth and the percentage of TADC did not change (FIGS. 2F and 2G).

Figure 3:
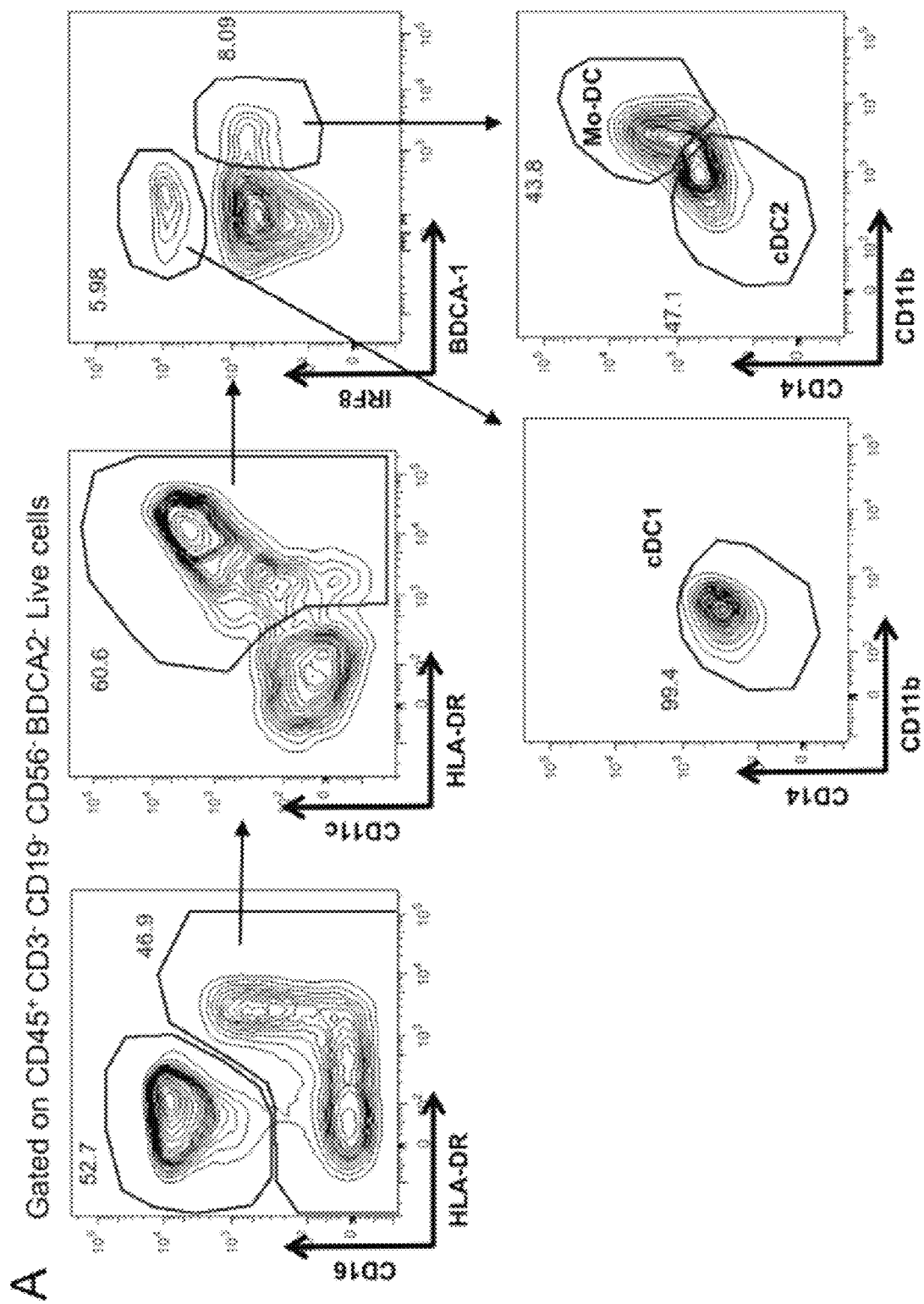
FIG. 3 shows that the presence of distinct TADC subsets can be recapitulated in human tumors. (A) Human non-small cell lung carcinoma (NSCLC) tumor biopsies were pre-gated on $CD45^+$ $CD3^-$ $CD19^-$ $CD56^-$ $BDCA2^-$ live cells and $CD16^-$ $CD11c^{high}$ $HLA-DR^+$ cells were subdivided in "cDC1" ($BDCA1^-$ $IRF8^+$ $CD14^-$ $CD11b^{low}$), "cDC2" ($BDCA1^+$ $IRF8^-$ $CD14^-$ $CD11b^+$) and "Mo-DC" ($BDCA1^+$ $IRF8^-$ $CD14^+$ $CD11b^{high}$). (B-C) The total percentage of TADC (sum of 3 subsets) (B) and the percentage of each TADC subset within the total TADC population (C) was determined for (NSCLC) and colorectal (CRC) tumors. For all experiments, graph show mean±SEM. n=4 patients per tumor type.
Figure 3:
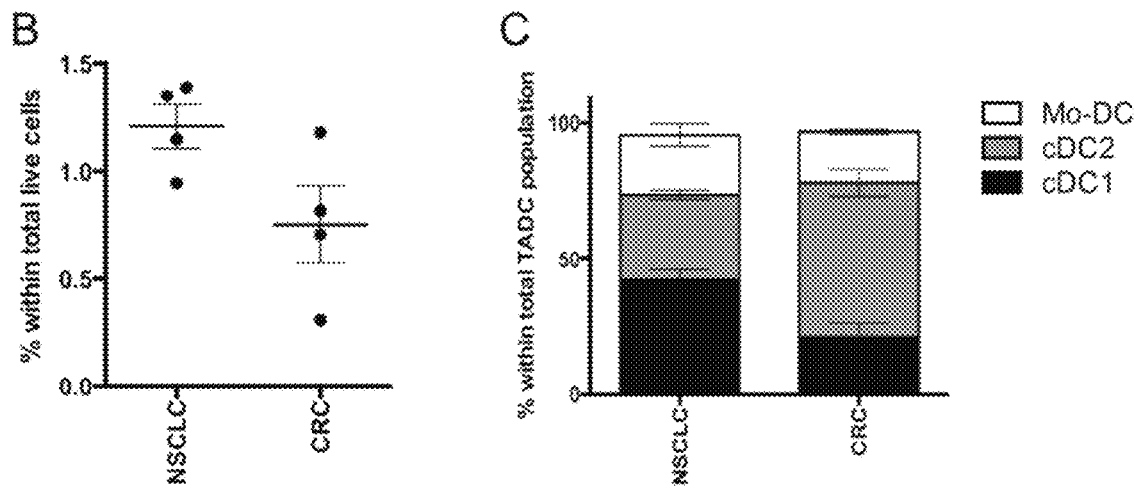

Example 3: The Presence of Distinct Tumor-Associated Dendritic Cell Subpopulations can be Recapitulated in Human Tumors To translate our original findings to the human situation, the presence of distinct TADC subpopulations was assessed in fresh tumor biopsies of lung and colorectal cancer patients. Small amounts of CD16⁻ CD11c⁺ HLA-DR⁺ TADC were retrieved from human tumors (FIGS. 3A and 3B). Importantly, this TADC compartment encompassed three distinct subsets, highly reminiscent of the murine TADC subsets. Human TADC contained a BDCA2⁻ BDCA1⁻ IRF8⁺ CD14⁻ CD11b$^{low}$ cDC1 population and a BDCA2⁻ IRF8⁻ BDCA1⁺ TADC fraction, which consisted of two subsets with differential CD14 and CD11b expression (FIGS. 3A and 3C). As previously suggested (Segura et al., 2013), these consist of a CD14⁻ CD11b⁺ cDC2 population and a CD14⁺ CD11b$^{high}$ DC population, analogous to murine Mo-DC. Of note, no BDCA2⁺ plasmacytoid DC could be retrieved.

Example 4: Mo-DC have the Highest Inherent Antigen Uptake and Processing Capacities Although the induction of potent anti-tumor immune responses has been attributed to DCs in some reports (Goc et al., 2014; Preynat-Seauve et al., 2006), TADC have also been described as tolerogenic or immunosuppressive cells with impaired antigen presenting, T-cell stimulating and migratory capacities, enabling tumor immune escape (Gabrilovich, 2004; Ma et al., 2013; Preynat-Seauve et al., 2006; Vesely et al., 2011). Hence, it could be postulated that distinct TADC subsets exert different functions. In first instance, we investigated the antigen uptake, processing and presenting capacities by the three distinct TADC populations.

Figure 4:
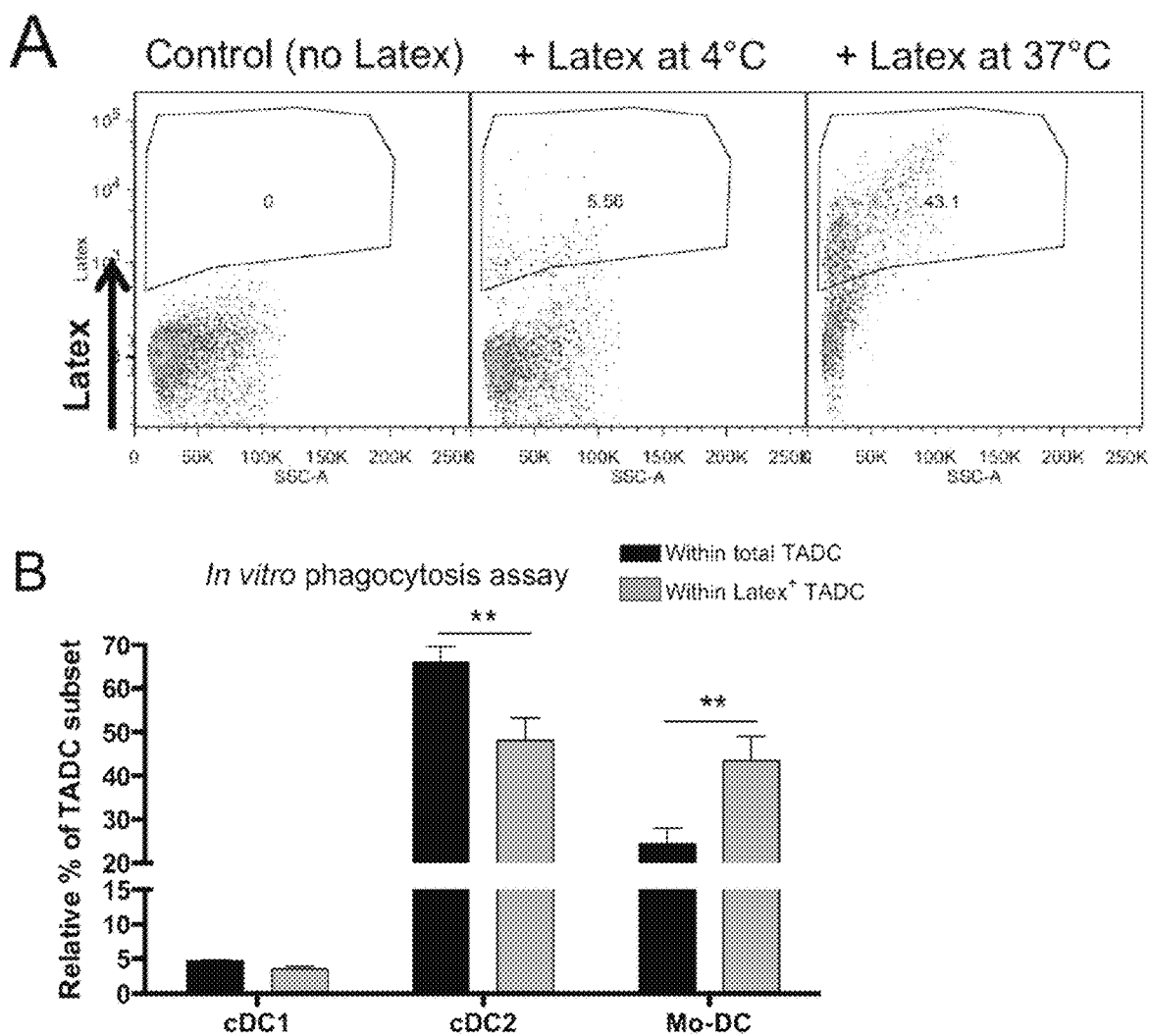
FIG. 4 shows the difference of antigen uptake, processing and presentation in the distinct TADC subsets. (A-B) In vitro phagocytosis assay. (A) Single cell suspensions of 12-day old 3LL-R tumors were cultured in vitro, in the absence (control) or presence of latex beads for 40 minutes at 4° C. or 37° C. (B) The percentage of the distinct TADC subsets within the total TADC gate or within the $Latex^+$ TADC gate are given. n=3 pools of 4 tumors. Analysis by one-way ANOVA. **, $p<0.01$. (C) In vivo phagocytosis assay. 12-day old 3LL-R tumor-bearing mice were injected intravenously with latex beads 2 hours before sacrifice. The percentage of the distinct TADC subsets within the total TADC gate or within the $Latex^+$ TADC gate are given. n=3 pools of 4 tumors. Analysis by one-way ANOVA. *, $p<0.05$; *, $p<0.001$. (D) DQ-OVA processing. 12-day old 3LL-R tumor subsets were allowed to phagocytose and process DQ-OVA for 15' at 0° C. or 37° C. Free DQ-OVA was subsequently removed from the culture medium and cells were given an additional 15, 30, 60 or 90 minutes to process internalized DQ-OVA. DQ-OVA processing results in the formation of fluorescent peptides and mean±SEM of the fluorescence intensities for the gated subsets are shown in the graph. n=3 pools of 4 tumors. Analysis by two-way ANOVA. **, $p<0.0001$. (E) Cross-presentation by the different TADC subsets in LLC-OVA was assessed by staining for the OVA-derived peptide SIINFEKL in association with MHC-I. Black line=SIINFEKL expression of TADC in LLC-OVA tumors; shaded histograms=SIINFEKL expression of TADC in LLC tumors (control). $\Delta MFI$ are indicated and represent (MFI SIINFEKL MFI control). Results are representative of 2 independent experiments with n=4.
Figure 4:
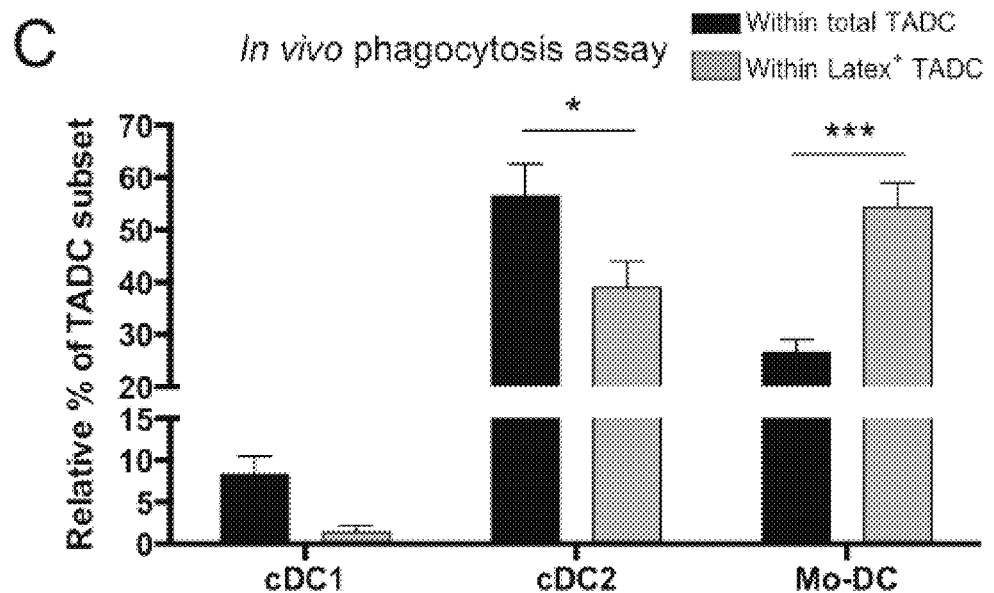
Figure 4:
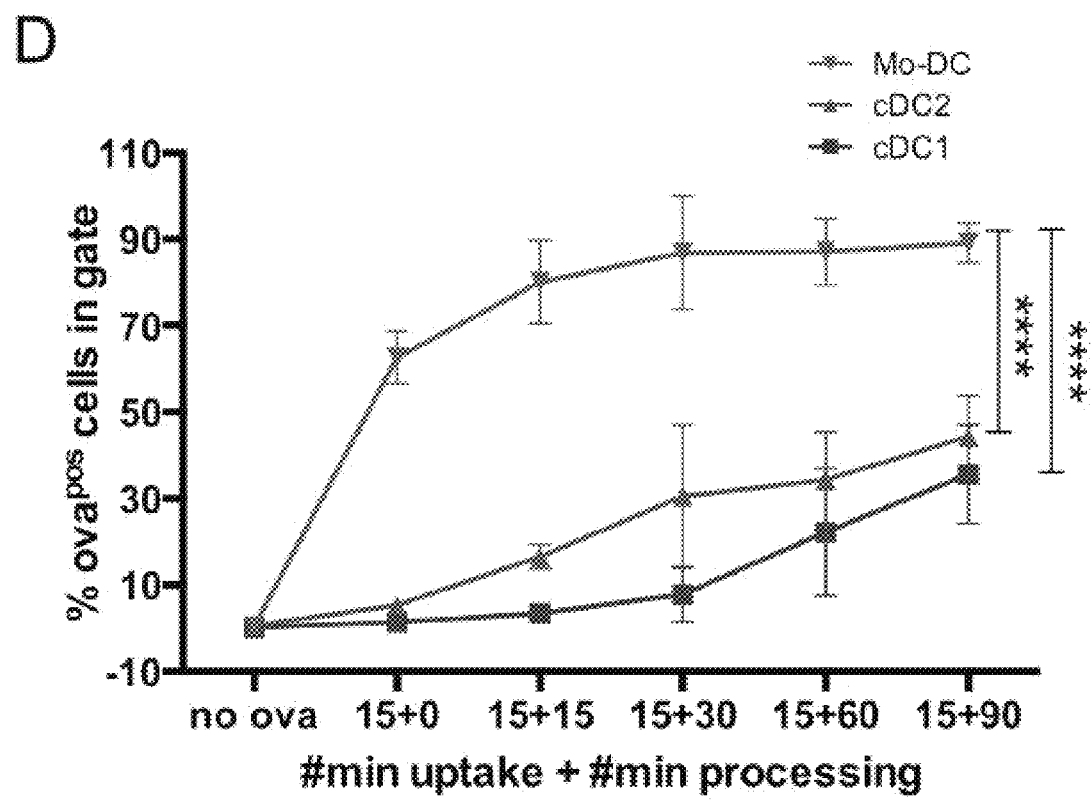
Figure 4:
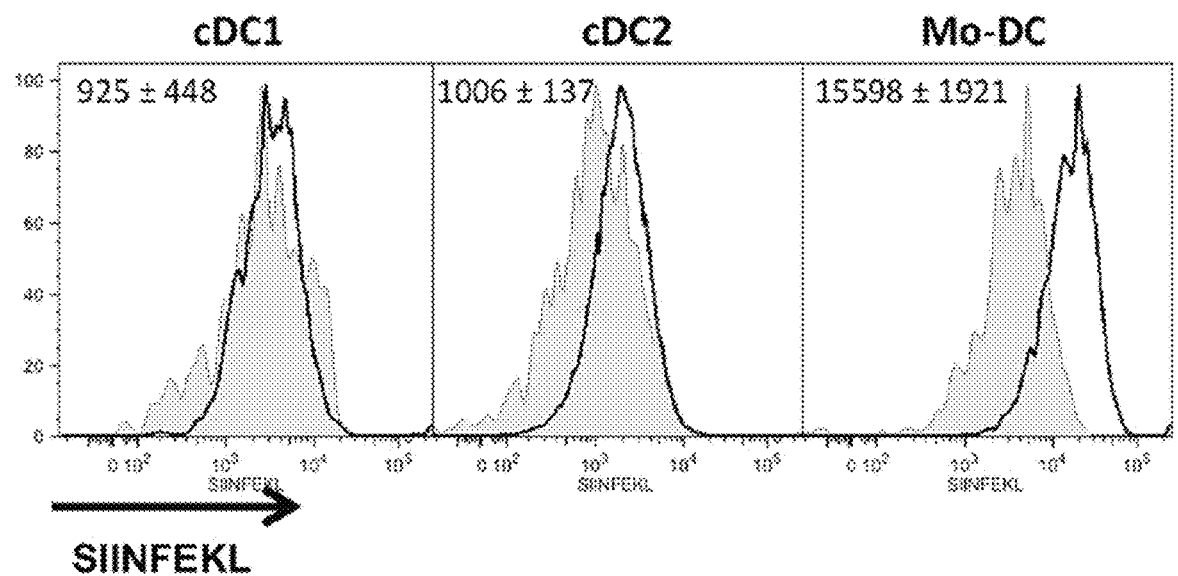

Their inherent phagocytic capacity was tested in vitro by adding fluorescent latex beads to 3LL-R tumor single cell suspensions at 37° C. (active phagocytosis) or at 4° C. (FIG. 4A). All TADC subsets were able to ingest latex beads at 37° C. However, when compared to the total TADC population, the proportion of cells within the latex⁺ TADC population only increased for the Mo-DC subset, signifying that this population was more phagocytic than both cDC types (FIG. 4B). Interestingly, when performing an in vivo phagocytosis assay by injecting fluorescent latex beads intravenously into tumor-bearing mice 2 hours before removing the tumor, the Mo-DC were again overrepresented within the latex⁺ population, corroborating their superior phagocytic capacity in vivo (FIG. 4C).

We next assessed the efficiency of antigen processing by the different TADC subsets. Hereto, 3LL-R tumor single cell suspensions were incubated with DQ-ovalbumin (DQ-OVA) for 15 minutes, allowing antigen uptake. Following thorough washing, intracellular processing was assessed at different time intervals using the fluorescence of cleaved DQ-OVA as readout. No DQ-OVA processing occurred at 0° C. (data not shown). Remarkably, the vast majority of Mo-DC rapidly processed DQ-OVA (62.7±3.5% of fluorescent cells after 15 min), while no processing had occurred in cDC1 and cDC2 at this early time point (FIG. 4D). Gradually more cDC processed DQ-OVA, with a slightly higher efficiency for cDC2 compared to cDC1 (reaching 30.5±11.6% versus 7.8±4.6% fluorescent cells after 45 min, respectively). Together, these data illustrate the competitive advantage of Mo-DC for antigen uptake and processing.

Finally, we assessed whether TADC were capable of processing OVA and cross-presenting its immunodominant CTL epitope (SIINFEKL) in vivo, by staining freshly isolated TADC subsets from LLC-OVA tumors with a mAb specific for H-2K$^b$/SIINFEKL complexes. Mo-DC showed the highest expression of these complexes, indicative of a superior antigen uptake and processing in the tumor microenvironment (FIG. 4E).

Figure 5:
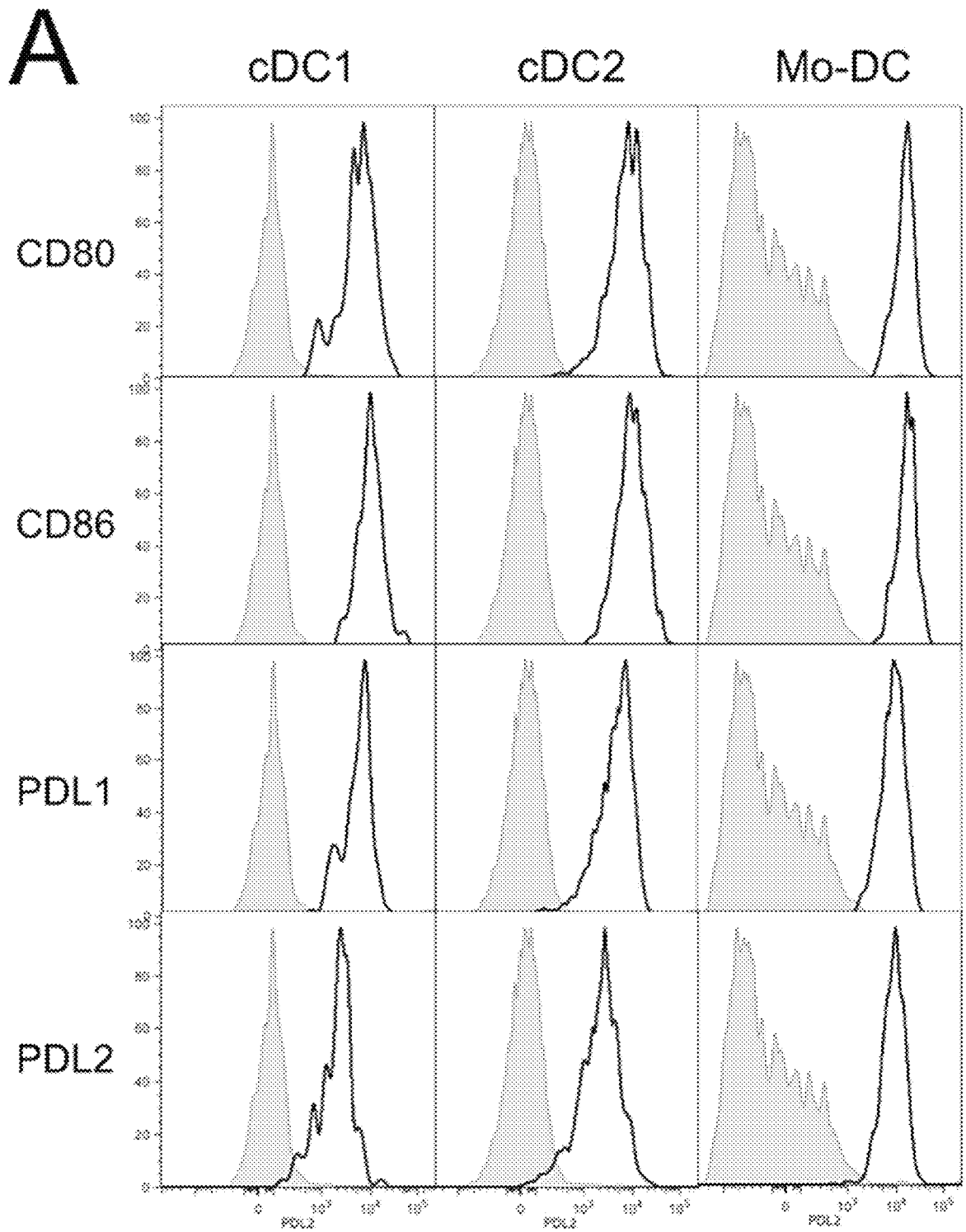
FIG. 5 shows the distinct T-cell proliferative capacities of the TADC subsets. (A) Single-cell suspensions of 12-day old 3LL-R tumors were stained for the indicated markers and histogram overlays are shown. Black line=expression of the indicated marker; shaded histogram=isotype control. Results are representative of 2 independent experiments with $n \geq 4$. (B-C) Antigen-presenting activities of TADC subsets from 3LL-R tumors in comparison with splenic $CD11c^{hi}MHC-II^{hi}B220^-Ly6C^-$ cDC from naive C57Bl/6 mice. Sorted TADC or splenic cDC were cultured in the presence of purified allogeneic BALB/c $CD4^+$ (B) or $CD8^+$ T cells (C) during 5 days and the proliferation of responding T cells was measured via $^3H$-thymidine incorporation (cpm). Results are representative of 2 independent experiments with n=3 pools of 10-12 tumors. Statistical analysis by one-way ANOVA. $p<0.001$; **, $p<0.0001$. (D-E) Sorted TADC subsets were co-cultured with OT-I (D) or OT-II (E) T cells for 3 days at a DC/T-cell ratio of 1/10. The histograms represent CFSE dilution, indicative for T-cell proliferation. Black line=non-stimulated T cells without TADC; shaded histogram=T cells in the presence of TADC. Results are representative of 3 independent experiments with n=pool of 10-12 tumors. (F) Supernatants of co-cultures of TADC subsets and OT-II T cells (DC/OT-II=1/10) were tested for the presence of IFN-γ and IL-4 by luminex. n≥4. (G) Intracellular staining on OT-II T cells cocultered with CD11b$^+$-like TADC or Mo-DC for 3 days at a DC/OT-II ratio of 1/5 was performed for the Th-inducing transcription factor RORγt. Isotype control and transcription factor staining are depicted. Results are representative of 5 independent experiments with n=pool of 8-12 tumors. Analysis by one-way ANOVA. , p<0.01. (H) Supernatants of co-cultures of TADC subsets and OT-II T cells (DC/OT-II=1/10) were tested for the presence of IL-17 by luminex. Analysis by one-way ANOVA. **, p<0.01. (I) Intracellular staining on OT-II T cells cocultered with cDC2 for 3 days at a DC/OT-II ratio of 1/5 was performed for Th-inducing transcription factors T-bet, GATA3 and FOXP3. Isotype control and transcription factor staining are depicted. (J) Supernatants of TADC subset cultured for 48 h were tested for presence of IL-6 and IL-13 by luminex. Statistical analysis by one-way ANOVA. *, p<0.05; , p<0.01; *, p<0.001; ****, p<0.0001.
Figure 5:
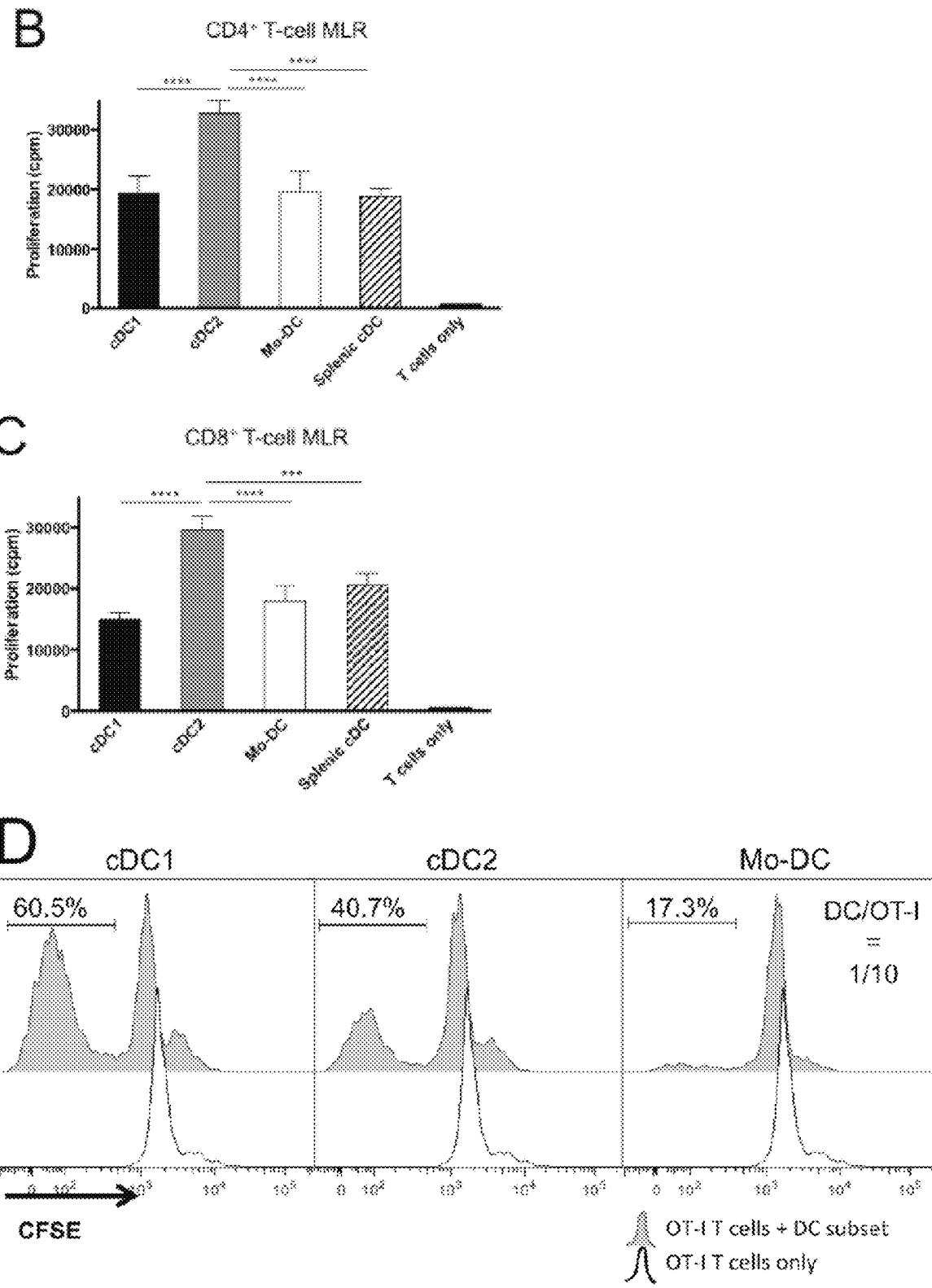
Figure 5:
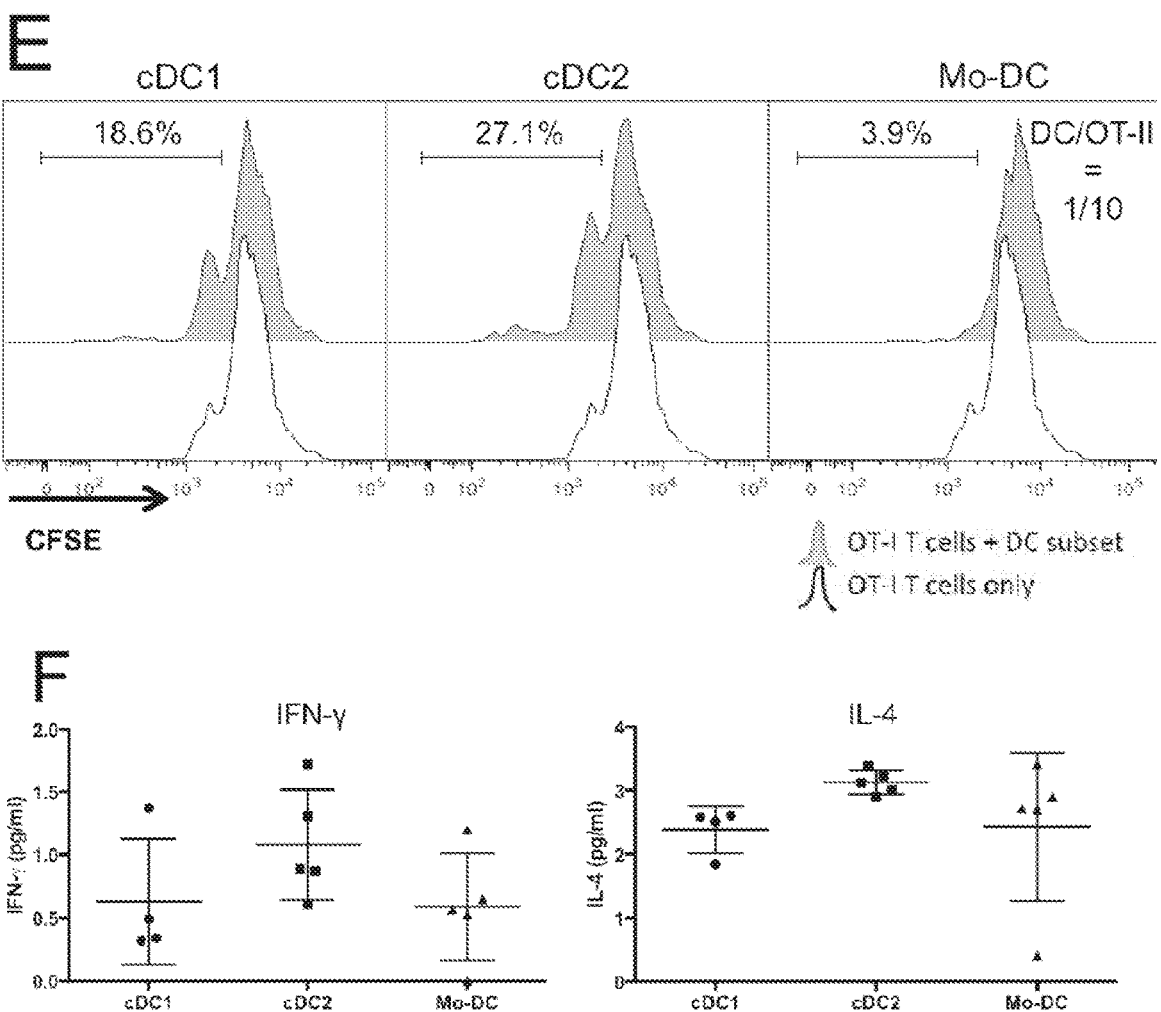
Figure 5:
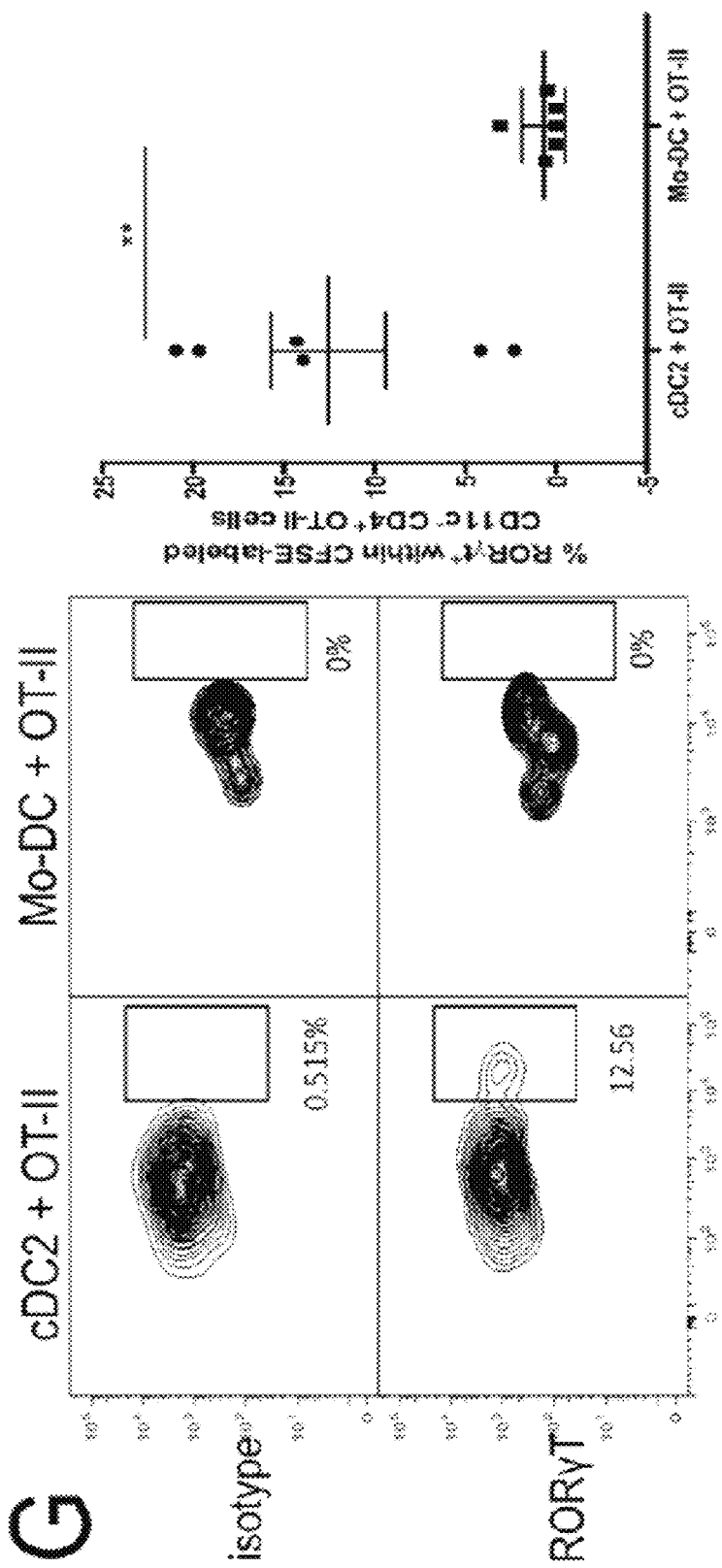
Figure 5:
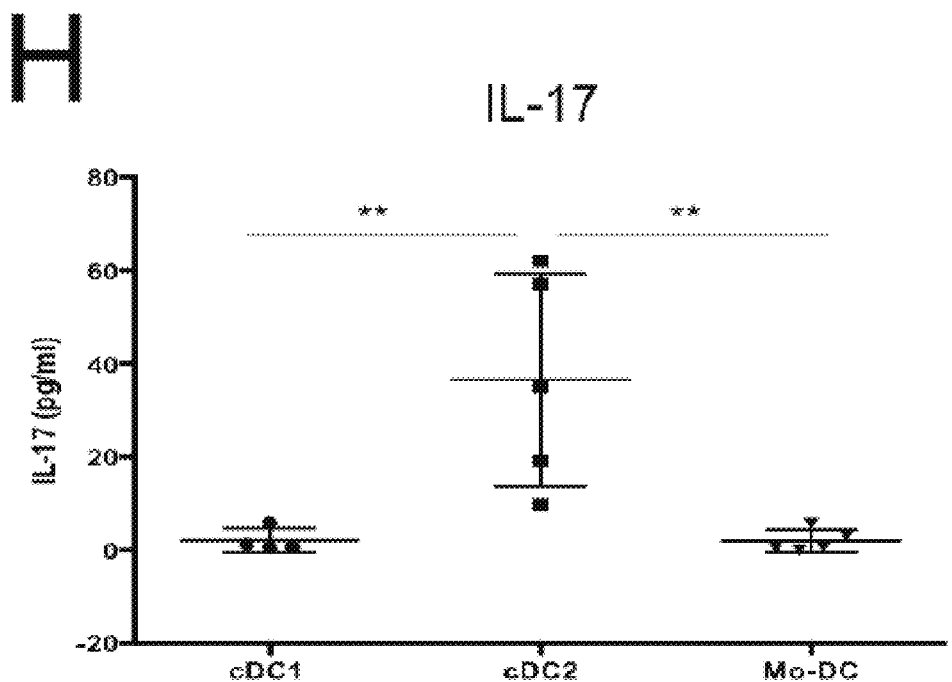
Figure 5:
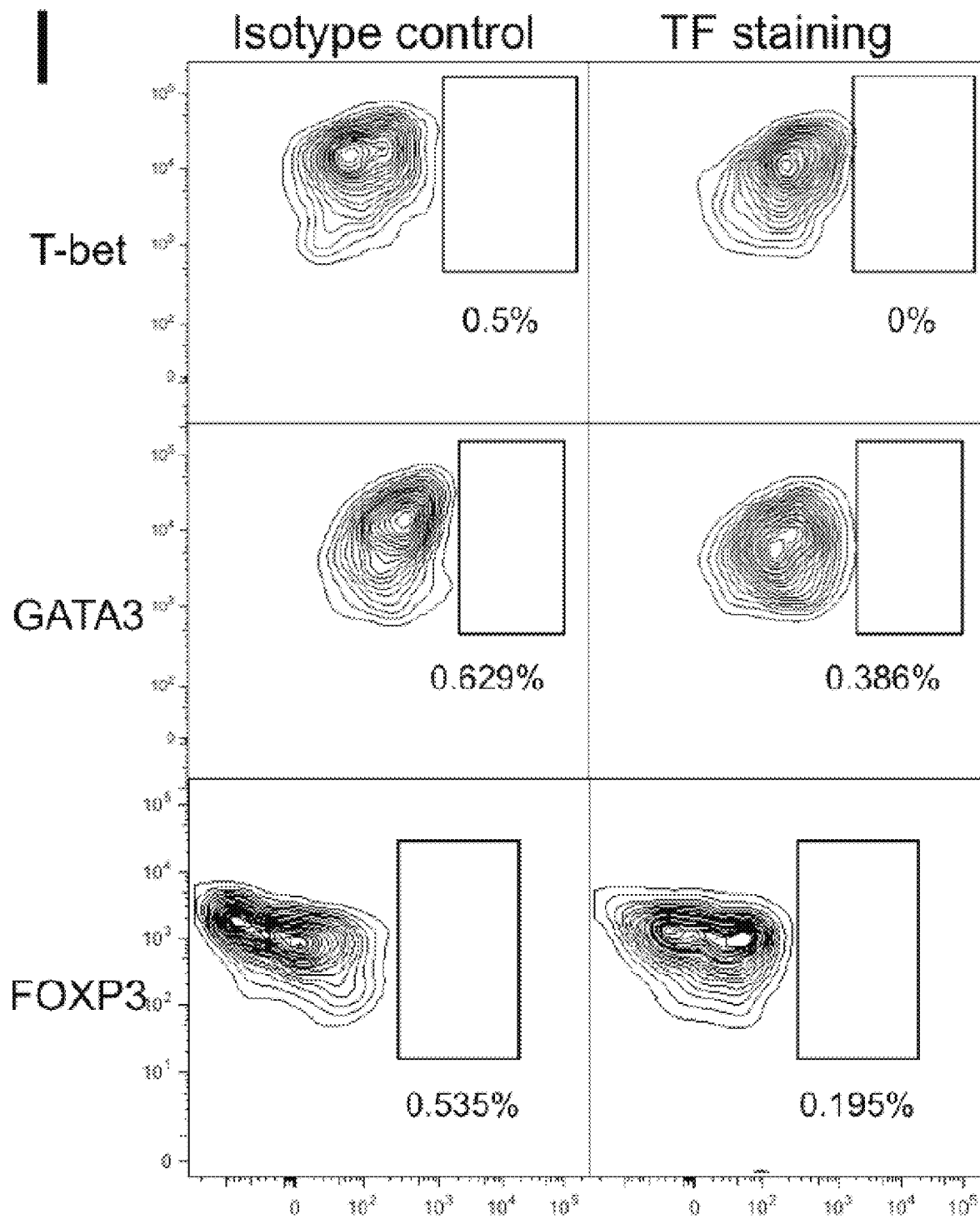
Figure 5:
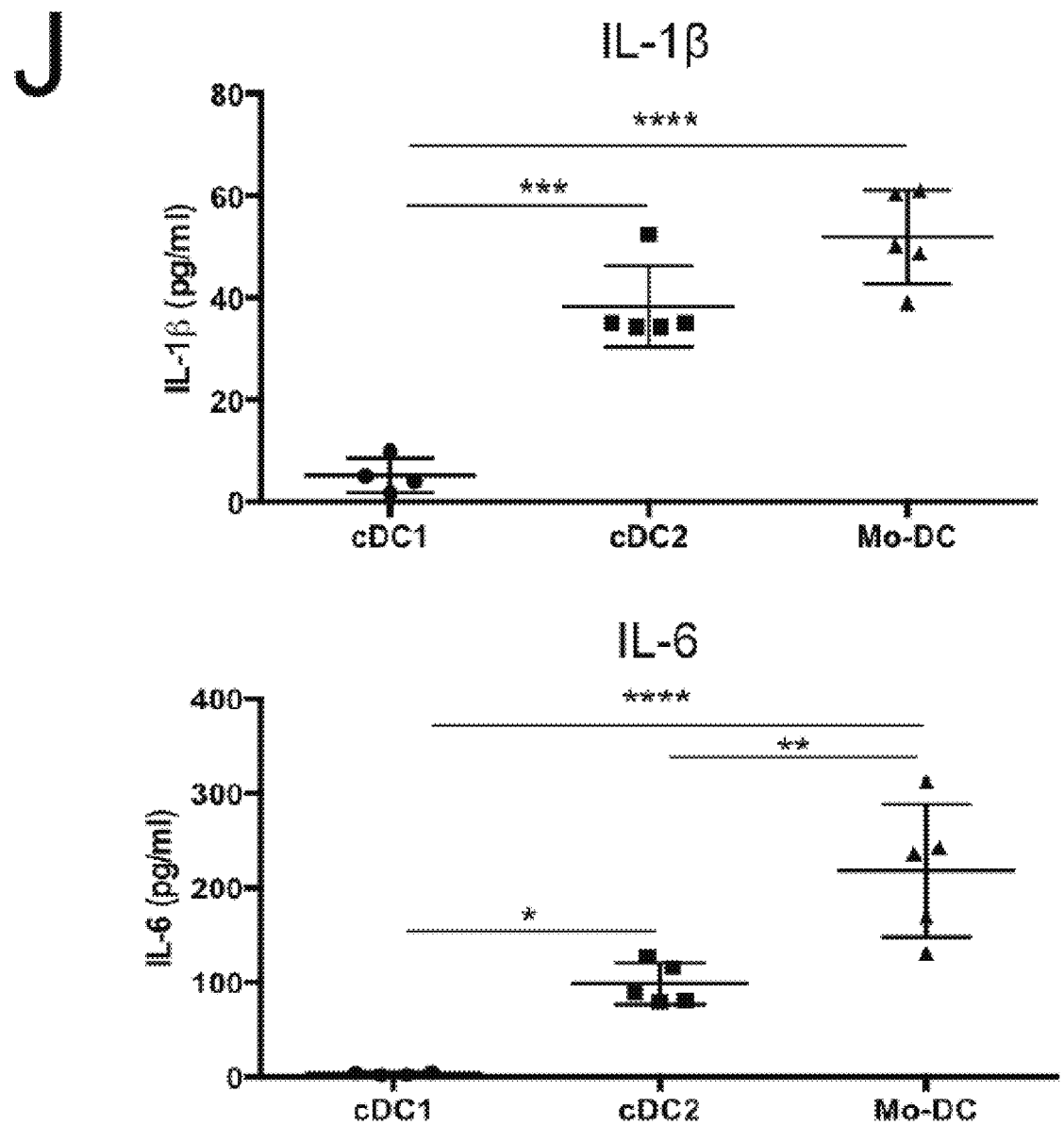

Example 5: Both cDC Populations Activate Naive CD8⁺ and CD4⁺ T Cells, but Only cDC2 Induce a Th17 CD4⁺ T-Cell Phenotype We then evaluated the capacity of TADC subsets to activate naive T cells. In this regard, the expression of activating and inhibitory T-cell costimulatory molecules, such as CD80, CD86, PDL1 and PDL2 was very high on all TADC populations (FIG. 5A). First, the intrinsic antigen-presenting capacity of TADC subsets, irrespective of their antigen uptake and processing capacity, was assessed in a classic mixed-leukocyte reaction (MLR). All C57Bl/6 TADC subsets could activate naive Balb/c CD4⁺ and CH⁺ T-cell proliferation, at least to the same extent as the control splenic CD11c$^{hi}$MHC-II$^{hi}$B220⁻Ly6C⁻ cDC population (FIGS. 5B and 5C). Interestingly, the cDC2 showed the highest intrinsic antigen-presenting capacity towards both CD4⁺ and CD8⁺ T cells.

To incorporate the effect of a differential in vivo antigen uptake and processing capacity in our assay, TADC were sorted from LLC-OVA tumors and immediately co-cultured with CFSE-labeled TCR transgenic C8⁺ OT-I T cells or CD4⁺ OT-II T cells without additional ex-vivo Ag-loading or stimulation. At a DC/OT-I ratio of 1/10, only the two cDC subsets could effectively induce CD8⁺ T-cell proliferation, hence demonstrating their in vivo immunostimulatory phenotype, whereby the cDC1 were considerably more potent (FIG. 5D). Also in the case of CD4⁺ T cells, only the cDC subsets were able to induce T-cell proliferation at a DC/OT-II ratio of 1/10, with now cDC2 being most efficient (FIG. 5E). Notably, within the timeframe of the experiment (3 days of stimulation), hardly any IFN-γ and IL-4 (FIG. 5F) and no IL-13 (data not shown) could be detected in the supernatant of OT-II/TADC cocultures, illustrating the lack of Th1 and Th2 induction by the TADC subsets. Interestingly however, cDC2 induced the differentiation of a Th17 population, as demonstrated by the upregulation of RORγt—but not T-bet, GATA3 or FoxP3—in a population of OT-II cells, and the secretion of IL-17 in the supernatant (FIGS. 5G, 5H and 5I). No RORγt⁺ T cells nor IL-17 production were found in any other condition. The induction of Th17 may result from the inherently high production of Th17-inducing cytokines, such as IL-1β and IL-6, by cDC2 (FIG. 5J). It should be noted, however, that Mo-DC secrete even higher levels of these cytokines, but still lack the capacity to induce Th17, suggesting that other inherent properties of the DC are important for Th17 generation.

Example 6: Mo-DC Display an Immune Suppressive TIP-DC Phenotype

Figure 6:
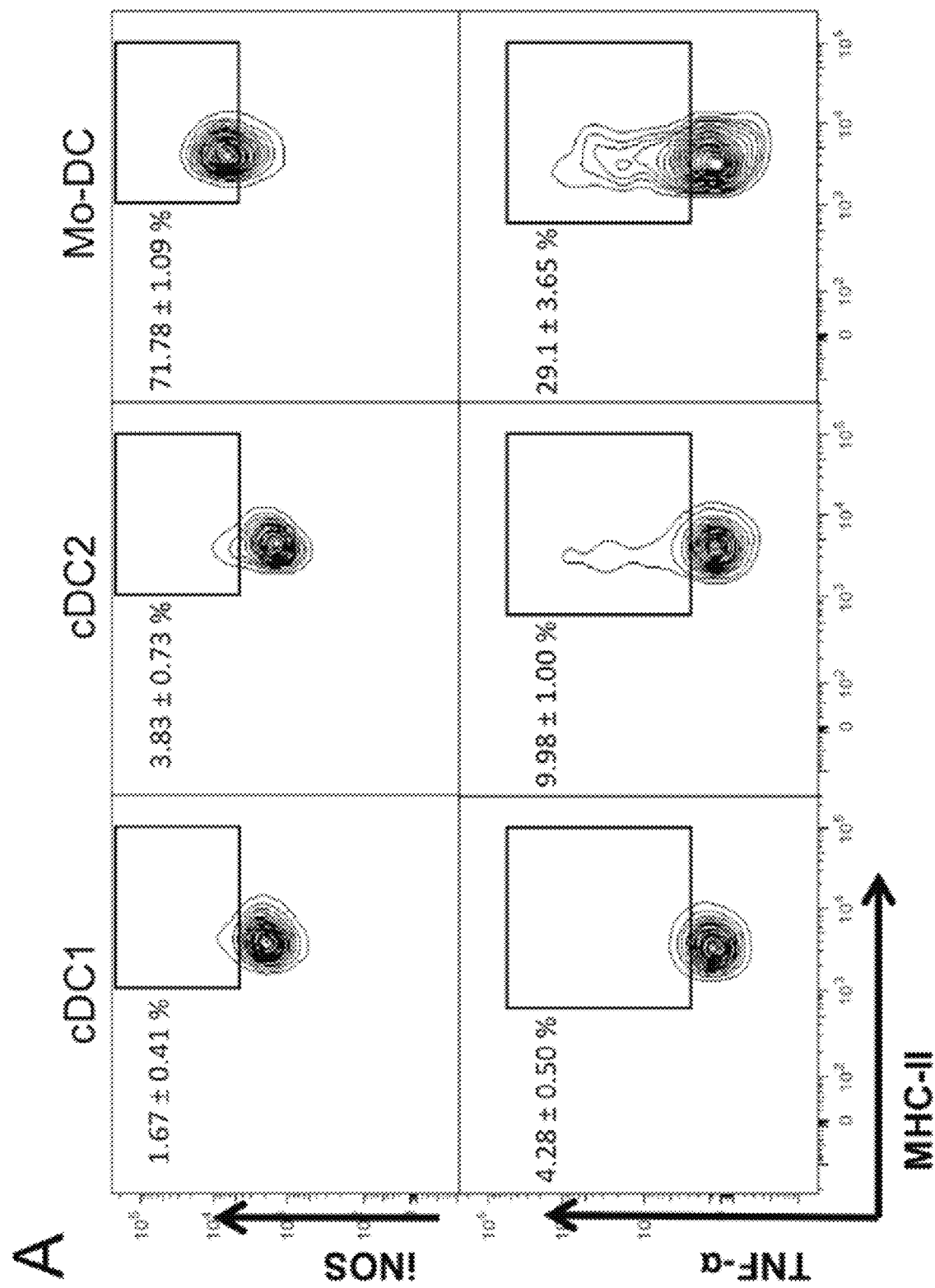
FIG. 6 shows the immune suppressive TIP-DC phenotype of Mo-DC. (A) Intracellular staining for iNOS and TNF-α was performed on single-cell suspensions of 12-day old 3LL-R tumors. n=4. (B) Supernatants of TADC subset cultured for 48 h were tested for presence of TNF-α by luminex. Analysis by one-way ANOVA. *, p<0.05; **, p<0.01. (C) Staining for mitochondrial superoxide anion was performed on single-cell suspensions of 12-day old 3LL-R tumors. n=4. (D) Supernatants of TADC subset cultured for 48 h were tested for presence of CCL2, CCL4 and CXCL1 by luminex. n≥4 Analysis by one-way ANOVA. *, p<0.05; , p<0.01; *, p<0.001; ****, p<0.0001. (E) Supernatants of TADC subset cultured for 48 h were tested for presence of IL-10 and IL-12 by luminex. The graph depicts the IL-10/IL-12 ratio. n≥4. Analysis by one-way ANOVA. *, p<0.05; **, p<0.01. (F) Sorted Mo-DC were co-cultured with OT-I T cells for 3 days at a DC/OT-I ratio of 1/2. The histograms represent CFSE dilution, indicative for T-cell proliferation. Conditions compared are: non-stimulated T cells (No TADC) and T cells in the presence of Mo-DC with or without iNOS inhibitor (LNMMA) or α-IFN-γ. n=2.
Figure 6:
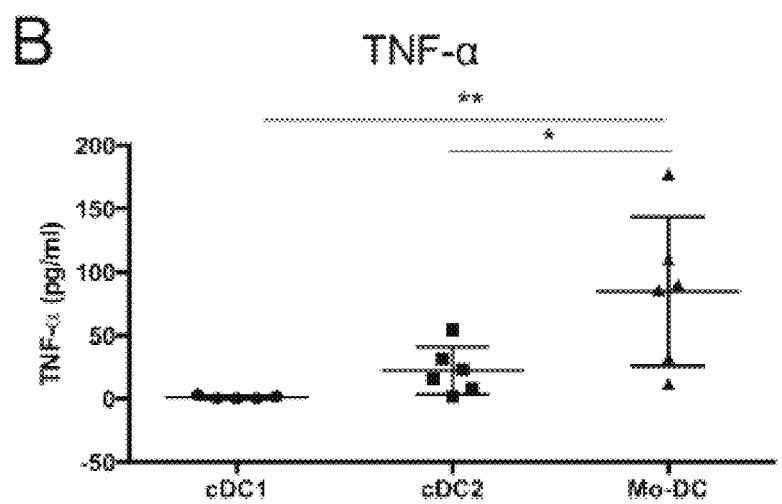
Figure 6:
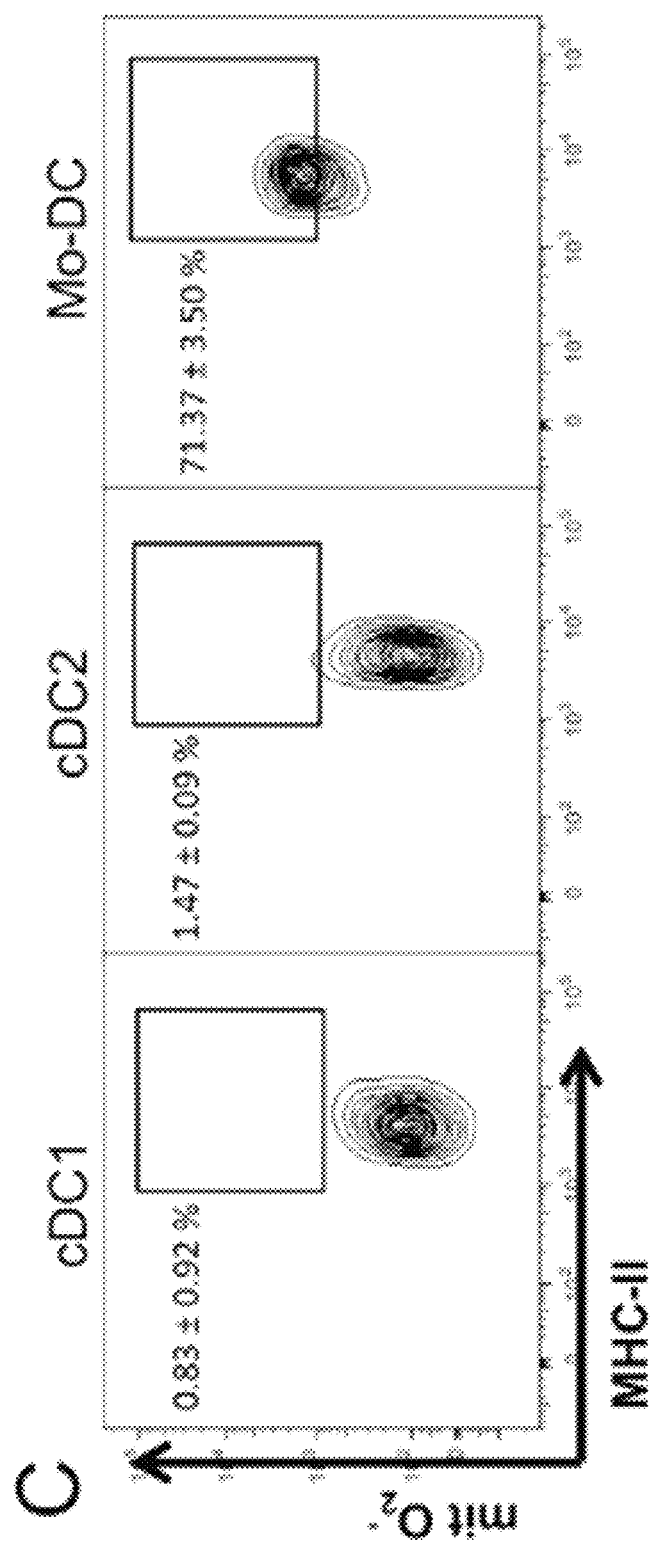
Figure 6:
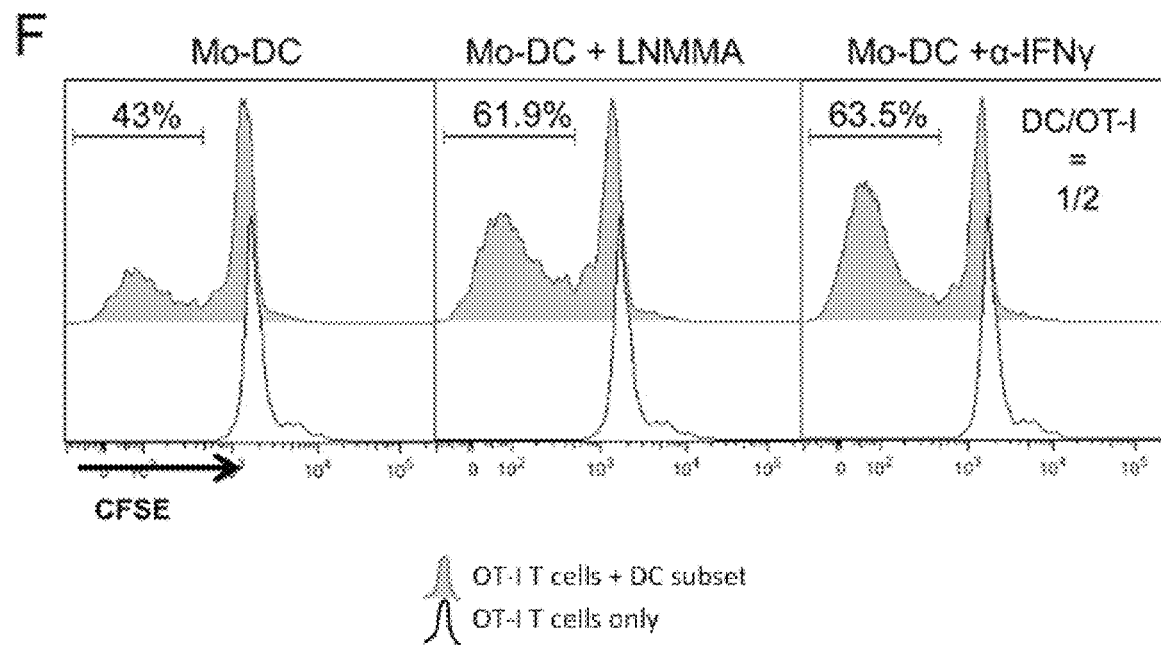

Tumor-associated Mo-DC were consistently less efficient in activating naive antigen-specific T cells, in spite of their higher antigen uptake and processing capacity. Therefore, we wondered whether the Mo-DC displayed features that could annihilate their T-cell stimulatory functions. We noted that Mo-DC co-expressed high levels of TNF-α and iNOS and hence displayed a phenotype reminiscent of inflammatory TIP-DC (FIGS. 6A and 6B). Moreover, these cells produced the highest level of the inflammatory cytokines IL-6 and IL-1β, the monocyte and neutrophil attracting chemokines CCL2, CCL4 and CXCL1 and reactive oxygen species, such as the mitochondrial superoxide anion, of all TADC populations (FIGS. 5J, 6C and 6D). In addition, they displayed the highest IL-10/IL-12 balance (FIG. 6E), a feature that is linked with a less immunogenic DC phenotype.

Importantly, higher iNOS expression might result in a higher NO production, which is reported to be a potential T-cell suppressive molecule (Bronte and Zanovello, 2005; Schouppe et al., 2013). Mo-DC sorted from LLC-OVA tumors were co-cultured with CFSE-labeled CD8$^+$ OT-I T cells in the presence of the iNOS inhibitor L-NMMA (FIG. 6F). T-cell proliferation was significantly enhanced under these conditions, demonstrating an active NO-mediated T-cell suppressive activity by Mo-DC. The TIP-DC phenotype, including iNOS expression, was shown before to depend on IFN-γ (Bosschaerts et al., 2011). The addition of blocking anti-IFN-γ antibodies to the Mo-DC/OT-I cultures indeed increased T-cell proliferation to the same extent as iNOS inhibition. Notably, anti-IFN-γ and L-NMMA had no effect on Mo-DC/OT-II co-cultures (data not shown). Hence, Mo-DC display an immune suppressive TIP-DC phenotype that precludes the potent activation of CD8$^+$ T cells.

Figure 7:
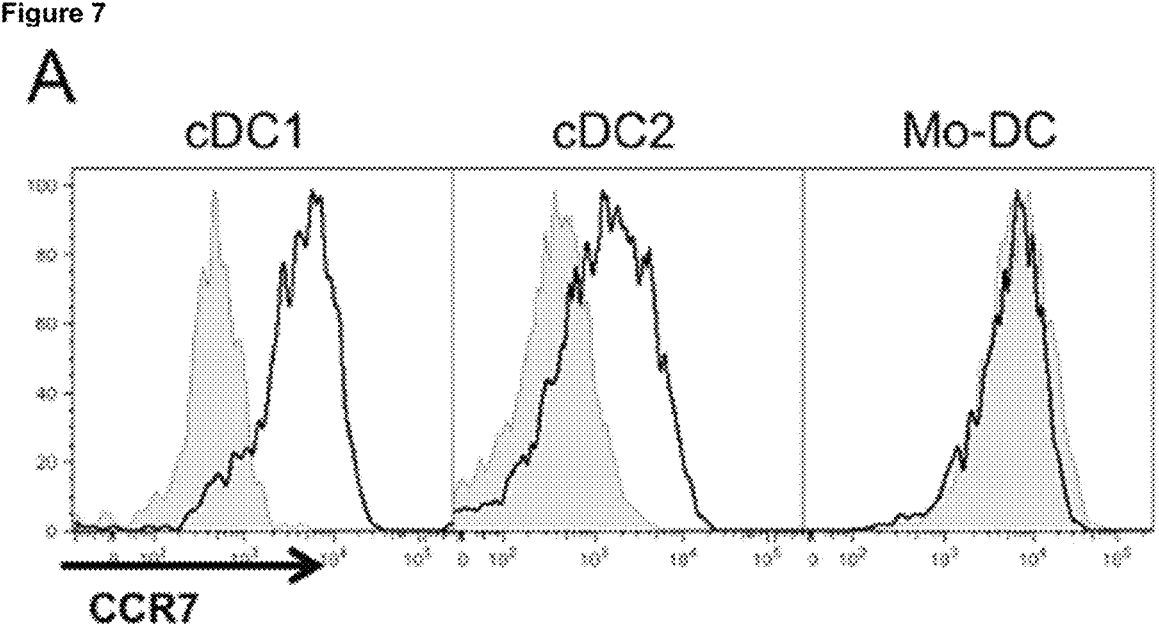
FIG. 7 shows the migration of the tumor-associated cDC subsets to tumor draining lymph nodes and the differential activation of CD8$^+$ and CD4$^+$ T cells. (A) Single-cell suspensions of 12-day old 3LL-R tumors were stained for CCR7 and histogram overlays are shown. Black line=expression of CCR7; shaded histogram=isotype control. n=3. (B) Expression of Ova was assessed in LLC-Ova cancer cells and tumor and tumor-draining lymph nodes (axillary or inguinal) of 11-day and 22-day old LLC-Ova tumor-bearing mice using qRT-PCR. The expression was normalized based on the S12 housekeeping gene. n=3. (C-D) The indicated amount of sorted DC subsets from tumor-draining lymph nodes were co-cultured upon 3 days with 10$^5$ purified CD8$^+$ OT-I T cells (C) or CD4$^+$ OT-II T cells (D). The histograms represent CFSE dilution, indicative for T-cell proliferation. Black line=non-stimulated T cells without TADC; shaded histogram=T cells in the presence of TADC. Results are representative of 3 independent experiments with n=pool of 10-12 tumors. (E) Intracellular staining on OT-II T cells cocultered with sorted tumor-draining lymph nodes cDC2 subsets for 3 days at a DC/OT-II ratio of 1/10 was performed for the Th17-inducing transcription factor RORγt. Isotype control and transcription factor staining are depicted. n=pool of 10.
Figure 7:
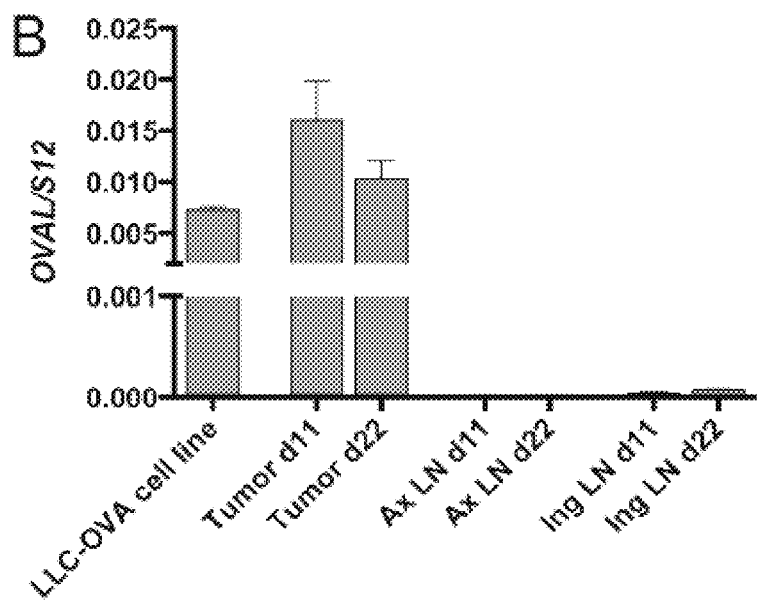
Figure 7:
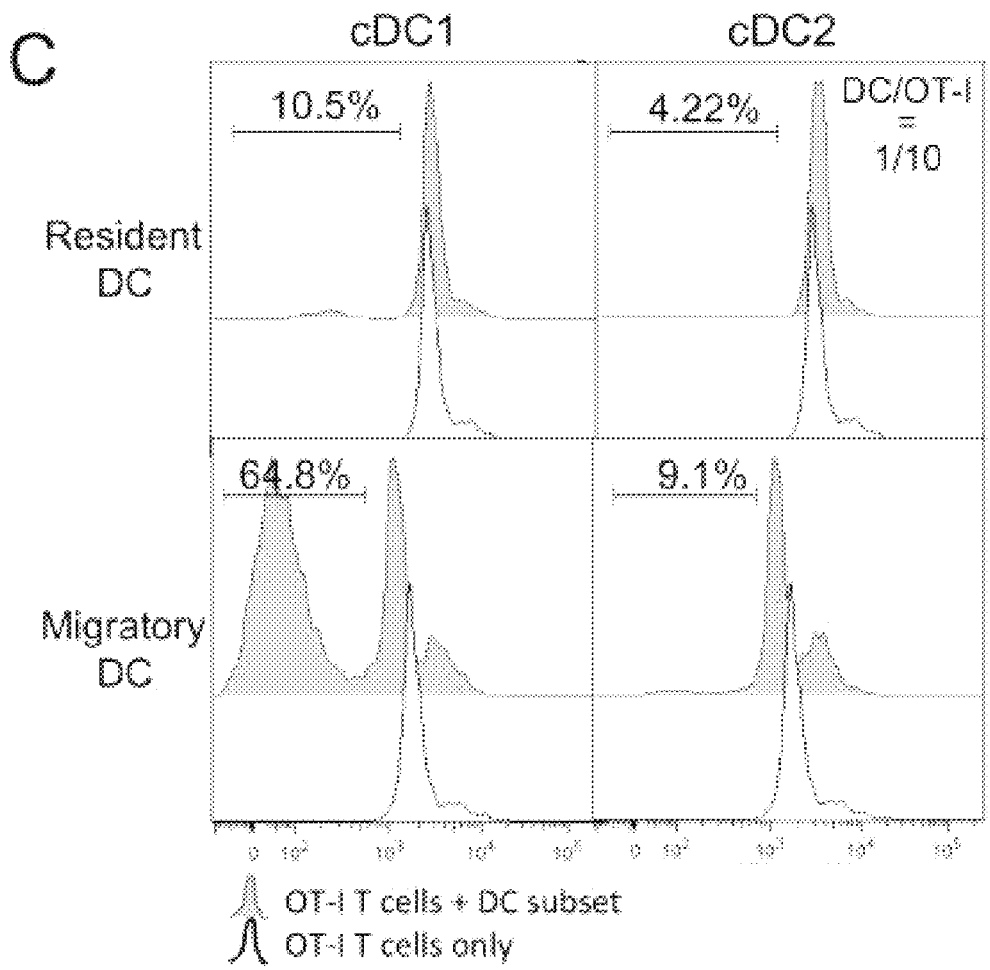
Figure 7:
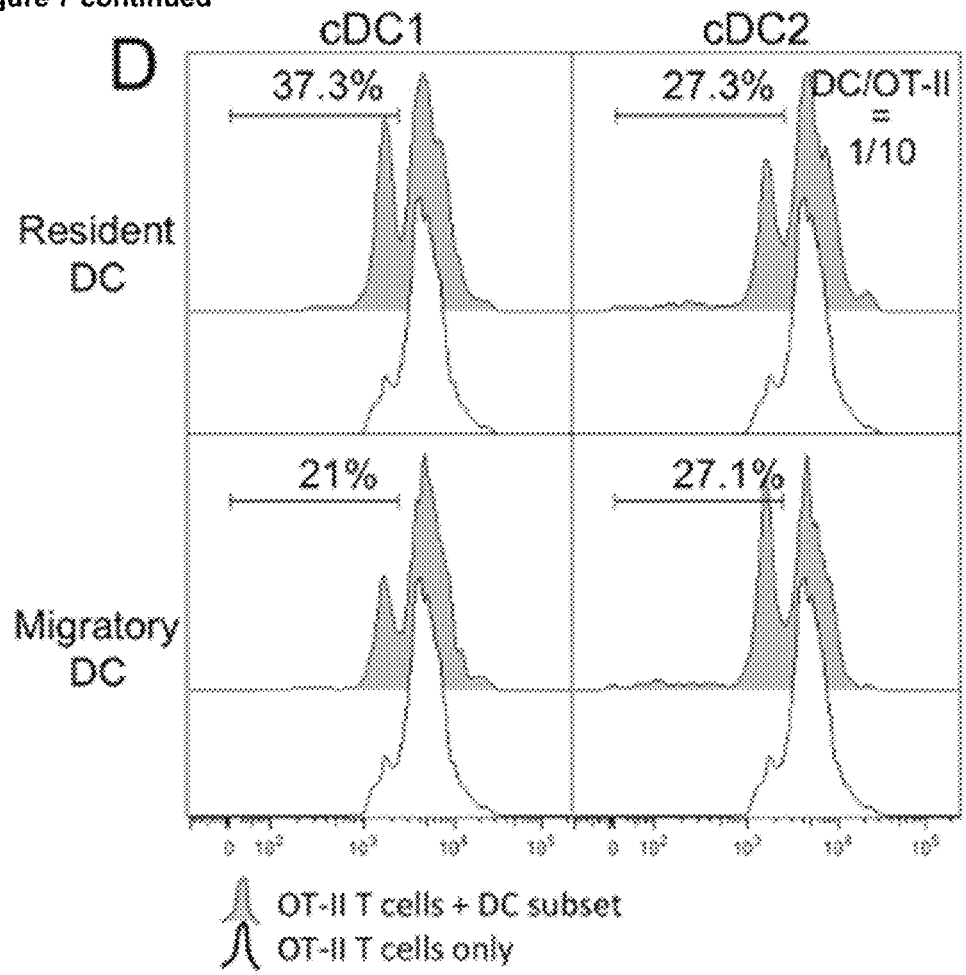
Figure 7:
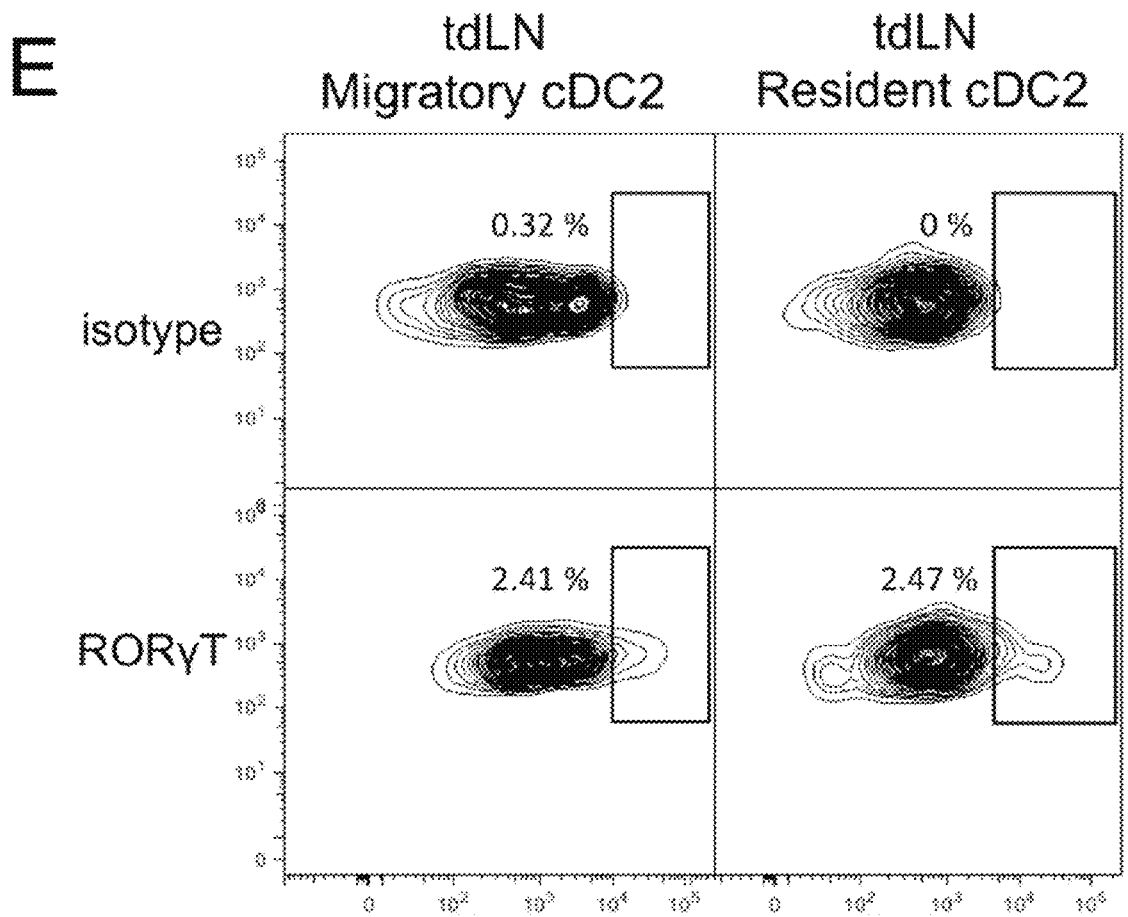

Example 7: Both Tumor-Associated cDC Subsets Migrate to Tumor Draining Lymph Nodes and Differentially Activate CD8$^+$ and CD4$^+$ T Cells Tumor-associated cDC possessed T-cell stimulating capacity, so we next wondered whether these cells were capable of migrating to the tumor-draining lymph nodes (tdLN) and present tumor antigen. CCR7 expression, which is a prerequisite for DC migration to LN, was only present on the cDC subsets but not on Mo-DCs (FIG. 7A).

In the axillary and inguinal tdLN (draining LN for a subcutaneous tumor in the flank of the animal), cDC1 and cDC2 subsets, but not Mo-DC, were present within the migratory DC population (data not shown), confirming the non-migratory character of Mo-DCs. Migratory and resident DC were discriminated based on CD11c and MHC-II expression, as previously reported (Kissenpfennig et al., 2005; Ohl et al., 2004). To assess whether these cDC present tumor antigen, they were sorted from tdLN of LLC-OVA tumor-bearing mice and co-cultured with CFSE-labeled CD8$^+$ OT-I T cells or CD4$^+$ OT-II T cells. Importantly, care was taken that no OVA$^+$ cancer cells were present in the tdLN at the time of cDC sorting, as illustrated by the absence of OVA mRNA (FIG. 7B). Migratory cDC1, but not cDC2, strongly stimulated OT-I proliferation (FIG. 7C), suggesting in vivo migration of SIINFEKL-loaded cDC1 from the tumor to the tdLN. Notably, both resident cDC subsets were largely incapable of inducing OT-I T-cell proliferation (FIG. 7C). By contrast, both migratory cDC1 and cDC2 could stimulate OT-II T-cell proliferation (FIG. 7D). Unexpectedly, also the resident cDC1 and cDC2 induced OT-II proliferation (FIG. 7D), suggesting that migratory tumor-associated cDC could transfer antigen to LN-resident cDC populations for effective OT-II priming. Notably, similar to the tumor-associated cDC2, tdLN migratory and resident cDC2 also induced RORγt in a fraction of the OT-II T cells (FIG. 7E), while no upregulation of Foxp3, T-bet or GATA3 could be observed (data not shown).

Figure 8:
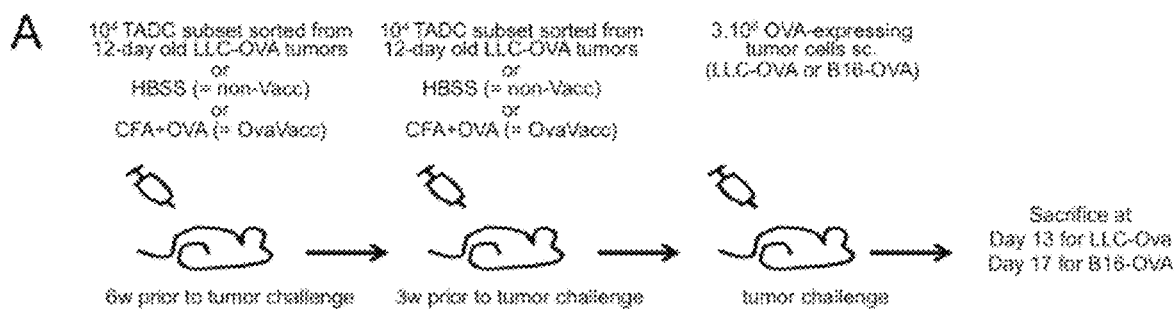
FIG. 8 shows that cDC2 vaccination is more beneficial than cDC1 vaccination in LLC-tumor bearing mice and repolarizes CD4$^+$ T cells to a Th17 phenotype. (A) Schematic representation of the vaccination protocol. (B-C) Growth curve (B) and tumor weights (C) of LLC-Ova tumors after vaccination with LLC-OVA TADC subsets. (D-J) Percentages of CD8$^+$ T cells (D), Ova-specific CD8$^+$ T cells (E), CD4$^+$ T cells (F), RORγt$^+$ CD4$^+$ T cells (G), FOXP3$^+$ CD4$^+$ T cells (H), Tbet$^+$ CD4$^+$ T cells (I), Gata3$^+$ CD4$^+$ T cells (J), in LLC-Ova tumors after vaccination with LLC-OVA TADC subsets following the protocol depicted in (A). For all experiments, results are representative of 2 independent experiments with n=4-15 tumors. Statistical Analysis by one-way ANOVA. *, p<0.05; , p<0.01; *, p<0.001; ****, p<0.0001.
Figure 8:
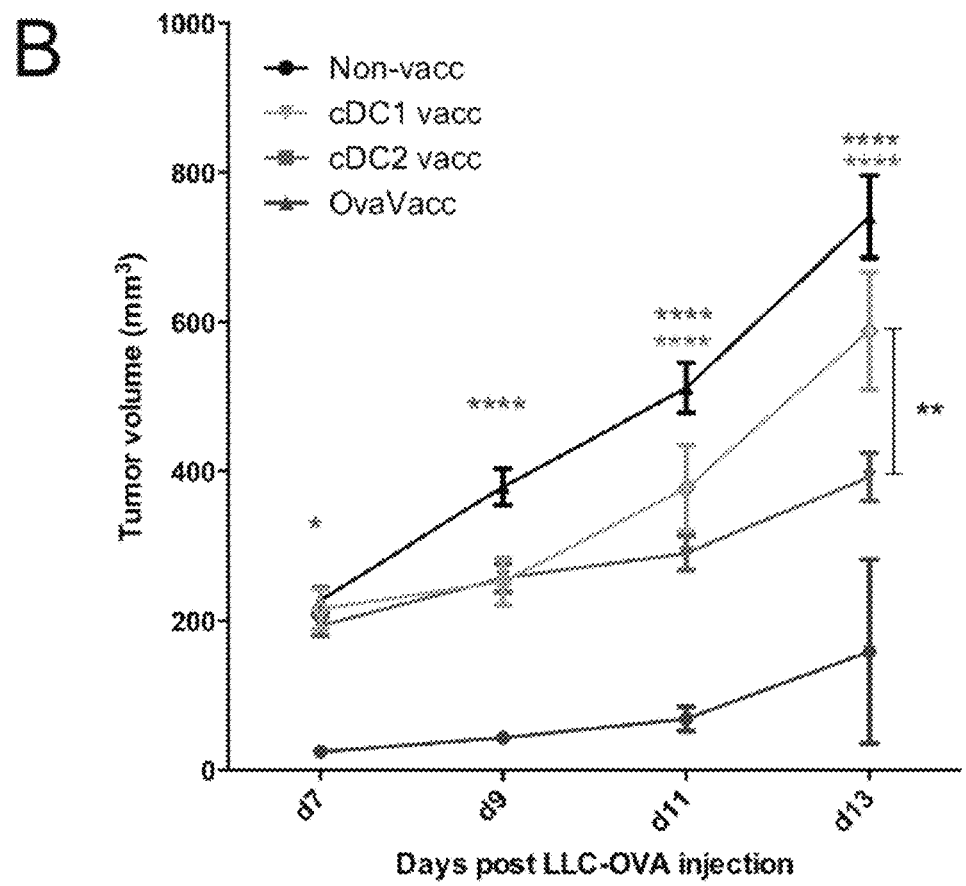
Figure 8:
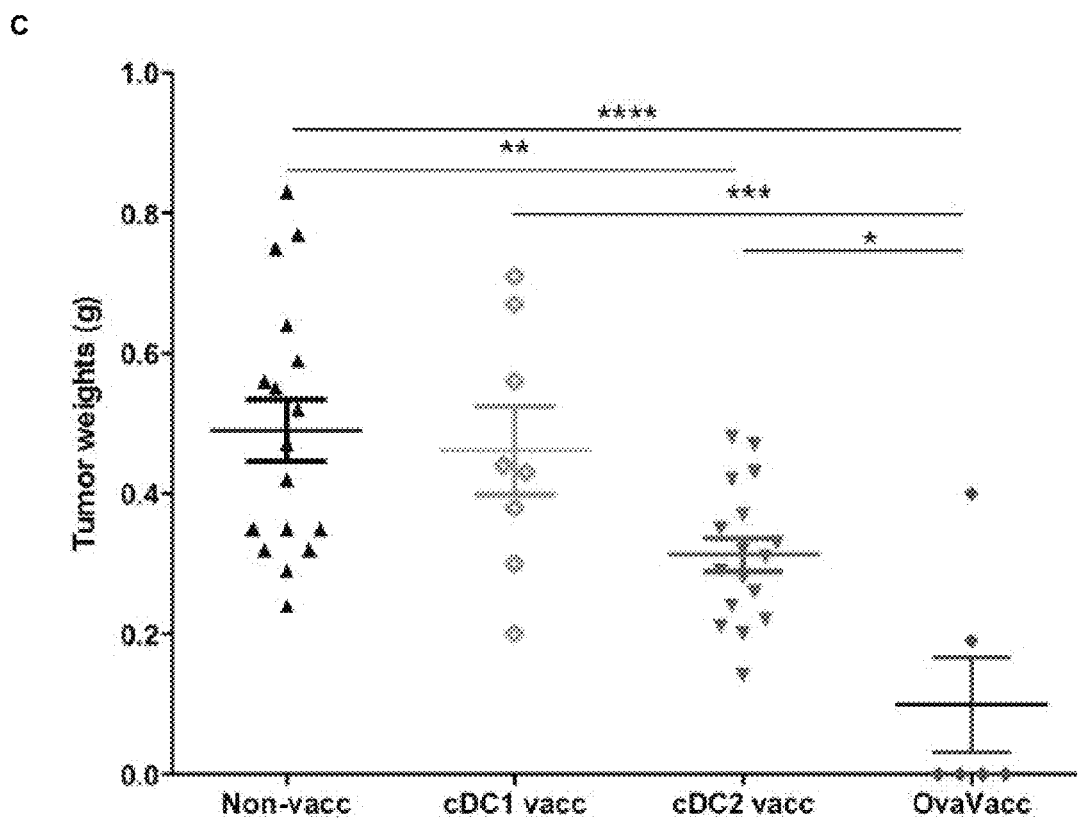
Figure 8:
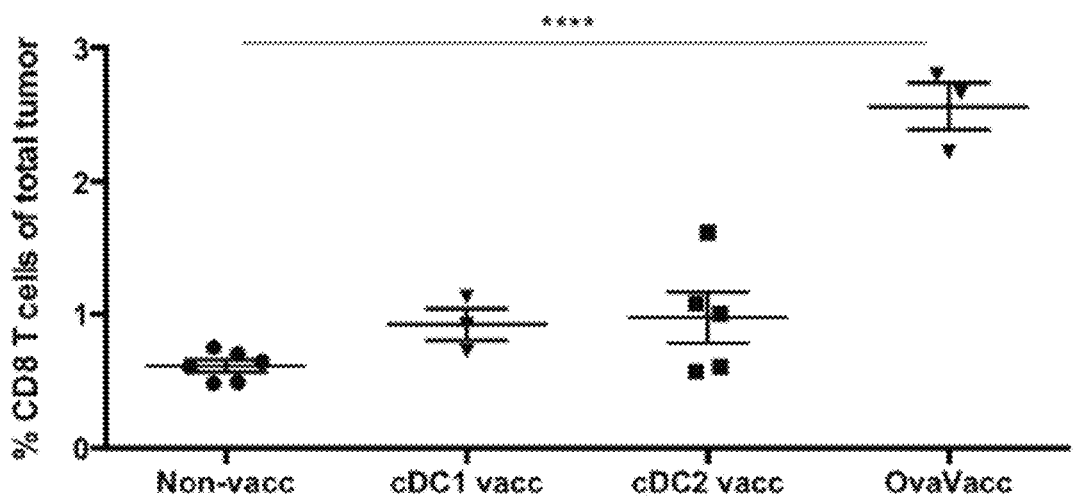
Figure 8:
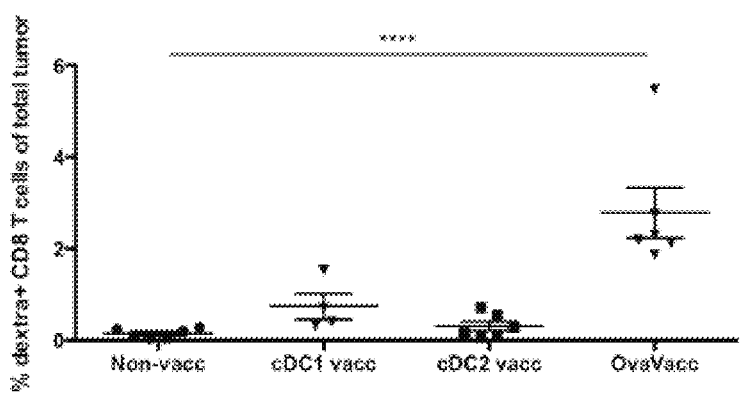
Figure 8:
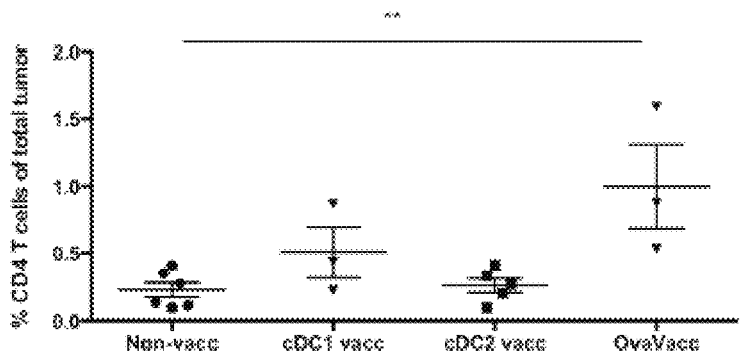
Figure 8:
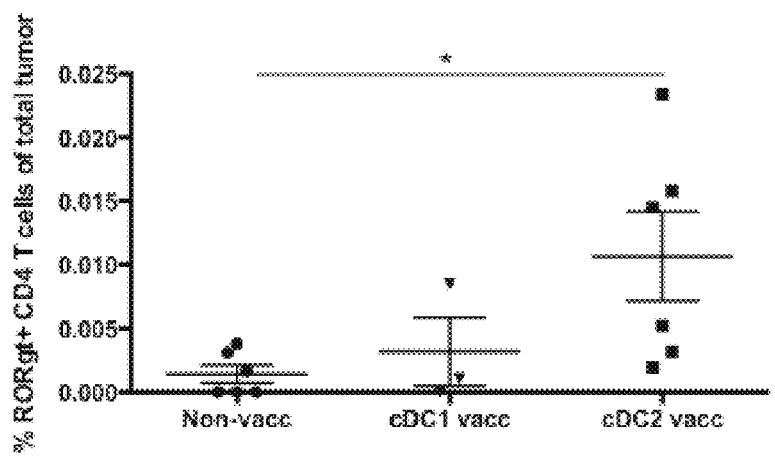
Figure 8:
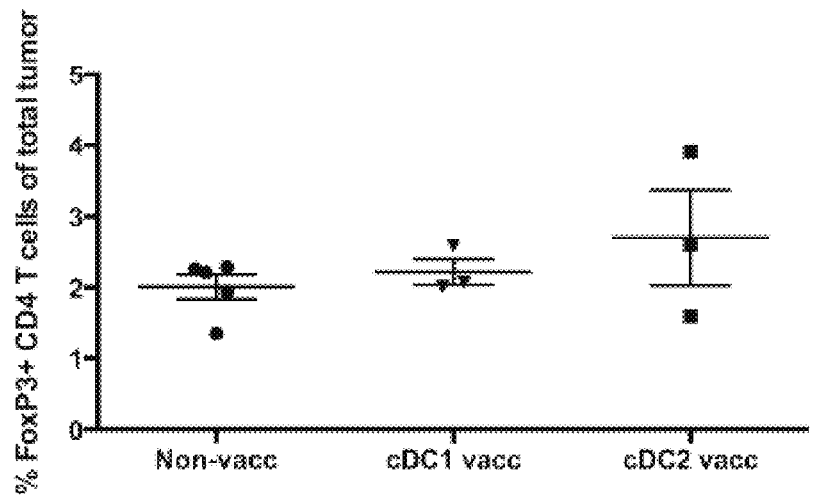
Figure 8:
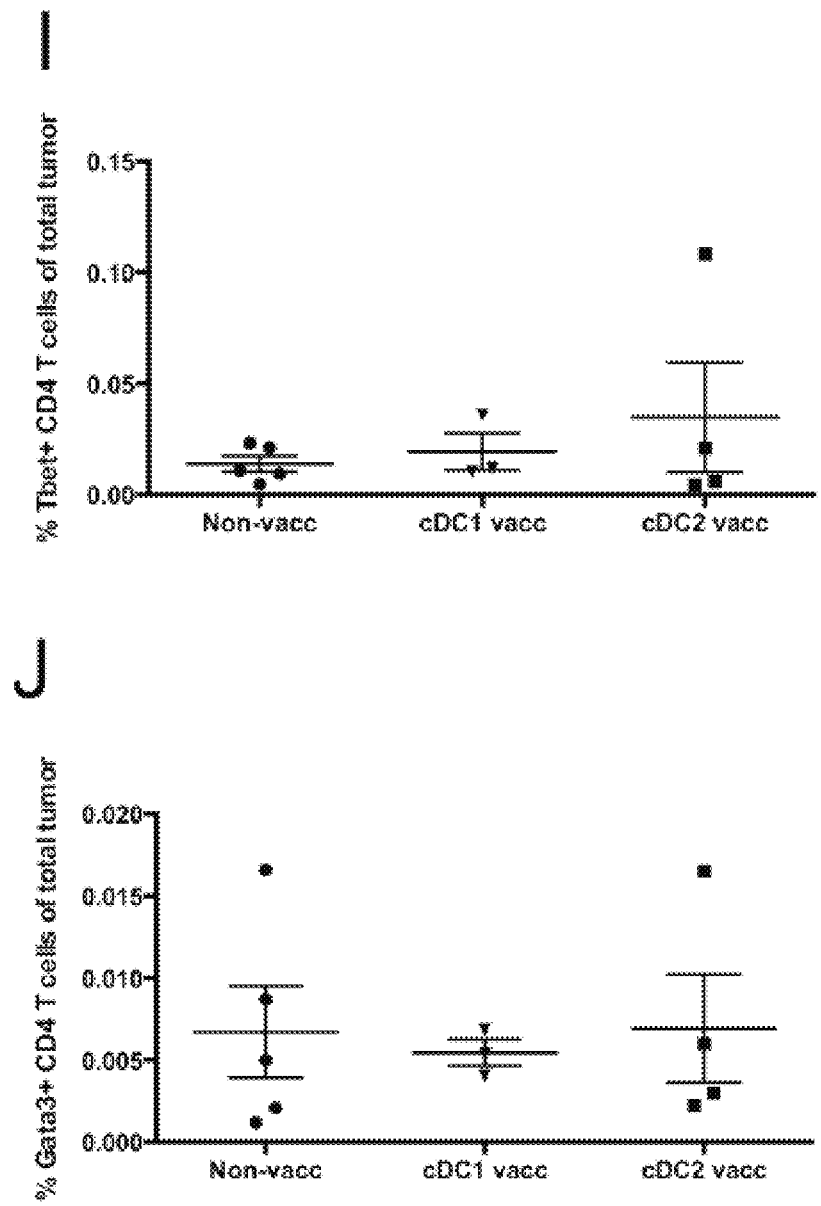

Example 8: cDC1 and cDC2 have Both Beneficial but Different Therapeutic Effects when Used for Vaccination Finally, to assess whether tumor-derived DC subsets could be used to elicit therapeutically relevant immune memory responses in cancer, we set up vaccination experiments as depicted in FIG. 8A. Importantly, the sorted TADC subsets used for the vaccination experiments were not ex vivo stimulated with cytokines, nor loaded with tumor antigen. Since Mo-DC did not display LN migratory capacities and harbored immunosuppressive capacities (FIG. 6F), we decided to focus on the potential therapeutic effects of the cDC subsets.

Figure 13:
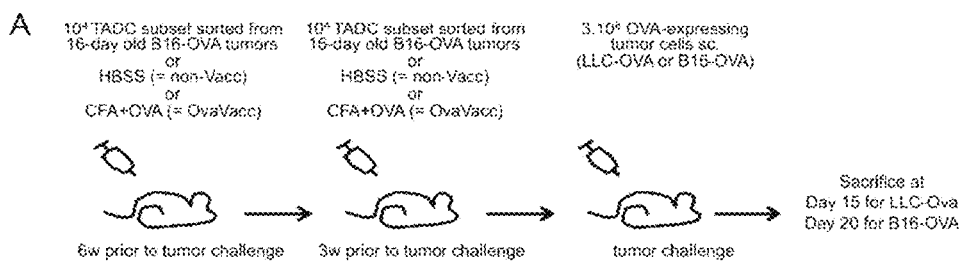
FIG. 13 shows that B16-OVA derived cDC2 vaccination is more beneficial than B16-OVA derived cDC1 vaccination in LLC-tumor bearing mice, while both B16-OVA derived cDC1 and cDC2 vaccination confer protection in B16-OVA tumor bearing mice. (A) Schematic representation of the vaccination protocol. (B-C) Growth curve (B) and tumor weights (C) of LLC-OVA tumors after vaccination with B16-OVA TADC subsets. (D-E) Growth curve (D) and tumor weights (E) of B16-OVA tumors after vaccination with B16-OVA TADC subsets. n=5 to 7 tumors. Statistical analysis by one-way ANOVA. *, $p<0.05$; , $p<0.01$; *, $p<0.001$; ****, $p<0.0001$.
Figure 13:
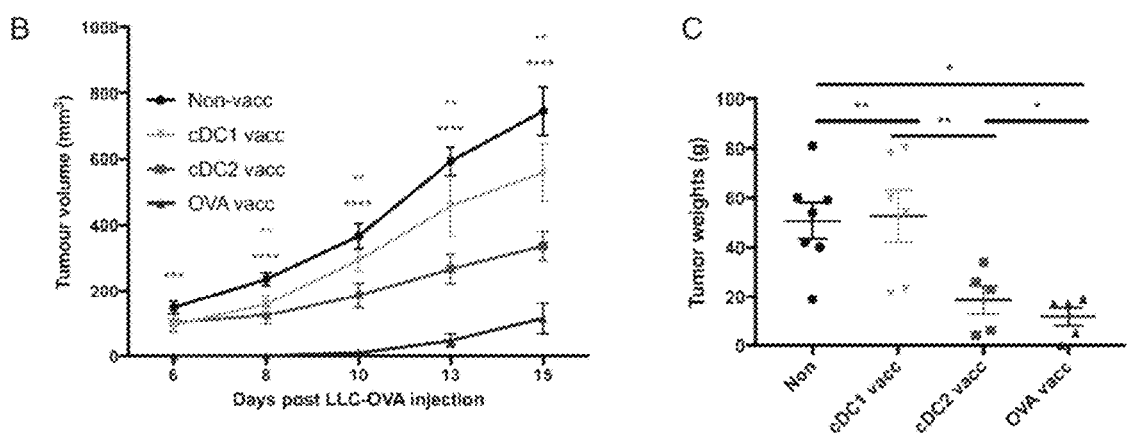
Figure 13:
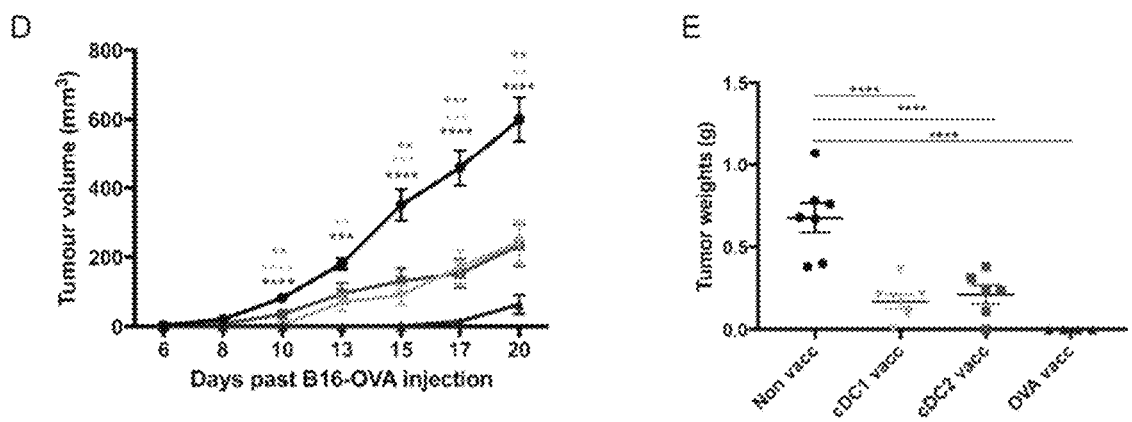

Remarkably, upon challenge with LLC-OVA, only the cDC2-vaccinated mice had a significantly reduced tumor growth rate and weight compared to the non-vaccinated mice (FIGS. 8B and 8C). This was the case when vaccinating mice with cDC2 sorted from LLC-OVA tumors, but also when cDC2 originated from B16-OVA tumors (FIGS. 13B and 13C). A similar, though non-significant, trend was seen in the cDC1-vaccinated cohort (FIGS. 8B and 13B). As expected, tumor growth in OVA-vaccinated mice was strongly retarded. Slower tumor growth correlated with a slightly increased presence of CD8$^+$ T cells in tumors of both vaccinated cohorts, which, however, did not reach the significantly higher levels seen in the OVA-vaccinated mice (FIG. 8D). Remarkably, using H2K$^b$/SIINFEKL dextramer staining, the proportion of tumor antigen-specific CD8$^+$ T cells within the total CD8$^+$ T-cell population was significantly increased in OVA-vaccinated mice and a trend was visible in cDC1-vaccinated, but not in cDC2-vaccinated mice (FIG. 8E). These data are in line with the superior CTL-stimulatory capacity of cDC1, and suggest that the stronger anti-tumor effect of cDC2 vaccination is mediated by other changes in the tumor microenvironment. In this respect, cDC2, but not cDC1, were shown to stimulate Th17 cells in vitro and in tdLN (FIGS. 5G and 7E). In line with these data, the percentage of RORγt$^+$ CD4$^+$ tumor-infiltrating lymphocytes (TIL) was only significantly increased in tumors from cDC2-vaccinated mice, without an increase in the overall proportion of CD4$^+$ T cells (FIGS. 8F and 8E). No changes could be observed in the amount of FoxP3$^+$ Treg, T-bet$^+$ Th1 or GATA3$^+$ Th2 CD4$^+$ TIL after vaccination, in any condition (FIGS. 8H, 8I and 8J).

Figure 9:
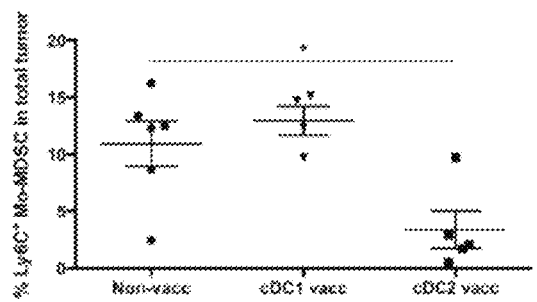
FIG. 9 shows that cDC2 vaccination reduces the MDSC infiltrate and reprograms TAM from a protumoral M2-like to a M1-like phenotype. (A-B) Percentages of Mo-MDSC (A) and G-MDSC (B) in LLC-Ova tumors after vaccination with LLC-OVA TADC subsets following the protocol depicted in FIG. 8A. Results are representative of 2 independent experiments with n=4-15 tumors. Statistical Analysis by one-way ANOVA. *, p<0.05. (C) CD11b$^+$ Ly6C$^{hi}$ Ly6G$^-$ Mo-MDSC and CD11b$^+$ Ly6C$^{int}$ Ly6G$^+$ G-MDSC were sorted from 12-day old 3LL-R tumor single cell suspensions and added at different ratios to OVA-stimulated OT-I splenocytes during 42 h and the proliferation T cells was measured via $^3$H-thymidine incorporation (cpm). Results are representative of 3 independent experiments with n=pool of 6 tumors. (D-E) Percentages of CD11b$^+$ Ly6G$^-$ Ly6C$^-$ TAM (D) and the ratio of M2-like MHC-II$^{low}$ TAM/M1-like MHC-II$^{high}$ TAM (E) in LLC-Ova tumors after vaccination with LLC-OVA TADC subsets following the protocol depicted in FIG. 8A. Results are representative of 2 independent experiments with n=4 to 12 tumors. Statistical Analysis by one-way ANOVA. ***, p<0.001. (F) Representative plot of LLC-Ova tumors of cDC2- or HBSS- vaccinated mice gated on CD11b$^+$ Ly6G$^-$ single cells. (G) Expression of indicated M1 and M2 associated genes in sorted MHC-II$^{low}$ and MHC-II$^{high}$ TAM subsets of LLC-OVA tumor bearing mice vaccinated with cDC2 or HBSS was assessed using qRT-PCR. The expression was normalized based on the S12 housekeeping gene. n=pool of 6 tumors. Statistical Analysis by one-way ANOVA. *, p<0.05; , p<0.01; *, p<0.001; ****, p<0.0001.
Figure 9:
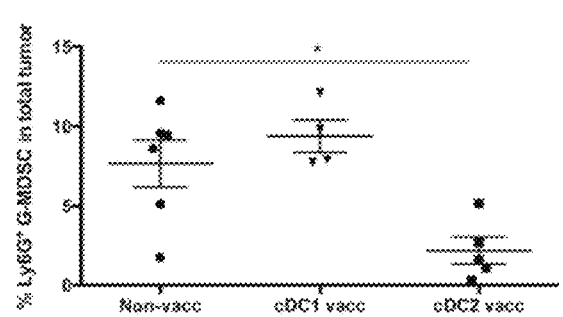
Figure 9:
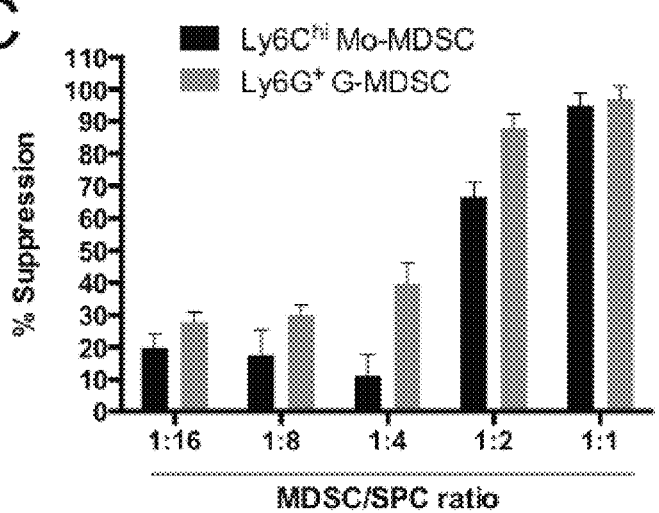
Figure 9:
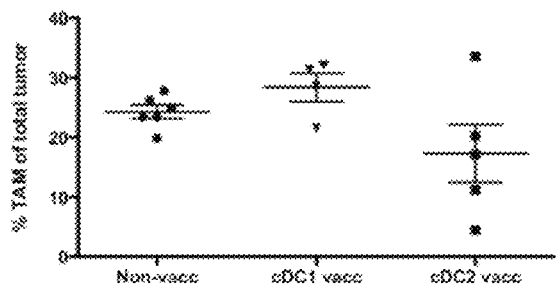
Figure 9:
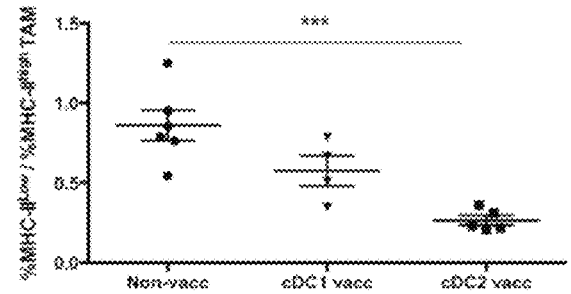
Figure 9:
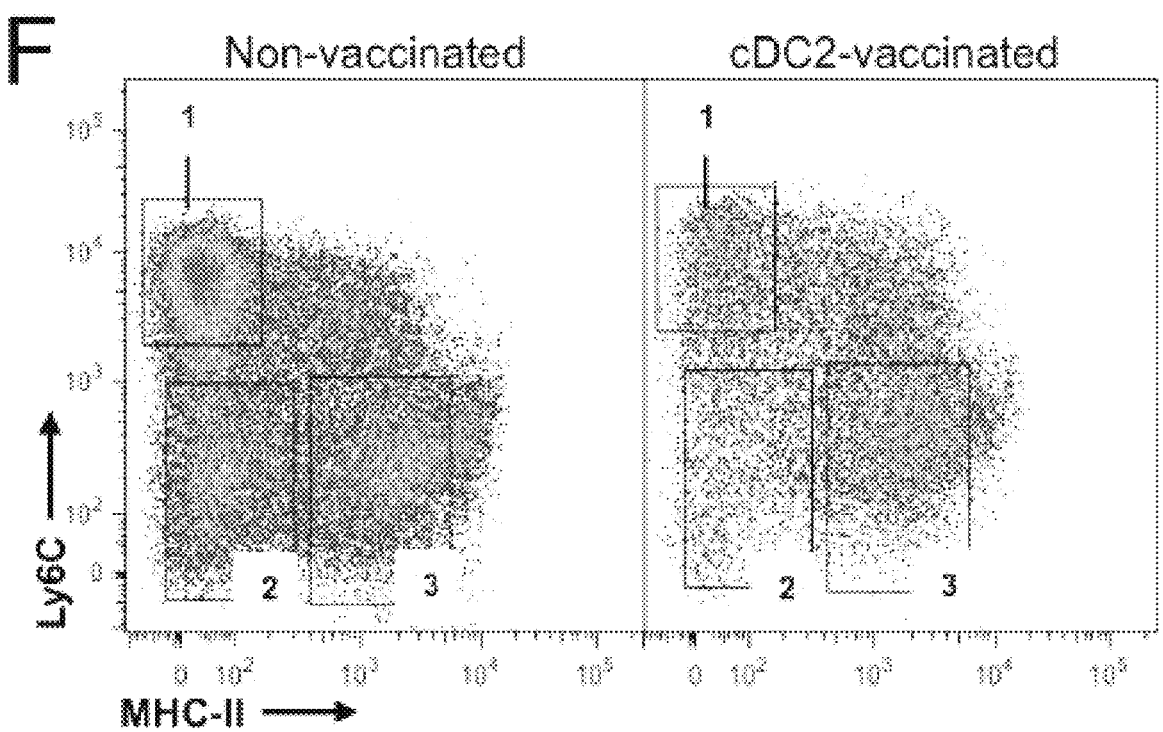
Figure 9:
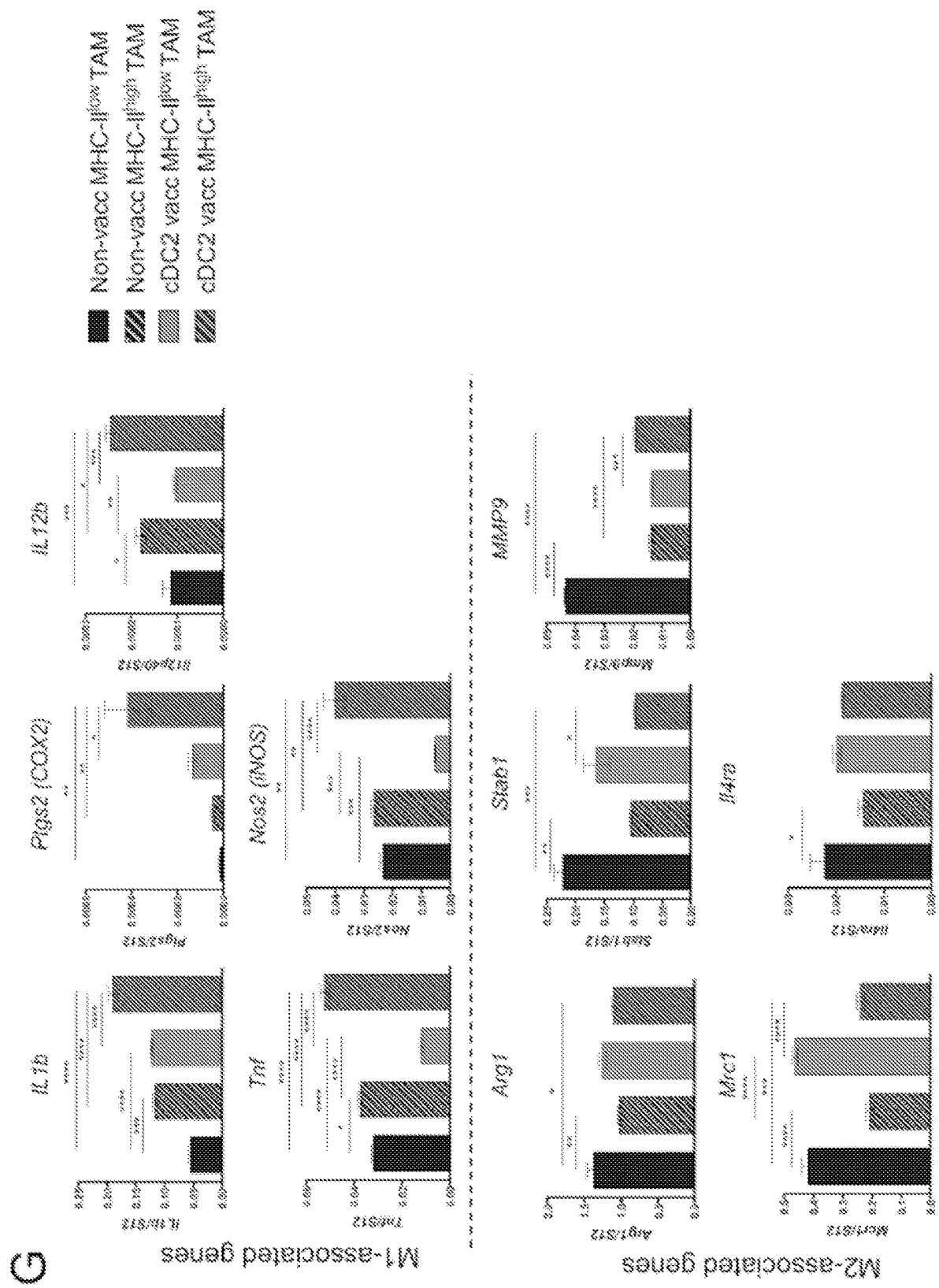

In multiple tumor models, including LLC, tumor growth is not only regulated by TIL, but also by the phenotype of tumor-associated myeloid cells such as myeloid-derived suppressor cells (MDSC) and TAM. Interestingly, the presence of CD11b$^{hi}$ Ly6C$^{hi}$ MHC-II$^{neg}$ Ly6G$^{neg}$ monocytic cells and CD11b$^{hi}$ Ly6C$^{int}$ MHC-II$^{neg}$ Ly6G$^{hi}$ granulocytic cells is significantly reduced in tumors of cDC2-vaccinated mice as compared to non-vaccinated and cDC1-vaccinated cohorts (FIGS. 9A and 9B). To assess whether these cells possess T-cell suppressive capacity, which would classify them as monocytic and granulocytic MDSC, they were FACS sorted from tumor single cell suspensions and added at different ratios to OVA-stimulated OT-I splenocytes. As shown in FIG. 9C, these cells strongly suppressed OT-I proliferation. Hence, cDC2 vaccination strongly reduces the presence of MDSC in tumors.

Also M2-oriented TAM promote tumor progression. Overall CD11b$^{hi}$ Ly6C$^{lo}$ Ly6G$^{neg}$ TAM numbers only showed a trend towards a reduction in cDC2-vaccinated mice (FIG. 9D). Importantly, within the TAM compartment, cDC2 vaccination caused a shift towards more M1-like MHC-II$^{high}$ TAM (i.e. a lower MHC-II$^{low}$/MHC-II$^{high}$ TAM ratio) (FIGS. 9E and 9F). In addition, these MHC-II$^{high}$ TAM had a more pronounced M1 phenotype as compared to those from non-vaccinated animals, as evidenced by a further upregulated expression of M1-associated genes, while most M2-associated genes (except for Mmp9) did not significantly change (FIG. 9G). Notably, the few remaining MHC-II$^{low}$ TAM from cDC2-vaccinated mice also altered their M1 gene expression profile, with some genes being upregulated (Il1b, Ptgs2, Il12p40) and others downregulated (Tnf, Nos2). M2 genes in these cells remained mostly unchanged. Overall, these data show that the myeloid compartment of LLC-OVA tumors from cDC2-vaccinated mice is dominated by strongly M1-oriented TAM.

Figure 10:
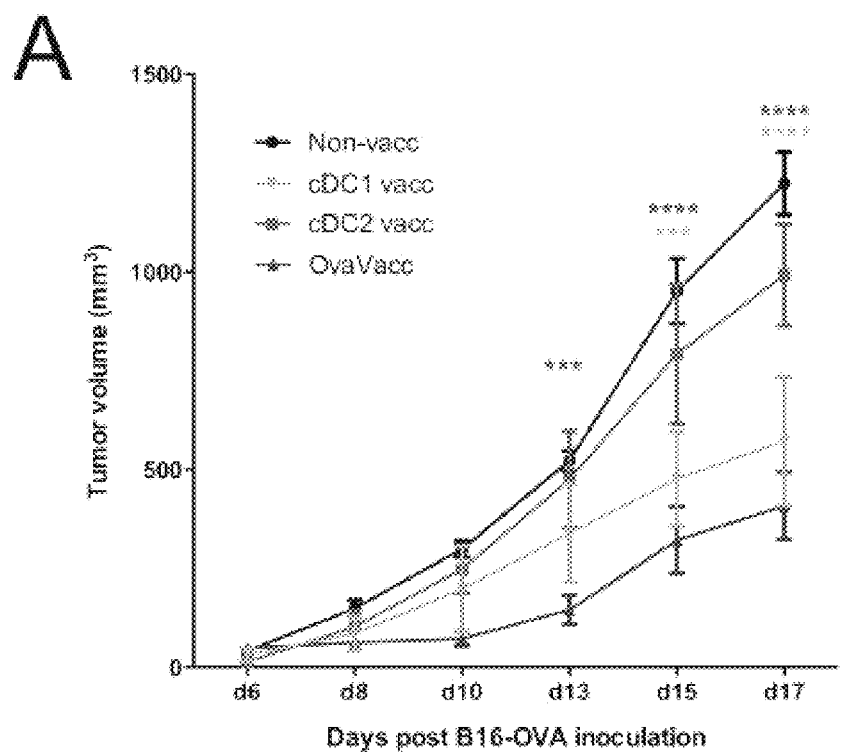
FIG. 10 shows that in B16 melanoma tumor-bearing mice, cDC1 vaccination is more effective than cDC2 vaccination. (A-B) Growth curve of B16-Ova tumors (A) and percentages of CD8$^+$ T cells in B16-Ova tumors (B) after vaccination with LLC-OVA TADC subsets following the protocol depicted in FIG. 8A. n=4 to 6 tumors. Statistical Analysis by one-way ANOVA. , p<0.01; *, p<0.001; ****, p<0.0001.
Figure 10:
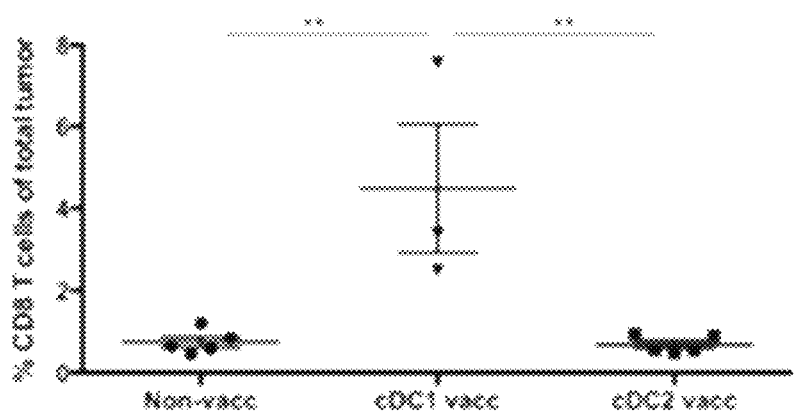

Finally, we turned to the B16-OVA tumor model, in which TAM are present in very low numbers and are mainly M1-like MHC-II$^{high}$ polarized (FIG. 2C). In this model, anti-tumor effects are more likely to be directly mediated by cytotoxic T cells without an overt interference of tumor-infiltrating myeloid cells. Indeed, vaccination with cDC1 isolated from LLC-OVA tumors (FIG. 10A) or B16-OVA tumors (FIGS. 13D and 13E) conferred respectively a better or equal protection than cDC2-vaccination, which correlated in the case of cDC1 sorted from LLC-OVA tumors with a significantly augmented infiltration of CD8$^+$ T cells in the former (FIG. 10B). Hence, depending on the role of TAM or TIL in tumor immunity, different tumor-derived conventional TADC subsets could be exploited to develop personalized DC adoptive immunotherapies.

Figure 11:
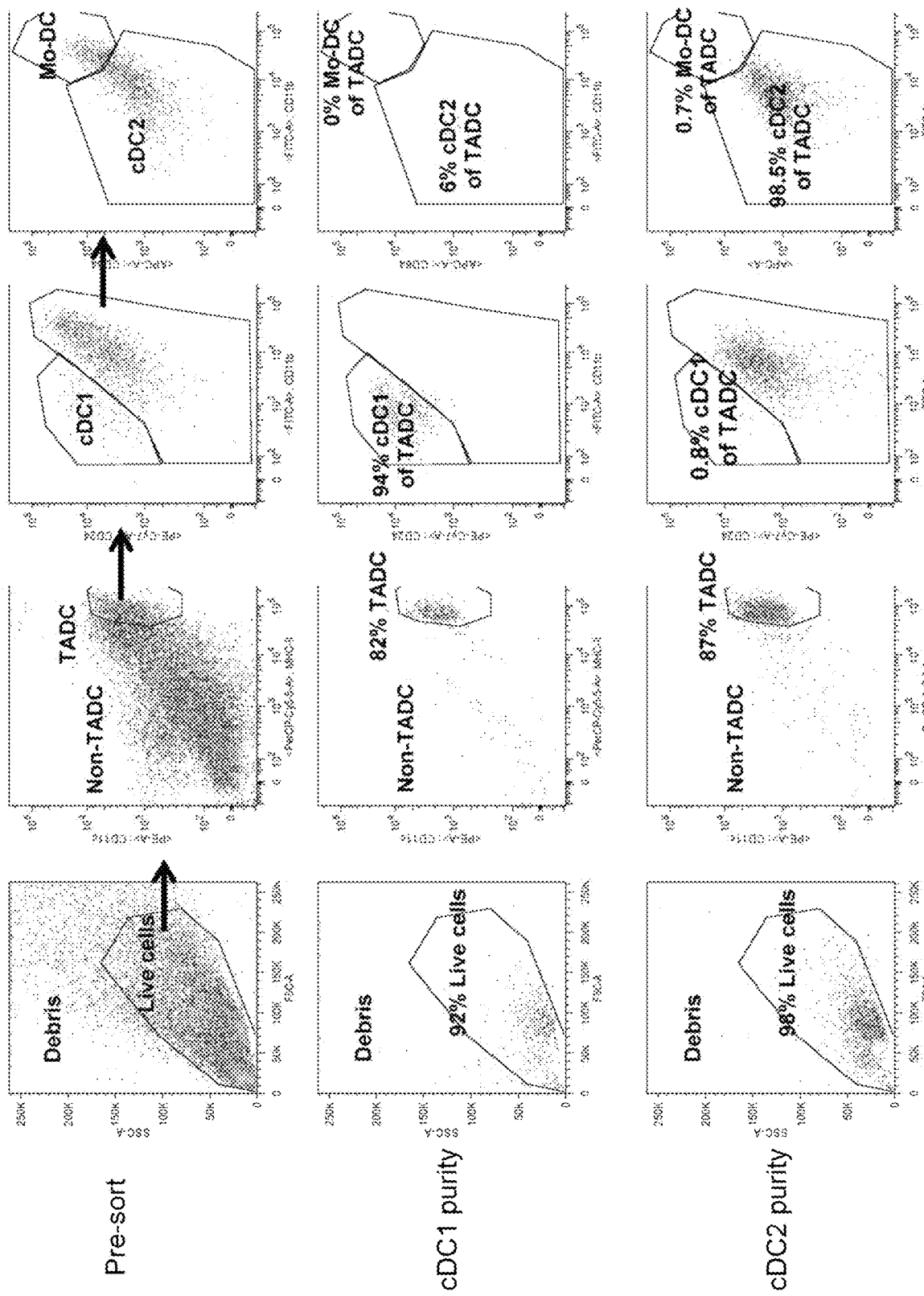
FIG. 11 shows the purities of FACS sorted cDC1 and cDC2 subsets. Representative plots and gating strategy are shown for (i) the total tumor after CD11c$^+$ magnetic sorting of 12-days tumor LLC-OVA tumors (i.e pre-sort) and for the FACS purities of the (ii) cDC1 and (iii) cDC2 populations that were used for the vaccinations experiments.

Example 9: The Gating Strategy Applied for Sorting cDC1 and cDC2 Populations from Total 12-Days Old LLC-OVA Tumors Used for the Vaccination Experiments Single-cell suspensions were prepared and CD11c$^+$ cells were MACS-enriched before sorting as described in the experimental procedures. The sorted cDC1 and cDC2 showed very high purities of 94% and 98.5% of the TADC and contained only minor Mo-DC contaminants (0% and 0.7%, respectively, FIG. 11).

Figure 12:
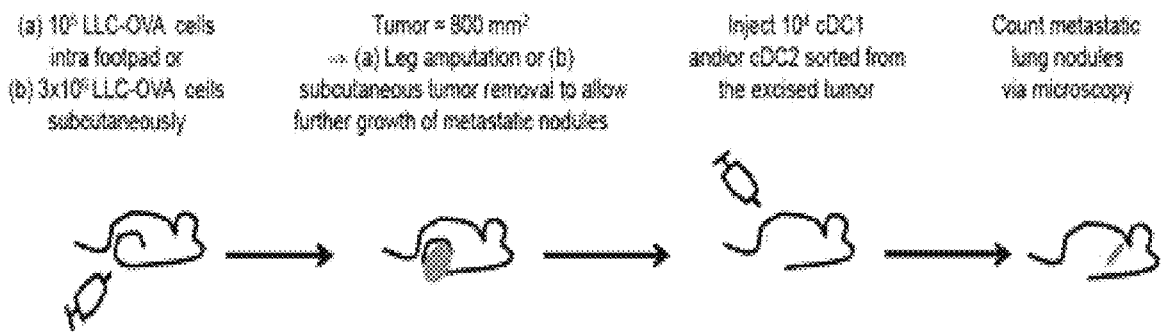
FIG. 12 shows the mouse models for evaluation of the therapeutic effect of TADC subsets in tumor metastasis. LLC-OVA cells are either injected into the footpad (10$^6$ cells) or subcutaneously (3×10$^6$ cells). Tumor is grown until a size of about 800 mm$^2$ and then resected by either leg amputation (a) or subcutaneous tumor removal (b). The TADC subsets are isolated from the resected tumor, further enriched by FACS and injected into the same mammal. The therapeutic effect on tumor metastasis is evaluated by measuring the weight of the lung and the weight and size of the metastatic lung nodules via microscopy.

Example 10: The Therapeutic Effect of TADC Subsets in Tumor Metastasis $10^5$ LLC-OVA cells are administered in the footpad (a) or $3\times10^6$ LLC-OVA cells are administered subcutaneously (b) and grown until a tumor size of about 800 mm$^2$. The primary tumor is then resected by either leg amputation (a) or subcutaneous tumor removal (b). cDC1 and/or cDC2 populations are isolated from the resected tumor and/or a resected tumor draining lymph node and subsequently injected back into the same individual. Metastatic lung nodules and lung weight are evaluated via microscopy (FIG. 12).

TABLE 1

Antibodies for flow cytometry (FACS).

| Marker | Clone | Source |
|---|---|---|
| 7AAD | — | BD Biosciences |
| B220 | Ra3-6B2 | BD Biosciences |
| BDCA-1 Biotin | AD5-8E7 | Miltenyi |
| BDCA-2 PE | AC144 | Miltenyi |
| CCR2 PE | 475301 | R&D systems |
| CCR3 PE | 83101 | R&D systems |
| CCR7 Biotin | 4B12 | eBioscience |
| CD1d PE | 1B1 | BD Biosciences |
| CD3 FITC | UCHT1 | eBioscience |
| CD4 PerCP-Cy5.5/Pe-Cy7/APC | RM4-5/GK1.5/RM4-5 | BD Biosciences/eBioscience |
| CD8a PE/PE/APC | YTS169.4/16-10A1/53-6.7 | Life technologies/eBioscience |
| CD11b BV605/PerCP-Cy5.5/AF488/PE-Cy7 | M1/70 | BD Biosciences/eBioscience |
| CD11c PerCP-Cy5.5/FITC/PE-Cy7/PE-Cy7 (anti-human)/PE/APC | N418/N418/HL3/3.9/HL3 | BD Biosciences/eBioscience |
| CD14 PB | TuK4 | Invitrogen |
| CD16 PE-TexasRed | 3G8 | Invitrogen |
| CD19 PE | 1D3 | BD Biosciences |
| CD19 FITC | HIB19 | BD Biosciences |
| CD24 PE/PE-Cy7 | M1/69 | eBioscience |
| CD40 FITC | 3/23 | BD Biosciences |
| CD45 AF700 (anti-human) | HI30 | BD Biosciences |
| CD45.1 FITC | A20 | eBioscience |
| CD45.2 AF700 | 104 | eBioscience |
| CD56 FITC | MEM188 | eBioscience |
| CD64 PE/APC | Y54-5/71 | Biolegend |
| CD80 PE | 16-10A1 | BD Biosciences |
| CD86 PE | GI-1 | BD Biosciences |
| CD103 biotin | M290 | BD Biosciences |
| CD127 eFluor450 | A7R34 | eBioscience |
| CD172a PE/APC | P84 | BD Biosciences/eBioscience |
| DEC-205 PE | 205yekta | eBioscience |
| Donkey anti-goat IgG AF647 | Polyclonal | Invitrogen |
| F4/80 PE/FITC | CI; A3-1 | Serotec |
| FcεR1 Biotin | MAR-1 | eBioscience |
| Fixable Live/Dead stain eFluor506 | / | eBioscience |
| Foxp3 PerCP-Cy5.5 | FJK-16s | eBioscience |
| Gata-3 AF647 | TWAJ | eBioscience |
| Goat anti-rabbit | Polyclonal IgG | Life Technologies |
| Goat IgG control biotin | Polyclonal goat IgG | R&D systems |
| IA/IE PerCP-Cy5.5/APC-eFluor780 | M5/114.15.2 | Biolegend/eBioscience |

TABLE 1-continued

Antibodies for flow cytometry (FACS).

| Marker | Clone | Source |
|---|---|---|
| IFN-γ APC | XMG12 | eBioscience |
| iso hamster IgG1, λ1 PE | G235-2356 | BD Biosciences |
| Iso mouse IgG1 k eFluor880 | eP3.6 2.8.1 | eBioscience |
| Iso Rat IgG1 k PE/APC | R3-34/eBRG1 | BD Biosciences/eBioscience |
| iso rat IgG2a Biotin/FITC/PE/APC | eBR2a/R35-95/R35-95/eBR2a | BD Biosciences/eBioscience |
| iso rat IgG2b, κ, PE/AF647 | A95-1/eB149/10H5 | BD Biosciences/eBioscience |
| IRF4 unlabeled | M-17 | Santa Cruz |
| IRF8 PerCP-Cy5.5 | V3GYWCH | eBioscience |
| HLA-DR APC-Cy7 | LN3 | eBioscience |
| KLRG1 APC-eFLuor780 | 2F1 | eBioscience |
| Ly6C AF488/AF647 | ER-MP20 | Serotec |
| Ly6G FITC/PE | 1A8 | BD Biosciences |
| MerTK Biotin | Polyclonal goat IgG | R&D systems |
| MitoSOX ™ Red (MitO2) | / | Life Technologies |
| NOS2 unlabeled | M17 | Santa Cruz |
| PD-L1 (B7-H1) PE | MIH5 | BD Biosciences |
| PD-L2 (B7-DC) PE | TY25 | eBioscience |
| Rabbit IgG unlabeled | Polyclonal rabbit IgG | Santa Cruz |
| RORγt APC | AFKJS-9 | eBioscience |
| SiglecF PE | E50-2440 | BD Biosciences |
| SIINFEKL Biotin | eBio25-D1.16 | eBioscience |
| SIINFEKL class I MHC dextramer APC | / | Immudex |
| Streptavidin BV786/PE | Streptavidin | BD Biosciences |
| T-bet eFluor660 | eBio4B10 | eBioscience |
| TCRb FITC | H57-597 | eBioscience |
| TNF-α PE | MP6-XT22 | eBioscience |
| XCR1 PE | ZET | Biolegend |

TABLE 2

Primer sequences for qRT-PCR.

| Gene | Forward Primer | Reverse Primer |
|---|---|---|
| Arg1 | TCACCTGAGCTTTGATGTCG | TTATGGTTACCCTCCCGTTG |
| Il1b | GTGTGGATCCAAAGGAATAC | GTCTGCTCATTCATGACAAG |
| Il4re | GCAGATGGCTCATGTCTGAA | CTCTGGGAAGCTGGGTGTAG |
| Il12B | TCAGGGACATCATCAAACCA | CTACGAGGAACGCACCTTTC |
| MMP9 | TGAATCAGCTGGCTTTTGTG | GTGGATAGCTCGGTGGTGTT |
| Mrc1 (MMR) | GCAAATGGAGCCGTCTGTGC | CTCGTGGATCTCCGTGACAC |
| Nos2 (iNOS) | GCTTCTGGTCGATGTCATGAG | TCCACCAGGAGATGTTGAAC |
| OVAL (of Gallus gallus) | CGTGGATTCTCAAACTGCAA | CACCAACATGCTCATTGTCC |
| Ptgs2 (COX2) | CAGGCTGAACTTCGAAACAG | CAGCTACGAAAACCCAATCA |
| Stab1 | ACGGGAAACTGCTTGATGTC | ACTCAGCGTCATGTTGTCCA |
| Tnf | CCTTCACAGAGCAATGACTC | GTCTACTCCCAGGTTCTCTTC |

REFERENCES

Bosschaerts, T., Morias, Y., Stijlemans, B., Herin, M., Porta, C., Sica, A., Mantovani, A., De Baetselier, P., and Beschin, A. (2011). IL-10 limits production of pathogenic TNF by M1 myeloid cells through induction of nuclear NF-kappaB p50 member in *Trypanosoma congolense* infection-resistant C57BL/6 mice. Eur J Immunol 41, 3270-3280.

Bronte, V., and Zanovello, P. (2005). Regulation of immune responses by L-arginine metabolism. Nature reviews Immunology 5, 641-654.

Broz, M. L., Binnewies, M., Boldajipour, B., Nelson, A. E., Pollack, J. L., Erle, D. J., Barczak, A., to Rosenblum, M. D., Daud, A., Barber, D. L., et al, (2014). Dissecting the tumor myeloid compartment reveals rare activating antigen-presenting cells critical for T cell immunity. Cancer Cell 26, 638-652.

Fridman, W. H., Galon, J., Pages, F., Tartour, E., Sautes-Fridman, C., and Kroemer, G. (2011). Prognostic and predictive impact of intra- and peritumoral immune infiltrates. Cancer Res 71, 5601-5605.

Gabrilovich, D. (2004). Mechanisms and functional significance of tumour-induced dendritic-cell defects. Nature reviews Immunology 4, 941-952.

Gao, Y., Nish, S. A., Jiang, R., Hou, L., Licona-Limon, P., Weinstein, J. S., Zhao, H., and Medzhitov, R. (2013). Control of T helper 2 responses by transcription factor IRF4-dependent dendritic cells. Immunity 39, 722-732.

Gautier, E. L., Shay, T., Miller, J., Greter, M., Jakubzick, C., Ivanov, S., Helft, J., Chow, A., Elpek, K. G., Gordonov, S., et al, (2012). Gene-expression profiles and transcriptional regulatory pathways that underlie the identity and diversity of mouse tissue macrophages. Nat Immunol 13, 1118-1128.

Goc, J., Germain, C., Vo-Bourgais, T. K., Lupo, A., Klein, C., Knockaert, S., de Chaisemartin, L., Ouakrim, H., Becht, E., Alifano, M., et al, (2014). Dendritic cells in tumor-associated tertiary lymphoid structures signal a Th1 cytotoxic immune contexture and license the positive prognostic value of infiltrating CD8+ T cells. Cancer Res 74, 705-715.

Greter, M., Helft, J., Chow, A., Hashimoto, D., Mortha, A., Agudo-Cantero, J., Bogunovic, M., Gautier, E. L., Miller, J., Leboeuf, M., et al, (2012). GM-CSF controls nonlymphoid tissue dendritic cell homeostasis but is dispensable for the differentiation of inflammatory dendritic cells. Immunity 36, 1031-1046.

Guilliams, M., Ginhoux, F., Jakubzick, C., Naik, S. H., Onai, N., Schraml, B. U., Segura, E., Tussiwand, R., and Yona, S. (2014). Dendritic cells, monocytes and macrophages: a unified nomenclature based on ontogeny. Nature reviews Immunology 14, 571-578.

Guilliams, M., Henri, S., Tamoutounour, S., Ardouin, L., Schwartz-Cornil, I., Dalod, M., and Malissen, B. (2010). From skin dendritic cells to a simplified classification of human and mouse dendritic cell subsets. Eur J Immunol 40, 2089-2094.

Heath, W. R., and Carbone, F. R. (2009). Dendritic cell subsets in primary and secondary T cell responses at body surfaces. Nat Immunol 10, 1237-1244.

Helft, J., Ginhoux, F., Bogunovic, M., and Merad, M. (2010). Origin and functional heterogeneity of non-lymphoid tissue dendritic cells in mice. Immunological reviews 234, 55-75.

Kingston, D., Schmid, M. A., Onai, N., Obata-Onai, A., Baumjohann, D., and Manz, M. G. (2009). The concerted action of GM-CSF and Flt3-ligand on in vivo dendritic cell homeostasis. Blood 114, 835-843.

Kissenpfennig, A., Henri, S., Dubois, B., Laplace-Builhe, C., Perrin, P., Romani, N., Tripp, C. H., Douillard, P., Leserman, L., Kaiserlian, D., et al, (2005). Dynamics and function of Langerhans cells in vivo: dermal dendritic cells colonize lymph node areas distinct from slower migrating Langerhans cells. Immunity 22, 643-654.

Langlet, C., Tamoutounour, S., Henri, S., Luche, H., Ardouin, L., Gregoire, C., Malissen, B., and Guilliams, M. (2012). CD64 expression distinguishes monocyte-derived and conventional dendritic cells and reveals their distinct role during intramuscular immunization. Journal of immunology 188, 1751-1760.

Laoui, D., Van Overmeire, E., Di Conza, G., Aldeni, C., Keirsse, J., Morias, Y., Movahedi, K., Houbracken, I., Schouppe, E., Elkrim, Y., et al, (2014). Tumor hypoxia does not drive differentiation of tumor-associated macrophages but rather fine-tunes the M2-like macrophage population. Cancer Res 74, 24-30.

Ma, Y., Shurin, G. V., Peiyuan, Z., and Shurin, M. R. (2013). Dendritic cells in the cancer microenvironment. Journal of Cancer 4, 36-44.

Movahedi, K., Laoui, D., Gysemans, C., Baeten, M., Stange, G., Van den Bossche, J., Mack, M., Pipeleers, D., In't Veld, P., De Baetselier, P., and Van Ginderachter, J. A. (2010). Different tumor microenvironments contain functionally distinct subsets of macrophages derived from Ly6C(high) monocytes. Cancer Res 70, 5728-5739.

Ohl, L., Mohaupt, M., Czeloth, N., Hintzen, G., Kiafard, Z., Zwirner, J., Blankenstein, T., Henning, G., and Forster, R. (2004). CCR7 governs skin dendritic cell migration under inflammatory and steady-state conditions. Immunity 21, 279-288.

Onai, N., Obata-Onai, A., Schmid, M. A., Ohteki, T., Jarrossay, D., and Manz, M. G. (2007). Identification of clonogenic common Flt3+M-CSFR+ plasmacytoid and conventional dendritic cell progenitors in mouse bone marrow. Nat Immunol 8, 1207-1216.

Persson, E. K., Uronen-Hansson, H., Semmrich, M., Rivollier, A., Hagerbrand, K., Marsal, J., Gudjonsson, S., Hakansson, U., Reizis, B., Kotarsky, K., and Agace, W. W. (2013). IRF4 transcription-factor-dependent CD103 (+)CD11b(+) dendritic cells drive mucosal T helper 17 cell differentiation. Immunity 38, 958-969.

Plantinga, M., Guilliams, M., Vanheerswynghels, M., Deswarte, K., Branco-Madeira, F., Toussaint, W., Vanhoutte, L., Neyt, K., Killeen, N., Malissen, B., et al, (2013). Conventional and monocyte-derived CD11b(+) dendritic cells initiate and maintain T helper 2 cell-mediated immunity to house dust mite allergen. Immunity 38, 322-335.

Preynat-Seauve, O., Schuler, P., Contassot, E., Beermann, F., Huard, B., and French, L. E. (2006). Tumor-infiltrating dendritic cells are potent antigen-presenting cells able to activate T cells and mediate tumor rejection. Journal of immunology 176, 61-67.

Remels, L. M., and De Baetselier, P. C. (1987). Characterization of 3LL-tumor variants generated by in vitro macrophage-mediated selection. International journal of cancer Journal international du cancer 39, 343-352.

Schlitzer, A., McGovern, N., Teo, P., Zelante, T., Atarashi, K., Low, D., Ho, A. W., See, P., Shin, A., Wasan, P. S., et al, (2013). IRF4 transcription factor-dependent CD11b+ dendritic cells in human and mouse control mucosal IL-17 cytokine responses. Immunity 38, 970-983.

Schouppe, E., Mommer, C., Movahedi, K., Laoui, D., Morias, Y., Gysemans, C., Luyckx, A., De Baetselier, P., and Van Ginderachter, J. A. (2013). Tumor-induced myeloid-derived suppressor cell subsets exert either inhibitory or stimulatory effects on distinct CD8+ T-cell activation events. Eur J Immunol 43, 2930-2942.

Scott, C. L., Bain, C. C., Wright, P. B., Sichien, D., Kotarsky, K., Persson, E. K., Luda, K., Guilliams, M., Lambrecht, B. N., Agace, W. W., et al, (2015). CCR2(+)CD103(-) intestinal dendritic cells develop from DC-committed precursors and induce interleukin-17 production by T cells. Mucosal immunology 8, 327-339.

Segura, E., Touzot, M., Bohineust, A., Cappuccio, A., Chiocchia, G., Hosmalin, A., Dalod, M., Soumelis, V., and Amigorena, S. (2013). Human inflammatory dendritic cells induce Th17 cell differentiation. Immunity 38, 336-348.

Serbina, N. V., Jia, T., Hohl, T. M., and Pamer, E. G. (2008). Monocyte-mediated defense against microbial pathogens. Annual review of immunology 26, 421-452.

Steinman, R. M., and Banchereau, J. (2007). Taking dendritic cells into medicine. Nature 449, 419-426.

Tamura, T., Tailor, P., Yamaoka, K., Kong, H. J., Tsujimura, H., O'Shea, J. J., Singh, H., and Ozato, K. (2005). IFN regulatory factor-4 and -8 govern dendritic cell subset development and their functional diversity. Journal of immunology 174, 2573-2581.

Vesely, M. D., Kershaw, M. H., Schreiber, R. D., and Smyth, M. J. (2011). Natural innate and adaptive immunity to cancer. Annual review of immunology 29, 235-271.

The invention claimed is:

1. A method of treating tumor metastasis in a subject, the method comprising:
administering to the subject a composition comprising an isolated tumor-associated dendritic cell (TADC) subset of pre-conventional dendritic cell (pre-cDC) origin, wherein the composition is essentially devoid of monocyte-derived dendritic cells (Mo-DCs), and wherein the TADC subset is isolated from a resected tumor or a resected tumor-draining lymph node of a mammal and is not ex-vivo stimulated with cytokines, nor ex-vivo loaded with tumor antigen.

2. The method according to claim 1, wherein the composition comprises no more than 1% Mo-DCs.

3. The method according to claim 1, wherein the TADC subset is CD16−, CD11c+, HLA-DR+, BDCA2−, and CD14−.

4. The method according to claim 3, wherein the TADC subset is BDCA1−, BDCA3+, and CD11b$^{lo}$.

5. The method according to claim 3, wherein the TADC subset is BDCA1+, BDCA3−, and CD11b+.

6. The method according to claim 1, further comprising:
isolating TADCs from a resected tumor or a resected tumor-draining lymph node of a mammal, and
enriching TADC subsets in a manner effective to obtain a population essentially devoid of Mo-DCs.

7. The method according to claim 6, wherein the enriching includes one or more of buoyant density centrifugation, magnetic-activated cell sorting (MACS), and fluorescently activated cell sorting (FACS).

* * * * *